(12) United States Patent
Hunt et al.

(10) Patent No.: US 10,281,473 B2
(45) Date of Patent: May 7, 2019

(54) COMPOSITIONS AND METHODS FOR ANALYSIS OF PROTEIN SEQUENCES AND POST-TRANSLATIONAL MODIFICATIONS

(71) Applicants: University of Virginia Patent Foundation, Charlottesville, VA (US); Donald F. Hunt, Charlottesville, VA (US); Weihan Wang, Charlottesville, VA (US); Lichao Zhang, Mountain View, CA (US)

(72) Inventors: Donald F. Hunt, Charlottesville, VA (US); Weihan Wang, Charlottesville, VA (US); Lichao Zhang, Mountain View, CA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 79 days.

(21) Appl. No.: 15/116,609

(22) PCT Filed: Feb. 4, 2015

(86) PCT No.: PCT/US2015/014440
§ 371 (c)(1),
(2) Date: Aug. 4, 2016

(87) PCT Pub. No.: WO2015/120036
PCT Pub. Date: Aug. 13, 2015

(65) Prior Publication Data
US 2016/0349269 A1    Dec. 1, 2016

Related U.S. Application Data

(60) Provisional application No. 61/935,503, filed on Feb. 4, 2014.

(51) Int. Cl.
*G01N 33/68* (2006.01)

(52) U.S. Cl.
CPC ..... *G01N 33/6848* (2013.01); *G01N 33/6854* (2013.01); *G01N 2440/00* (2013.01);
(Continued)

(58) Field of Classification Search
CPC ............... G01N 33/68; G01N 33/6803; G01N 33/6818; G01N 33/6842; G01N 33/6848;
(Continued)

(56) References Cited

U.S. PATENT DOCUMENTS 6,558,671 B1    5/2003    Slingluff et al.
7,300,753 B2 *  11/2007   Rush ...................... C07K 14/47
                                                              435/174

(Continued)

FOREIGN PATENT DOCUMENTS

WO    WO 03/031982    4/2003

OTHER PUBLICATIONS

Ahn et al. Accessing the reproducibility and specificity of pepsin and other aspartic proteases. Biochimica et Biophysica Acta Proteins and Proteomics. 2013, vol. 1834, pp. 1222-1229.*
(Continued)

*Primary Examiner* — Jeffrey E. Russel
(74) *Attorney, Agent, or Firm* — Rodney L. Sparks

(57) ABSTRACT

The application discloses compositions, methods, systems, and apparatuses for rapid sequence analysis of proteins, including location of post-translational modifications and disulfide bonds. Limited digestion of fully denatured antibody occurs in seconds by flowing sample in 8M urea at constant pressure through a micro column reactor containing immobilized aspergillopepsin I, resulting in a product mixture containing 3-10 kDa peptides, which is then fractionated by capillary column chromatography and analyzed by both electron transfer dissociation (ETD) and collision activated dissociation mass spectrometry. This method provides
(Continued)

Principle of size-controlled proteolysis using an enzyme reactor.

95% sequence coverage of a mAb and detects numerous post-translational modifications. For disulfide bond location, native mAb is subjected to longer digestion times. Release of disulfide containing peptides from accessible regions of the folded protein occurs with short digestion times. The identity of peptides connected by a disulfide bond is determined using ETD and ion-ion proton transfer chemistry.

39 Claims, 64 Drawing Sheets
(11 of 64 Drawing Sheet(s) Filed in Color)
Specification includes a Sequence Listing.

(52) U.S. Cl.
CPC ..... *G01N 2440/16* (2013.01); *G01N 2440/20* (2013.01); *G01N 2440/38* (2013.01); *G01N 2560/00* (2013.01)

(58) Field of Classification Search
CPC ....... G01N 2440/00–2440/40; G01N 2560/00; G01N 2570/00
See application file for complete search history.

(56) References Cited

U.S. PATENT DOCUMENTS

| | | | | |
|---|---|---|---|---|
| 7,529,629 | B2* | 5/2009 | Wang | G06F 19/703 435/4 |
| 8,074,494 | B2* | 12/2011 | Vorm | B01D 15/1871 73/61.53 |
| 2007/0092924 | A1* | 4/2007 | Anderson | C12Q 1/37 435/23 |
| 2007/0110757 | A1* | 5/2007 | Wei | A61K 9/0019 424/159.1 |
| 2007/0178526 | A1* | 8/2007 | Kountakis | G01N 33/6803 435/7.1 |
| 2007/0284308 | A1 | 12/2007 | Zare et al. | |
| 2008/0044915 | A1 | 2/2008 | Hunt et al. | |
| 2009/0098638 | A1 | 4/2009 | Abbas et al. | |
| 2009/0203068 | A1 | 8/2009 | Lopez-Ferrer et al. | |
| 2012/0003668 | A1* | 1/2012 | Hindie | C07C 57/60 435/7.8 |
| 2013/0330294 | A1* | 12/2013 | Mellins | A61K 35/17 424/85.2 |
| 2014/0224983 | A1* | 8/2014 | Chingin | H01J 49/14 250/288 |

OTHER PUBLICATIONS

Anderson, L.C. Analyses of Intact Proteins Using Novel Mass Spectrometric Techniques. A Dissertation Presented to the Graduate Faculty of the University of Virginia in Candidacy for the Degree of Doctor of Philosophy. Aug. 2014.*
Carr et al. Protein and Carbohydrate Structural Analysis of a Recombinant Soluble CD4 Receptor by Mass Spectrometry. The Journal of Biological Chemistry. Dec. 15, 1989, vol. 263, No. 35, pp. 21286-21295.*
Ehring, H. Hydrogen Exchange/Electrospray Ionization Mass Spectrometry Studies of Structural Features of Proteins . . . Analytical Biochemistry. 1999, vol. 267, pp. 252-259.*
Tyagarajan, et al., "Thiol-reactive dyes for fluorescence labeling of proteomic samples", Electrophoresis, Jul. 2003, vol. 24, p. 2348-2358, entire document.
Ma, et al., "Recent advances in immobilized enzymatic reactors and their applications in proteome analysis," Analytica Chimica Acta, Sep. 1, 2007 (Jan. 9, 2007), vol. 632, pp. 1-8. Entire document.
Inoue, et al., "Heterologous expression and site-directed mutagenesis studies on the activation mechanism and the roles of the basic residues in the prosegment of aspergillopepsinogen I", European Journal of Biochemistry, 1996, vol. 237, p. 719-725, entire document.
Lanucara, F and Eyers, C. E. (2013) Top-down mass spectrometry for the analysis of combinatorial post-translational modifications. Mass Spectrom. Rev. 32, 27-42.
Kalli, A., Sweredoski, M. J., and Hess, S. (2013) Data-dependent middle-down nano-liquid chromatography-electron capture dissociation-tandem mass spectrometry: An application for the analysis of unfractionated histones. Anal. Chem. 85, 3501-3507.
Wu, S., Kim, J., Hancock, W. S., and Karger, B. (2005) Extended range proteomic analysis (ERPA): A new and sensitive LC-MS platform for high sequence coverage of complex proteins with extensive post-translational ModificationsComprehensive analysis of beta-casein and epidermal growth factor receptor (EGFR). J. Proteome Res. 4, 1155-1170.
Garcia, B. A., Siuti, N., Thomas, C. E., Mizzen, C. A., and Kelleher, N. L. (2007) Characterization of neurohistone variants and post-translational modifications by electron capture dissociation mass spectrometry. Int. J. Mass Spectrom. 259, 184-196.
Tan, Y., Wang, W., Zheng, Y., Dong, J., Stefano, G., Brandizzi, F., Garavito, R. M., Reid, G.E., and Bruening, M. L. (2012) Limited proteolysis via millisecond digestions in protease-modified membranes. Anal. Chem. 84, 8357-8363.
Switzar L, Giera M, Niessen WMA, Protein Digestion: An Overview of the Available Techniques and Recent Developments, J Proteome Res 2013;12:1067-1077.
Earley L, et al. "Front-End Electron Transfer Dissociation: A New Ionization Source", Anal Chem, 2013;85 (17):8385-3390. PMCID: PMC 3822909.

* cited by examiner

E

Cys modified with iodoacetamide, ETD

D-I-V-L-M-T-Q-T-P-L-S-L-P-V-S-L-G-D-Q-A-S-I-S-C-R-S-S-Q-Y-I-V-H-S-N-G-N-T-Y-L-E-W-Y-L-Q-K-P-G-Q-S-P-K-L-L

Cys modified with aminoethylmaleimide, ETD

D-I-V-L-M-T-Q-T-P-L-S-L-P-V-S-L-G-D-Q-A-S-I-S-C-R-S-S-Q-Y-I-V-H-S-N-G-N-T-Y-L-E-W-Y-L-Q-K-P-G-Q-S-P-K-L-L

Cys modified with aminoethylmaleimide, ETD and CAD

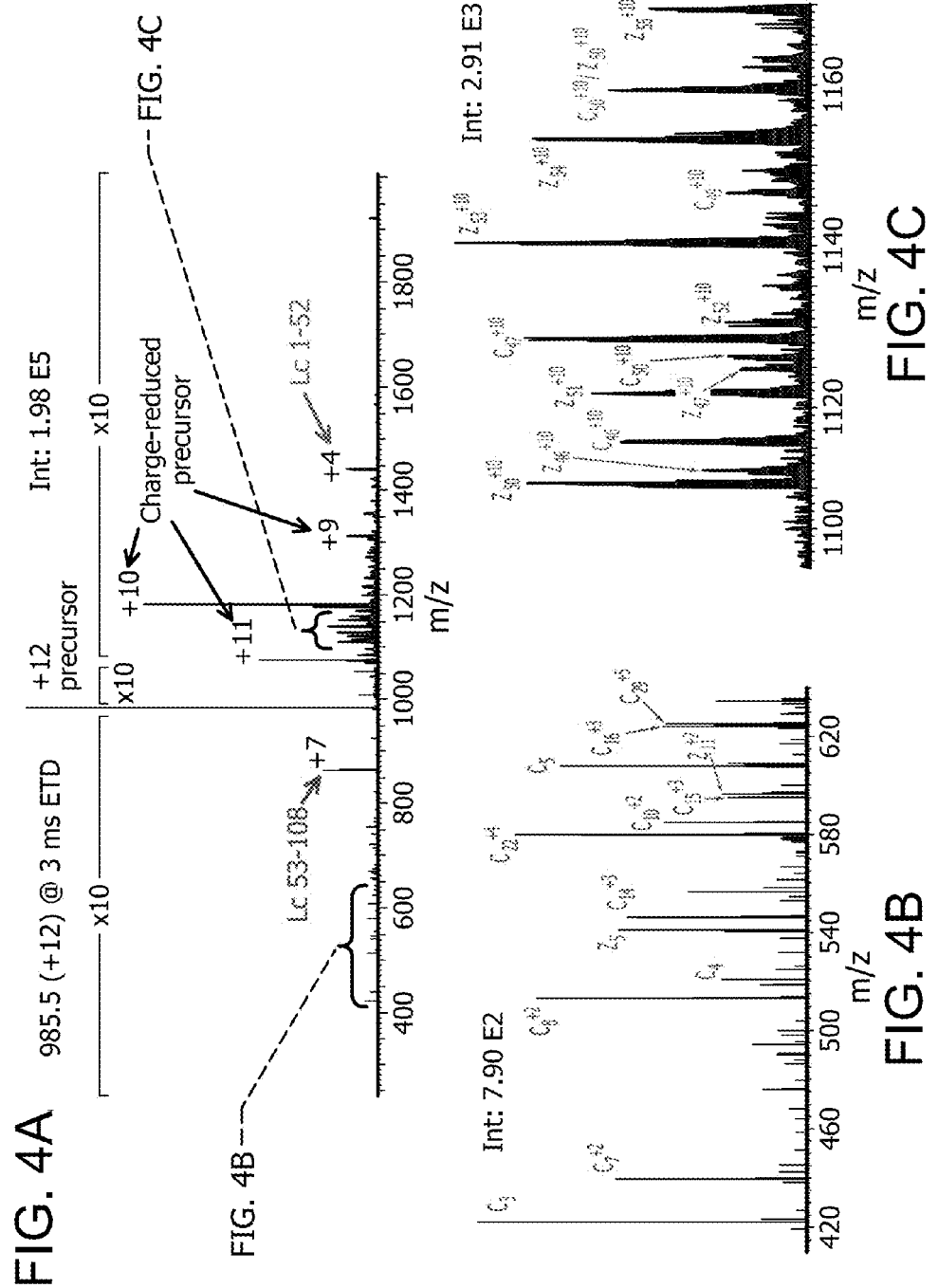

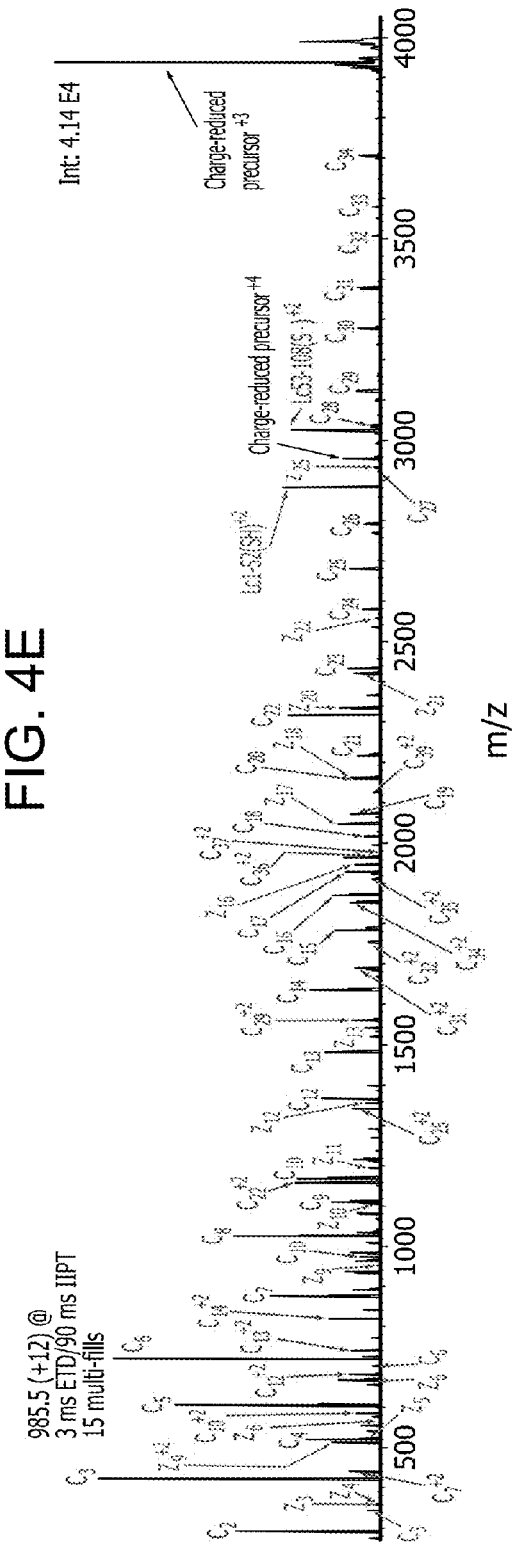

Principle of size-controlled proteolysis using an enzyme reactor.

1   GLSDGEW-QQVLNVWGKV-EADLAG   23
24  HGQEVLIR-L-FTGH-PETLEKFDKF   46
47  KHLKTEAEMKASEDLKKHGTVVL     69
70  -TALGLKKGHHEAELK-PLAQS      92
93  HATKHK-PKYLEFISDALHVL       115
116 HSKH-PGDFGADAQGAMTKALELF    138
139 RNDAKYKELGFQG-              153

FIG. 7

```
1    DIVLMTQTPLSLPVSLGDQASISC        23
24   RSSQYLVHSNGNTYLEWYLQKPG         46
47   QS-PKLLIYKVSNRFSGVPDRFSG        69
70   SGSGTDFTLKISRVEAEDLGVYY         92
93   CFQGSHVPLTFGAGTKLEIKRAD         93
116  AAPTVSIFPPSSEQLTSGGASVV         138
139  CFLNNFYPKD-INVKWKIDGSERQ        161
162  NGVLNSWTDQDS-KDSTYSMSSTL        184
185  TLTKDEYER-HNSYTCEATHKT-S-T      207
208  SPIVKSFNRNEC                    219
```

FIG. 8A

```
1    QLVQLKESGPGLVAPSQSLSITCT     23
24   VSGFSLLGYGVNWVRQPPGQGLE      46
47   WLM-GWGDGSTDYNSAL-KSRLS-I    69
70   TKDNSKSQVFLKMNSLQTDDT-AK     92
93   YYC-TRA-PYGKQYFAYWGQGTLV     93
116  VSAKTTPPSVYPLAPGSAQTN        138
139  SMVTLGCL-VKGYFPEP-VTVTWNS    161
162  GSLSSGVHTFPAVLQSDLYTLSS      184
185  SVTVPSSTWPSET-V-T-CNVAHPAS   207
208  S-TKVDKKIVPRDCG-CK-P-C-I-CTVP 219
231  EVSSVFIFP-PKPKDVLTITLTPK     232
254  VTCVVVD-ISKDDPEVQFSWFVDD     253
277  VEVHTAHTQ-PREEQFNSTFRS-VS    276
300  EL-P-IMHQDWLNGKEFKCRVN-SAA   299
323  FPAPIEKTISKTKGRPKA-PQVYT     322
346  I-PPPKEQMAKDKVSLTCMITDF      345
369  PED-ITVEWQWNGQPAENYKNTQP     368
392  IMDTDGSYFVYS-KLNVQKSN-WEA    391
415  GNTFTCSVLHEGLHNHHTEKSLS      414
438  HIS-PG-                      441
```

FIG. 8B

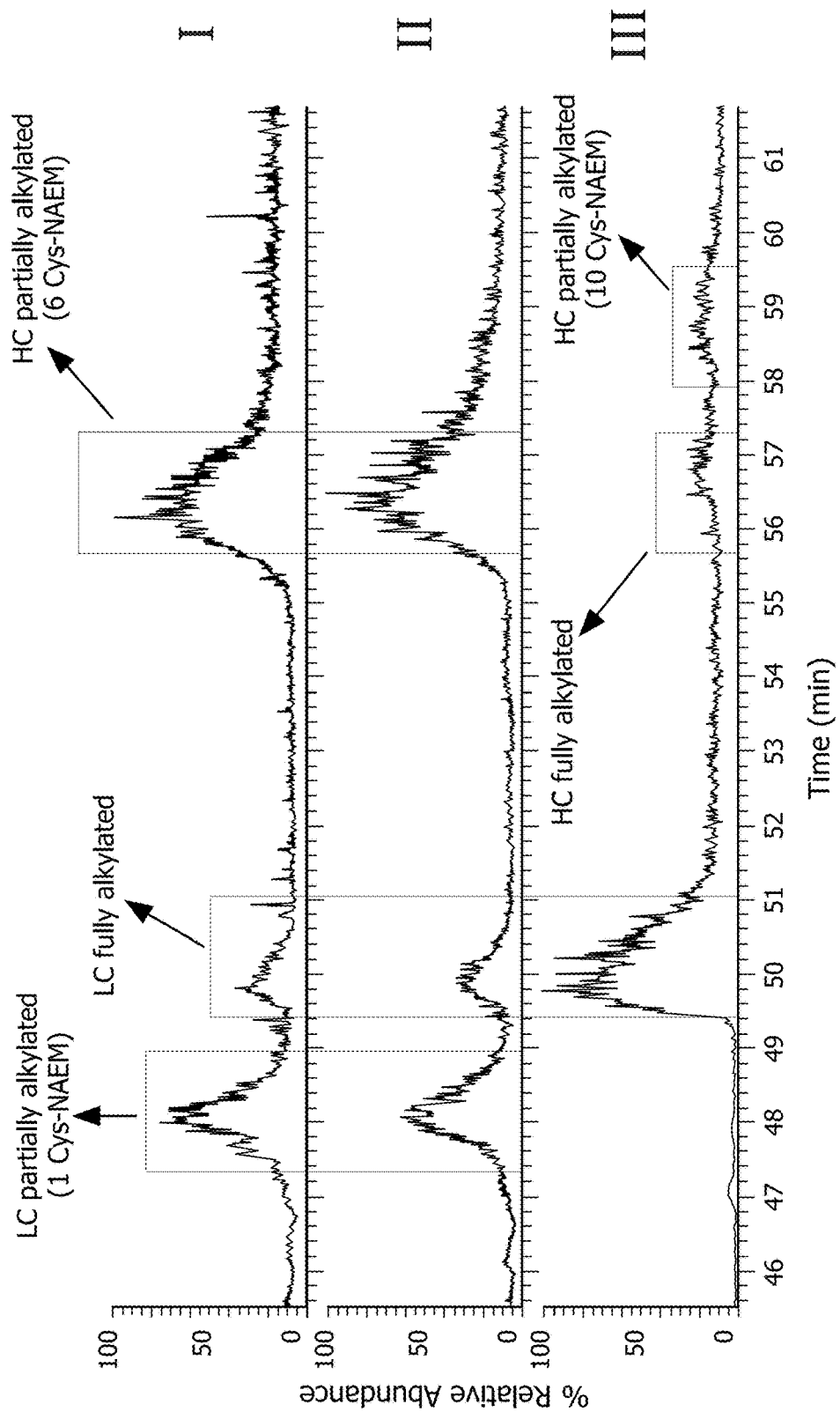
FIG. 10A1

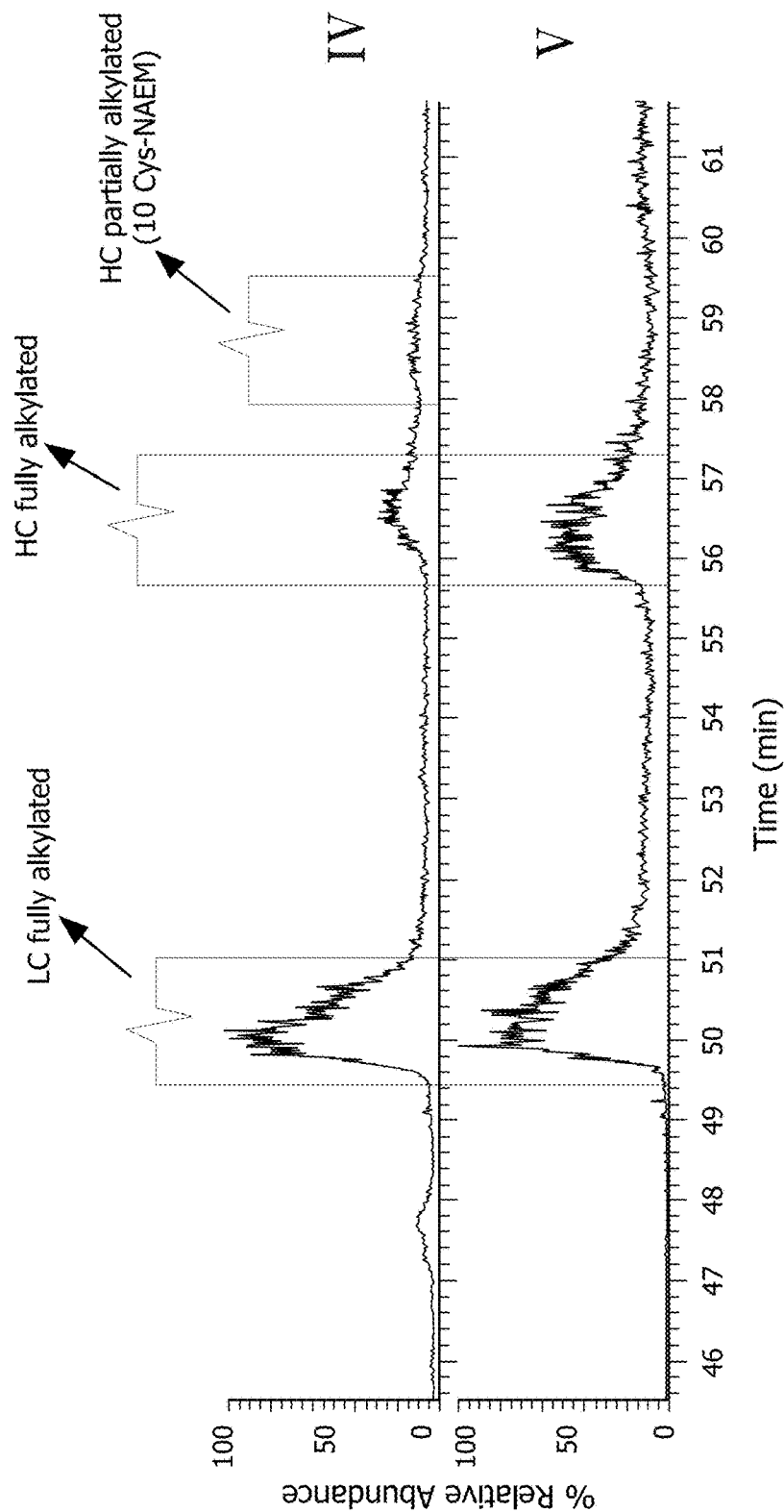
FIG. 10A2

I. Reduction in a buffer containing 2 mM dithiothreitol/6 M urea/0.5 M $NH_4Ac$ (final pH 6.8) at 37°C for 30 minutes.

Alkylation in a buffer containing 10 mM NAEM/6 M urea/ 0.5 M $NH_4Ac$ (final pH 6.8) at room temperature for 10 minutes.

II. Reduction in a buffer containing 5 mM TECP·HCl/6 M urea/0.5 M $NH_4Ac$ (final pH 6.8) at 37°C for 30 minutes.

Alkylation in a buffer containing 10 mM NAEM/6 M urea/ 0.5 M $NH_4Ac$ (pH 6.8) at room temperature for 10 minutes.

III. Reduction in water containing 2 mM TECP·HCl (final pH 2.5) at 80°C for 10 minutes.

Alkylation in a buffer containing 10 mM NAEM/6 M urea/ 0.5 M $NH_4Ac$ (final pH 6.8) at room temperature for 10 minutes.

IV. Reduction in a buffer containing 10 mM TECP·HCl/0.1% AcOH (final pH 2) at 80°C for 30 minutes.

Alkylation in a buffer containing 10 mM NAEM/6 M urea/ 0.5 M $NH_4Ac$ (final pH 6.8) at room temperature for 10 minutes.

V. Reduction in a buffer containing 10 mM TECP·HCl/0.1% AcOH/8 M urea (pH 4) at 50°C for 10 minutes.

Alkylation in a buffer containing 10 mM NAEM/8 M urea/ 0.5 M $NH_4Ac$ (final pH 6.8) at room temperature for 10 minutes.

FIG. 10B

Fully alkylated (12 Cys-NAEM)

Partially alkylated
(6 Cys-NAEM + 3 disulfides)

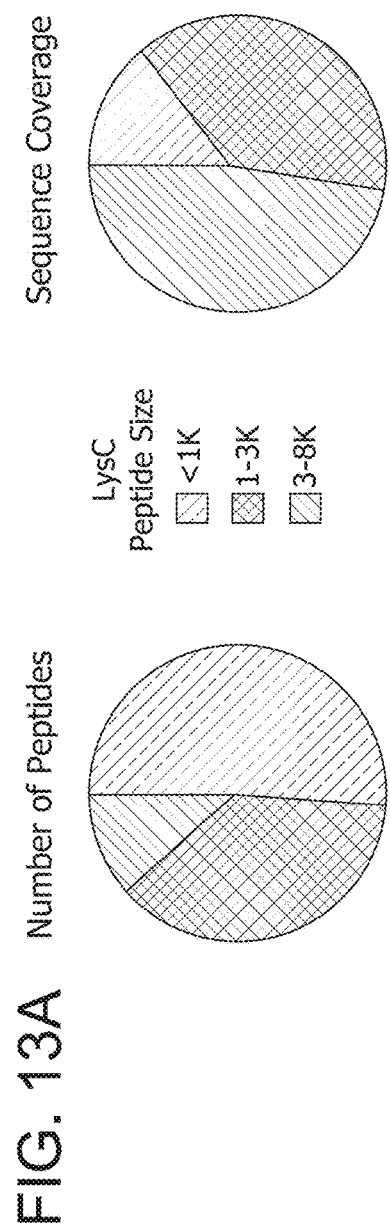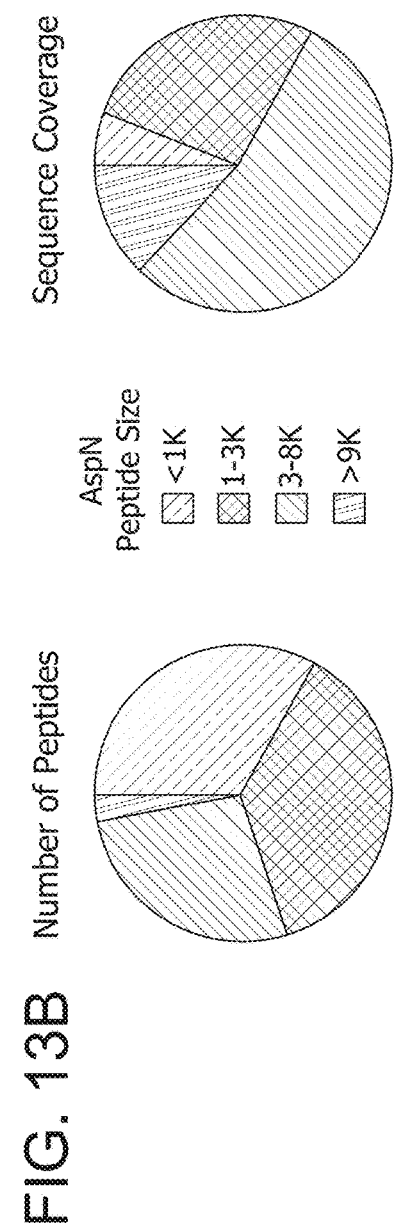
FIG. 13A
FIG. 13B

B

1:1 DIVLMTQTPLS LPVSLGDQAS ISCRSSQYIV HSNGNTYLEW YLQKPGQSPK
1:51 LLIYKVSNRF SGVPDRFSGS GSGTDFTLKI SRVEAEDLGV YYCFQGSHVP
1:101 LTFGAGTKLE IKRADAAPTV SIFPPSSEQL TSGGASVVCF LNNFYPKDIN
1:151 VKWKIDGSER QNGVLNSWTD QDSKDSTYSM SSTLTLTKDE YERHNSYTCE
1:201 ATHKTSTSPI VKSFNRNEC

Light chain

2:1 QVQLKESGPG LVAPSQSLSI TCTVSGFSLL GYGVNWVRQP PGQGLEWLMG
2:51 IWGDGSTDYN SALKSRISIT KDNSKSQVFL KMNSLQTDDT AKYYCTRAPY
2:101 GKDYFAYWGQ GTLVTVSAAK TTPPSVYPLA PGSAAQTNSM VTLGCLVKGY
2:151 FPEPVTVTWN SGSLSSGVHT FPAVLQSDLY TLSSSVTVPS STWPSETVTC
2:201 NVAHPASSTK VDKKIEPRDC GCKPCICTVP EVSSVFIFPP KPKDVLTITL
2:251 TPKVTCVVVD ISKDDPEVQF SWFVDDVEVH TAQTQPREEQ FNSTFRSVSE
2:301 LPIMHQDWLN GKEFKCRVNS AAFPAPIEKT ISKTKGRPKA PQVYTIPPPK
2:351 EQMAKDKVSL TCMITDFFPE DITVEWQWNG QPAENYKNTQ PIMDTDGSYF
2:401 VYSKLNVQKS NWEAGNTFTC SVLHEGLHNH HTEKSLSHSP G

Heavy chain

3:1 QVQLKESGPG LVAPSQSLSI TCTVSGFSLL GYGVNWVRQP PGQGLEWLMG
3:51 IWGDGSTDYN SALKSRISIT KDNSKSQVFL KMNSLQTDDT AKYYCTRAPY
3:101 GKDYFAYWGQ GTLVTVSAAK TTPPSVYPLA PGSAAQTNSM VTLGCLVKGY
3:151 FPEPVTVTWN SGSLSSGVHT FPAVLQSDLY TLSSSVTVPS STWPSETVTC
3:201 NVAHPASSTK VDKKIEPRDC GCKPCICTVP EVSSVFIFPP KPKDVLTITL
3:251 TPKVTCVVVD ISKDDPEVQF SWFVDDVEVH TAQTQPREEQ FNSTFRSVSE
3:301 LPIMHQDWLN GKEFKCRVNS AAFPAPIEKT ISKTKGRPKA PQVYTIPPPK
3:351 EQMAKDKVSL TCMITDFFPE DITVEWQWNG QPAENYKNTQ PIMDTDGSYF
3:401 VYSKLNVQKS NWEAGNTFTC SVLHEGLHNH HTEKSLSHSP G

Heavy chain

4:1 DIVLMTQTPLS LPVSLGDQAS ISCRSSQYIV HSNGNTYLEW YLQKPGQSPK
4:51 LLIYKVSNRF SGVPDRFSGS GSGTDFTLKI SRVEAEDLGV YYCFQGSHVP
4:101 LTFGAGTKLE IKRADAAPTV SIFPPSSEQL TSGGASVVCF LNNFYPKDIN
4:151 VKWKIDGSER QNGVLNSWTD QDSKDSTYSM SSTLTLTKDE YERHNSYTCE
4:201 ATHKTSTSPI VKSFNRNEC

Light chain

FIG. 18B

FIG. 24A
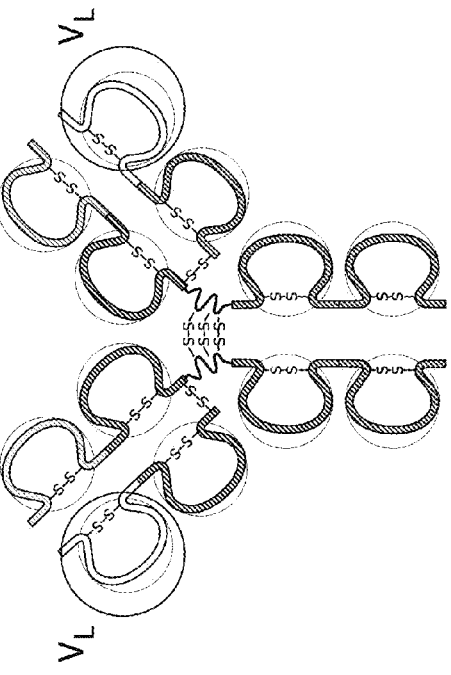
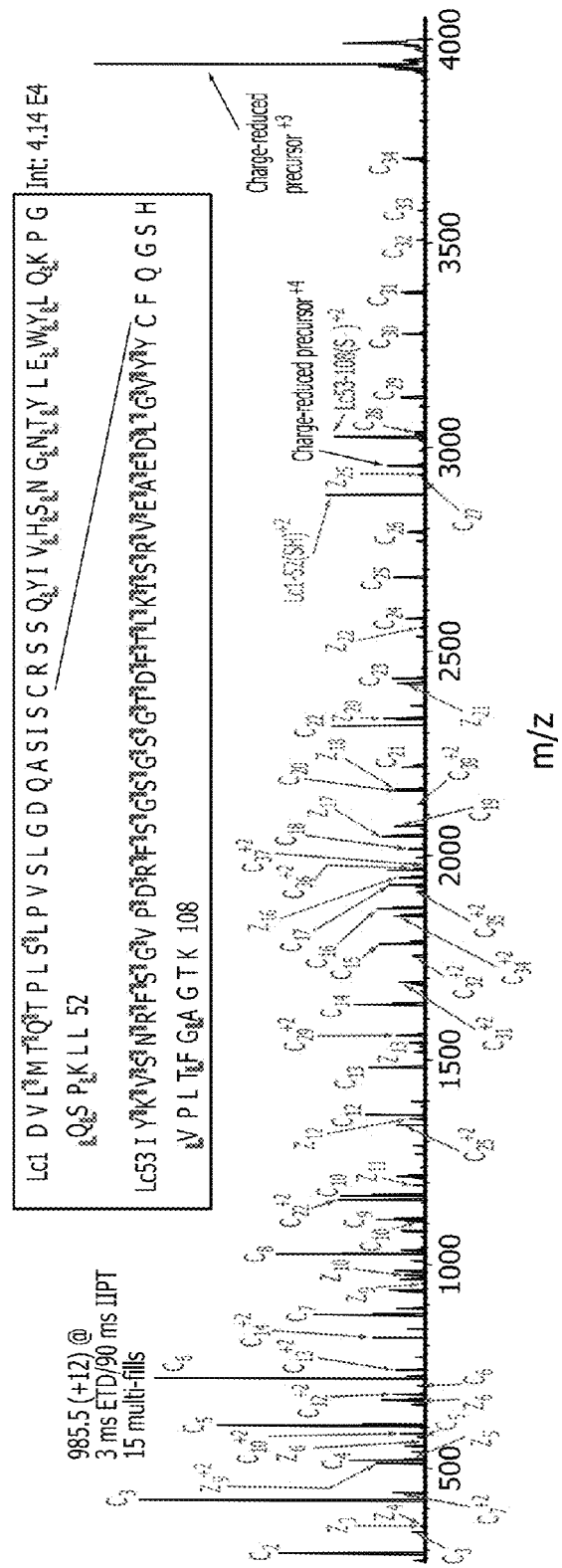

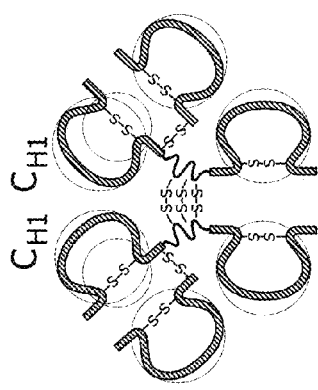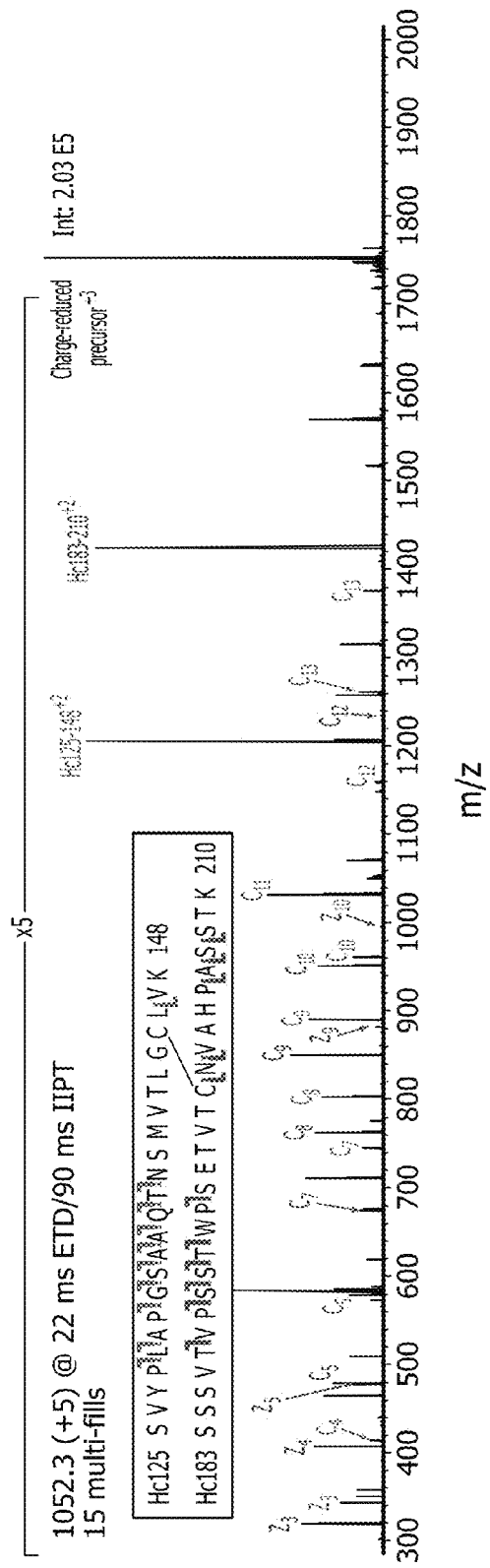
FIG. 24E

COMPOSITIONS AND METHODS FOR ANALYSIS OF PROTEIN SEQUENCES AND POST-TRANSLATIONAL MODIFICATIONS

CROSS REFERENCE TO RELATED APPLICATIONS

The present application is a national stage filing of International Application No. PCT/US2015/14440, filed Feb. 4, 2015, which claims priority under 35 U.S.C.§ 119(e) from U.S. Provisional Application Ser. No. 61/935,503, filed Feb. 4, 2014. The entire disclosure of the afore-mentioned patent application incorporated herein by reference.

STATEMENT REGARDING FEDERALLY SPONSORED RESEARCH OR DEVELOPMENT

This invention was made with government support under Grant Nos. GM037537 and AI033993, awarded by The National Institutes of Health. The government has certain rights in the invention.

BACKGROUND

Monoclonal antibodies (mAbs) and related products constitute one of the most rapidly growing classes of human therapeutics. These large (~150 kDa) proteins contain two identical (~50 kDa) heavy chains and two identical (~25 kDa) light chains. They also contain 16 or 17 disulfide bonds that maintain the three dimensional structure of the molecule. Different mAbs differ greatly in the sequence of their variable regions near the N-termini of both light and heavy chains. The most variable parts are complementarity-determining regions (CDRs), which are unique to individual mAbs and are responsible for the diversity and specificity of antibody bonding. Changes to the mAb structure introduced during the manufacturing process or storage can change the therapeutic efficacy, clearance, and immunogenicity properties of the protein and thus alter drug safety (11-14).

Therapeutic antibodies can have heterogeneities resulting from various modifications that occur during different stages of production, such as mutations, C-terminal lysine processing, pyroglutamic acid formation, oxidation, amidation, deamidation, glycosylation, and disulfide linkages. Identification of the primary sequence of therapeutic mAbs, as well as elucidation of the N-glycan structures, disulfide linkages and other PTMs, is critical for the evaluations of drug safety, efficacy, stability, as well as understanding the structure/function relationships. The demands for characterization of therapeutic mAbs are increasing with the rapid development of mAb-based pharmaceuticals. Moreover, the ability to readily generate such structure/function information with respect to a reference mAb would greatly accelerate the market entry of mAbs that could be deemed biosimilar to the reference mAb.

Widely adopted methods for protein structural characterizations by mass spectrometry (MS) involve a "bottom-up" approach. These methods are associated with complete tryptic digestion of the protein(s) into smaller peptides (<3000 Da) prior to MS analyses. Although useful for tandem MS (MS/MS, also referred to as MS2) analysis, small tryptic peptides often result in problems such as high sample complexity, difficulties in assigning peptides to specific gene products, and loss of combinatorial post-translational modifications (PTMs) information. Recent years have seen efforts toward achieving direct MS analysis of intact proteins (often called "top-down" MS). This approach aims to overcome the above issues by providing an overview of the entire protein sequence and PTMs. However, intact protein MS is still far from maturity in terms of being able to characterize large proteins. This is in part due to reasons such as inefficient gas-phase protein fragmentation and complex fragment ions that restrict efficient data interpretation. For example, the reported highest sequence coverage of intact therapeutic monoclonal antibodies (immunoglobulin G, 150 kDa) is no more than 35%, obtained by either ETD Orbitrap Fourier transform (FT) MS (Tsybin MCP 2012) or electron-capture dissociation (ECD) on a custom-built 9.4 T FT ion cyclotron resonance mass spectrometer (Marshall, Anal Chem. 2013, 85, 4239-4246).

There is a long felt need in the art for compositions, methods, and apparatuses useful for rapid sequence analysis of proteins, identification of post-translational modifications, and localization of disulfide bonds. The present invention satisfies these needs.

SUMMARY OF THE INVENTION

Disclosed herein are compositions, methods, systems, and apparatuses for the rapid characterization of proteins. The characterization includes sequencing, identification and characterization of post-translational modifications (PTMs), and localization of disulfide bonds. In one aspect, the protein is an immunoglobulin, such as IgG. Relative to currently used techniques in the art, the present invention provides and easy, precise control of digestion time to generate IgG peptides with desired medium length that facilitates LC-MS based sample analysis. In addition, the present application discloses that the protease aspergillopepsin I immobilized on a column preserves its activity for at least 1 hr, even in the extreme denaturation conditions in the presence of 8M urea. This condition unfolds alkylated IgG to the most extent that allows the chopping of IgG molecule into 3-10 kDa medium peptides with similar abundance. These peptides are favorable to HPLC separation and high resolution tandem MS analysis. When digesting a protein with a highly folded native structure (e.g. IgG without disulfide reduction or highly folded protein existed in a non-denaturation condition), this on-column time-control mode digestion allows very brief digestion at only the flexible region of the protein. This feature allows for the generation of some ultra-large peptides that preserve the regional 3 D structure. LC MS characterization of each of these released "protein domains" would be much easier than characterizing the entire protein molecule.

Therefore, the present invention provides advantages over the art, including easy, precise control of digestion time to generate from proteins such as IgG, peptides with desired medium length that facilitate LC-MS based sample analysis. In addition, the use of protease aspergillopepsin I immobilized on a column preserves its activity for at least 1 hr in an extreme denaturation condition, i.e. 8M urea. This condition unfolds alkylated IgG to the an extent that allows fragmenting of the IgG molecule into 3-10 kDa medium peptides with similar abundance. These peptides are favorable to HPLC separation and high-resolution tandem MS analysis. When digesting a protein with a highly folded native structure (e.g. IgG without disulfide reduction or highly folded protein existed in a non-denaturation condition), this on-column time-control mode digestion allows very brief digestion at only the flexible region of the protein. This feature allows for the generation of some ultra-large peptides that preserve the regional 3 D structure. LC MS characterization of each of these released "protein domains" is easier than characterizing the entire protein molecule.

In one embodiment, the present invention provides compositions and methods for characterizing a protein using time-controlled digestion, size-controlled digestion, and multi-segment liquid chromatography tandem mass spectrometry. In one embodiment, the present invention provides a system for characterizing a protein using time-controlled digestion, size-controlled digestion, and multi-segment liquid chromatography tandem mass spectrometry. In one embodiment, the present invention provides an apparatus for characterizing a protein using time-controlled digestion, size-controlled digestion, and multi-segment liquid chromatography tandem mass spectrometry.

In one embodiment, at least two different proteins are characterized. In another embodiment, at least three different proteins are characterized.

In one embodiment, the present invention provides a method for characterizing a protein from a sample of interest. In one aspect, the protein is optionally denatured. In one aspect, the protein is dissolved in a digestion buffer. In one aspect, the digestion buffer comprising the protein is passed through a reaction chamber comprising at least one hydrolyzing agent. In one aspect, the protein contacts the hydrolyzing agent in the chamber and is present in the chamber for a period of time (t) sufficient to produce protein fragments and digestion of the protein occurs in the chamber. In one aspect, the passing of the digestion buffer comprising the protein through the chamber is done at an adjustable flow rate. In one aspect, the sample that has passed through the chamber is subjected to multi-segment liquid chromatography tandem mass spectrometry to characterize the protein. In one aspect, more than one protein is characterized. Characterization includes, but is not limited to, sequencing the protein fragments that have been generated and determining the sequence of the entire protein, identifying post-translational modifications (PTMs) of the protein, locating the PTMs, and locating disulfide bonds.

In one aspect, the protein is denatured before dissolving in the digestion buffer. In one aspect, the protein is exposed to the hydrolyzing agent under acidic and highly chaotropic conditions. In one aspect, the chaotropic conditions are urea at about 6 to about 9 Molar (M). In one aspect, the urea is at about 6, 7, or 8M. In one aspect, the urea is at about 8M. In one aspect, the urea is at 8M. In one aspect, the urea is used at a pH of about 3.0 to about 5.0. In one aspect, the urea is used at a pH of about 3.5 to about 4.5. In on aspect, the urea is used at a pH of about 3.9 or 4.0.

In one aspect, the digested protein fragments range from about 3 kilodaltons (kDa) in mass to about 10 kDa in mass. In one aspect, the digested protein fragments range from about 10 kDa in mass to about 20 kDa in mass. In one aspect, the digested protein fragments range from about 20 kDa in mass to about 50 kDa in mass.

In one aspect, the site of a disulfide bond is identified. In one aspect, the sites of more than one disulfide bond are identified.

In one aspect, the digested protein is subjected to electron transfer dissociation (ETD)/ion-ion proton transfer (IIPT) to identify the disulfide-containing fragments and N- and C-terminal sequences and to localize the disulfide(s) within/connecting different domains. In one aspect, the digestion times for a disulfide analysis are from about 10 seconds (s) to about 20 minutes (min). In one aspect, the digestion times for a disulfide analysis are selected from about 12 s to about 10 min. In one aspect, the digestion times for a disulfide analysis are selected from the group consisting of about 12 s, 93 s, 260 s, and 740 s.

In one aspect, where no disulfide analysis is performed, the digestion times range from about 0.5 s to about 10 min.

In one aspect, when the protein is denatured, the digestion times are from about 0.5 s to about 10 minutes. In one aspect, the digestion times are about 0.7 s or about 5.7 S.

In one aspect, the PTMs are selected from the group consisting of pyroglutamic acid formation, oxidation, amidation, deamidation, phosphorylation, methylation, acetylation, and glycosylation. In one aspect, additional PTMs are also identified.

In one aspect, the hydrolyzing agent is a protease. In one aspect, the protease is selected from the group consisting of aspergillopepsin I, LysN protease (Lys-N), LysC endoproteinase (Lys-C), endoproteinase Asp-N (Asp-N), endoproteinase Glu-C (Glu-C) and outer membrane protein T (OmpT), or biologically active fragments or homologs thereof. In one aspect, the protease is aspergillopepsin I (SEQ ID NO:32) or a biologically active fragment or homolog thereof.

In one aspect, the adjustable flow rate is selected from a range of about 50 μl/min to about 4.0 μl/min.

In one aspect, when a protein is denatured the protein is reduced and alkylated before dissolving in digestion buffer. In one aspect, the protein is alkylated using N-(2-aminoethyl) maleimide.

In one aspect, the protein is selected from the group consisting of an antibody, an antibody-like molecule, an antibody light chain, an antibody heavy chain, or biologically active fragments and homologs thereof. In one aspect, the antibody is a monoclonal antibody (mAb). In one aspect, the antibody is a therapeutic antibody. In one aspect, more than one protein is characterized.

In one aspect, characterization data is obtained from the LC MS/MS performed on the protein fragments.

In one aspect, the method is performed in a single LC-MS apparatus. In one aspect, the method is performed in a single run. In one aspect, the characterization data include at least 85, 90, 95, or 99% of the protein amino acid sequence. In one aspect, the characterization data include the identities of substantially all of the post-translational modifications of the protein. In one aspect, the characterization data include the locations of substantially all of the post-translational modifications of the protein.

In one aspect, the hydrolyzing agent is immobilized. In one aspect, it is immobilized on an aldehyde-functionalized particle.

In one aspect, a combination of electron transfer dissociation (ETD) and collision activated dissociation mass spectrometry (CAD) tandem mass spectrometry are used to characterize the resulting protein fragments.

In one aspect, the protein is exposed to the hydrolyzing agent at a pH of about 3.0 to about 9.0. In one aspect, the protein is exposed to the hydrolyzing agent at a pH of about 7.0 to about 9.0.

In one embodiment, the present invention provides a reaction chamber useful for the practice of the invention. In one aspect, the reaction chamber is useful for time-controlled digestion and size-controlled digestion of a protein before characterizing the protein using LC MS/MS. In one aspect, the invention provides a reaction chamber comprising at least one immobilized hydrolyzing agent, wherein the protein is passed through the chamber in a digestion buffer at an adjustable flow rate and the protein is present in the chamber for a period of time (t) sufficient to produce protein fragments. In one aspect, digestion of the protein occurs in the chamber. In one aspect, when the fragments of the digested protein exit the chamber, LC MS/MS is performed. In one aspect, the characterization includes, but is not limited, to sequencing amino acids of the protein fragments, determining the protein sequence, identifying post-translational modifications, locating post-translational modifications, identifying disulfide bonds, and locating disulfide bonds.

In one embodiment, the chamber is a fused silica capillary consisting of an outer diameter of 360 μm, an inner diameter of 150 μm, and a length of 8 cm. One of ordinary skill in the art will appreciate that the size can be modified based on parameters such as protein of interest, the amount of protein available, the conditions to be used, the size of fragments to be made, the protease used, etc.

In one aspect, the hydrolyzing agent used in the chamber is aspergillopepsin I or a biologically active fragment or homolog thereof. In one aspect, the hydrolyzing agent is immobilized on beads and the beads are in the chamber.

The present invention further provides a system for characterization a protein. In one embodiment, the system comprises a reaction chamber, a method of preparing the protein for characterization using LC MS/MS, and an LC MS/MS apparatus. In one aspect, the reaction chamber comprises a chamber as set forth in FIG. 6. In one aspect, the chamber comprises at least one immobilized hydrolyzing agent. In one aspect, the method of the system comprises optionally denaturing the protein. In one aspect, the protein is dissolved in a digestion buffer. In one aspect, the dissolved protein in the digestion buffer is passed through the reaction chamber. In one aspect, the protein is present in the chamber for a period of time (t) sufficient to produce protein fragments of a desired size range and digestion of said protein occurs in the chamber. In one aspect, the passing of the digestion buffer comprising the protein through the chamber is done at an adjustable flow rate. In one aspect, once the fragments have exited, multi-segment LC MS/MS is performed on the fragments. In one aspect, the LC MS/MS apparatus is a multi-segment LC MS/MS apparatus.

Sequences Disclosed or Used Herein—

(equine apomyoglobin 114-153)-
SEQ ID NO: 1
VLHSKHPGDFGADAQGAMTKALELFRNDIAAKYKELGFQG (murine L1-52)-
SEQ ID NO: 2
DVLMTQTPLSLPVSLGDQASISCRSSQYIVHSNGNTYLEWYLQKPGQSPK
LL (segment I-3 of mAb digest)-
SEQ ID NO: 3
VEVHTAHTQPREEQFNSTFRSVSELPIMHQDWLNGKEFKCRVN (Lc 53-108)-
SEQ ID NO: 4
IYKVSNRFSGVPDRFSGSGSGTDFTLKISRVEAEDLGVYYCFQGSHVPLT
FGAGTK (apomyoglobin 1-153)-
SEQ ID NO: 5
GLSDGEWQQVLNVWGKVEADIAGHGQEVLIRLFTGHPETLEKFDKFHLK
TEAEMKASEDLKKHGTVVLTALGGILKKKGHHEAELKPLAQSHATKHKIP
IKYLEFISDAIIHVLHSKHPGDFGADAQGAMTKALELFRNDIAAKYKELG
FQG (mouse IgG1 Lc)-
SEQ ID NO: 6
DVLMTQTPLSLPVSLGDQASISCRSSQYIVHSNGNTYLEWYLQKPGQSPK
LLIYKVSNRFSGVPDRFSGSGSGTDFTLKISRVEAEDLGVYYCFQGSHVP
LTFGAGTKLEIKRADAAPTVSTFPPSSEQLTSGGASVVCFLNNFYPKDIN
VKWKIDGSERQNGVLNSWTDQDSKDSTYSMSSTLTLTKDEYERHNSYTCE
ATHKTSTSPIVKSFNRNEC (mouse IgG1 Hc)-
SEQ ID NO: 7
QVQLKESGPGLVAPSQSLSITCTVSGFSLLGYGVNWVRQPPGQGLEWLMG
IWGDGSTDYNSALKSRISITKDNSKSQVFLKMNSLQTDDTAKYYCTRAPY
GKQYFAYWGQGTLVTVSAAKTTPPSVYPLAPGSAAQTNSMVTLGCLVKGY
FPEPVTVTWNSGSLSSGVHTFPAVLQSDLYTLSSSVTVPSSTWPSETVTC
NVAHPASSTKVDKKIVPRDCGCKPCICTVPEVSSVFIFPPKPKDVLTITL
TPKVTCVVVDISKDDPEVQFSWFVDDVEVHTAHTQPREEQFNSTFRSVSE
LPIMHQDWLNGKEFKCRVNSAAFPAPIEKTISKTKGRPKAPQVYTIPPPK
EQMAKDKVSLTCMITDFFPEDITVEWQWNGQPAENYKNTQPIMDTDGSYF
VYSKLNVQKSNWEAGNTFTCSVLHEGLHNHHTEKSLSHSPG (Hc 37-77)-
SEQ ID NO: 8
VRQPPGQGLEWLMGIWGDGSTDYNSALKSRISITKDNSKSQ (L53-110)-
SEQ ID NO: 9
IYKVSNRFSGVPDRFSGSGSGTDFTLKISRVEAEDLGVYYCFQGSHVPLT
FGAGTKLE (L111-148)-
SEQ ID NO: 10
IKRADAAPTVSIFPPSSEQLTSGGASVVCFLNNFYPKD (L149-219)-
SEQ ID NO: 11
INVKWKIDGSERQNGVLNSWTDQDSKDSTYSMSSTLTLTKDEYERHNSYT
CEATHKTSTSPIVKSFNRNEC (H1-36)-
SEQ ID NO: 12
QVQLKESGPGLVAPSQSLSITCTVSGFSLLGYGVNW (H84-148)-
SEQ ID NO: 13
SLQTDDTAKYYCTRAPYGKQYFAYWGQGTLVTVSAAKTTPPSVYPLAPGS
AAQTNSMVTLGCLVK (H149-210)-
SEQ ID NO: 14
GYFPEPVTVTWNSGSLSSGVHTFPAVLQSDLYTLSSSVTVPSSTWPSETV
TCNVAHPASSTK (H211-260)-
SEQ ID NO: 15
VDKKIVPRDCGCKPCICTVPEVSSVFIFPPKPKDVLTITLTPKVTCVVVD (H277-319)-
SEQ ID NO: 16
VEVHTAHTQPREEQFNSTFRSVSELPIMHQDWLNGKEFKCRVN (H320-371)-
SEQ ID NO: 17
SAAFPAPIEKTISKTKGRPKAPQVYTIPPPKEQMAKDKVSLICMITDFFP
ED -continued (H372-441)-
SEQ ID NO: 18
ITVEWQWNGQPAENYKNTQPIMDTDGSYFVYSKLNVQKSNWEAGNTFTCS
VLHEGLHNHHTEKSLSHSPG (Hc84-148)-
SEQ ID NO: 19
SLQTDDTAKYYCTRAPYGKQYFAYWGQGTLVTVSAAKTTPPSVYPLAPGS
AAQTDSMVTLGCLVK (Hc84-184 N for D of SEQ ID NO: 19)-
SEQ ID NO: 20
SLQTDDTAKYYCTRAPYGKQYFAYWGQGTLVTVSAAKTTPPSVYPLAPGS
AAQTNSMVTLGCLVK (Hc358-406)-
SEQ ID NO: 21
VSLTCMITDFFPEDITVEWQWNGQPAENYKNTQPIMDTDGSYFVYSKLN (Hc407-441)-
SEQ ID NO: 22
VQKSNWEAGNIFTCSVLHEGLHNHHTEKSLSHSPG (Hc5-36)-
SEQ ID NO: 23
KESGPGLVAPSQSLSITCTVSGFSLLGYGVNW (Hc93-103)-
SEQ ID NO: 24
YYCTRAPYGKQ (Lc119-148)-
SEQ ID NO: 25
TVSTFPPSSEQLTSGGASVVCFLNNFYPKD (Lc1 91-212)-
SEQ ID NO: 26
YERHNSYTCEATHKTSTSPIVK (Hc125-148)-
SEQ ID NO: 27
SVYPLAPGSAAQTNSMVTLGCLVK (Hc183-210)-
SEQ ID NO: 28
SSSVTVPSSTWPSETVTCNVAHPASSTK (Hc311-319)-
SEQ ID NO: 29
GKEFKCRVN (A chain Lc217-219)-
SEQ ID NO: 30
CVVVD (B chain Hc215-234)-
SEQ ID NO: 31
TVPRDCGCKPCICTVPEVSS (aspergillopepsin I)-
SEQ ID NO: 32
MVVFSKTAALVLGLSTAVSAAPAPTRKGFTINQTARPANKTRTVNLPGLY

ARSLAKFGGTVPQSVKEAASKGSAVTTPQNNDEEYLTPVTVGKSTLHLDF

DTGSADLWVFSDELPSSEQTGHDLYTPSSSATKLSGYSWDISYGDGSSAS

GDVYRDTVTVGGVTTNKQAVEAASKISSEFVQDTANDGLLGLAFSSINTV

QPKAQTTFFDTVKSQLDSPLFAVQLKHDAPGVYDFGYIDDSKYTGSITYT

DADSSQGYWGFSTDGYSIGDGSSSSSGFSAIADTGTTLILLDDEIVSAYY

EQVSGAQESYEAGGYVFSCSTDLPDFTVVIGDYKAVVPGKYINYAPVSTG

SSTCYGGIQSNSGLGLSILGDVFLKSQYVVFNSEGPKLGFAAQA

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4, comprising FIG. 4A to 4E. Identification of disulfide-containing peptide Lc 1-52 (SEQ ID NO:2) & 53-108 (SEQ ID NO:4) by (A) ETD (3 ms), and (B) ETD (3 ms)/IIPT (90 ms) with 15 multi-fills in C-trap, (C), (D), (E).

FIG. 7. Protein Sequence Coverage. Apomyoglobin sequence mapped by ETD (labeled as c and z ions) of five major large peptides, Myo 1-31, 32-69, 70-113, 114-153 and 105-113, generated by size-controlled digestion, with the proteolysis sites labeled by dashed lines between two adjacent amino acids (SEQ ID NO:5).

FIG. 10, comprising FIGS. 10A1, 10A2, and 10B. Base peak chromatograms (A1, A2) of IgGLc and Hc (shaded in grey) with different extent of reduction/alkylation resulting from the following denaturation buffer compositions and denaturing conditions (B).

FIG. 13, comprising FIGS. 13A to 13B. Distributions of the number of peptides (left) and the sequence coverage (right) based on in silico digestion of the IgG used in this work (sequence shown in FIG. 8) by Lys-C (A) and Asp-N (B).

DETAILED DESCRIPTION

Abbreviations and Acronyms

Figure 1A:
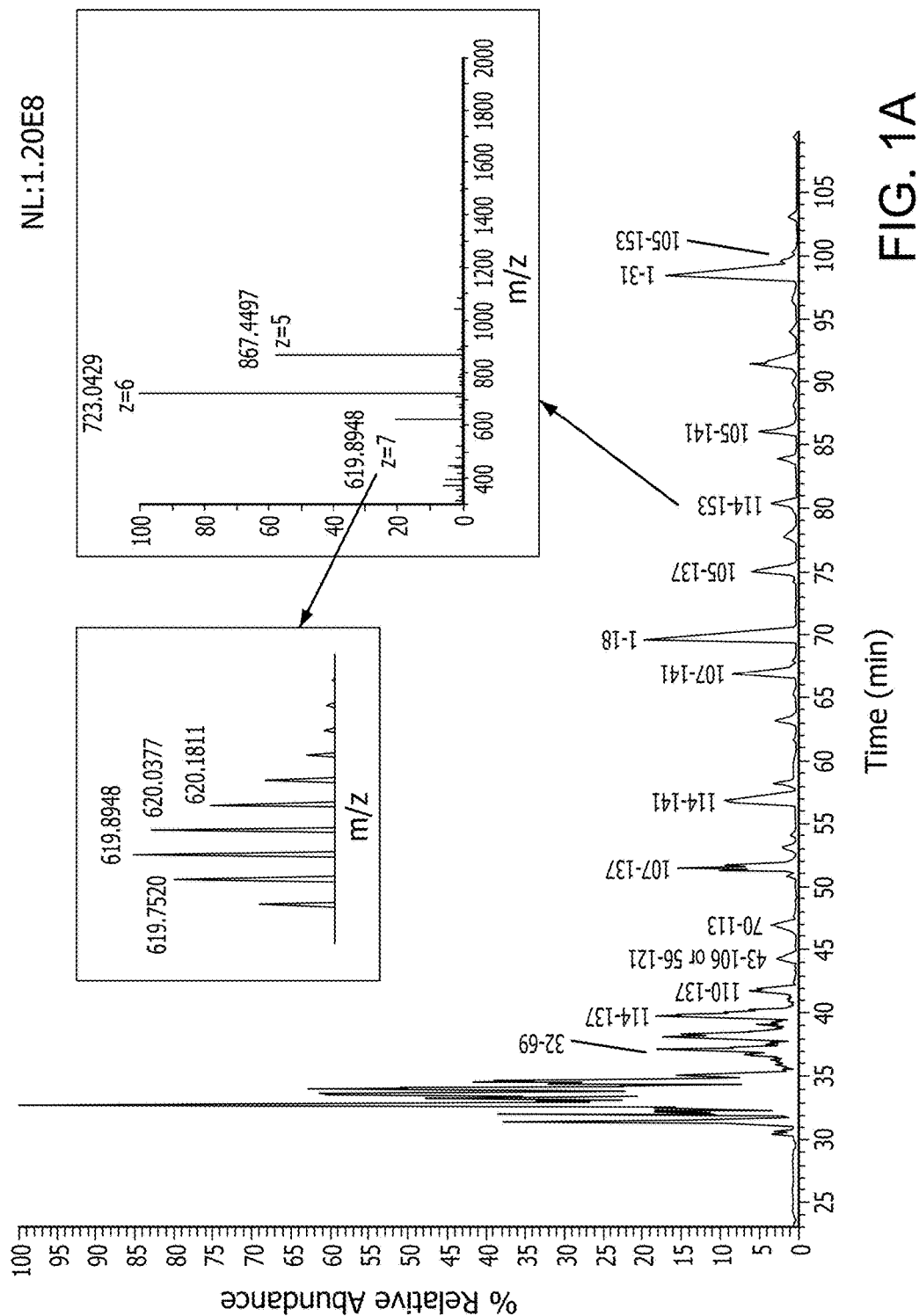
FIG. 1, comprising FIGS. 1A to 1B. (A) Base peak chromatogram of apomyoglobin digest generated by 0.77 s time-controlled digestion, with the 3-8 kDa base peak peptides labeled using apomyoglobin sequence number (identified by MS/MS in Experiment #2). The MS1 spectrum of peptide 114-153 and the isotopic distribution of the +7 ion of this peptide are shown as the arrows indicate. (B) The spectrum of apomyoglobin peptide 114-153 (SEQ ID NO: 1) after converting the original MS2 spectrum to +1 ions by Xcalibur Xtract (some fragment ions lost after Xtract conversion). Under the spectrum is the sequence coverage by c and z. ions assigned by ProSite PC using the original MS2 data (manually verified).
Figure 1B:
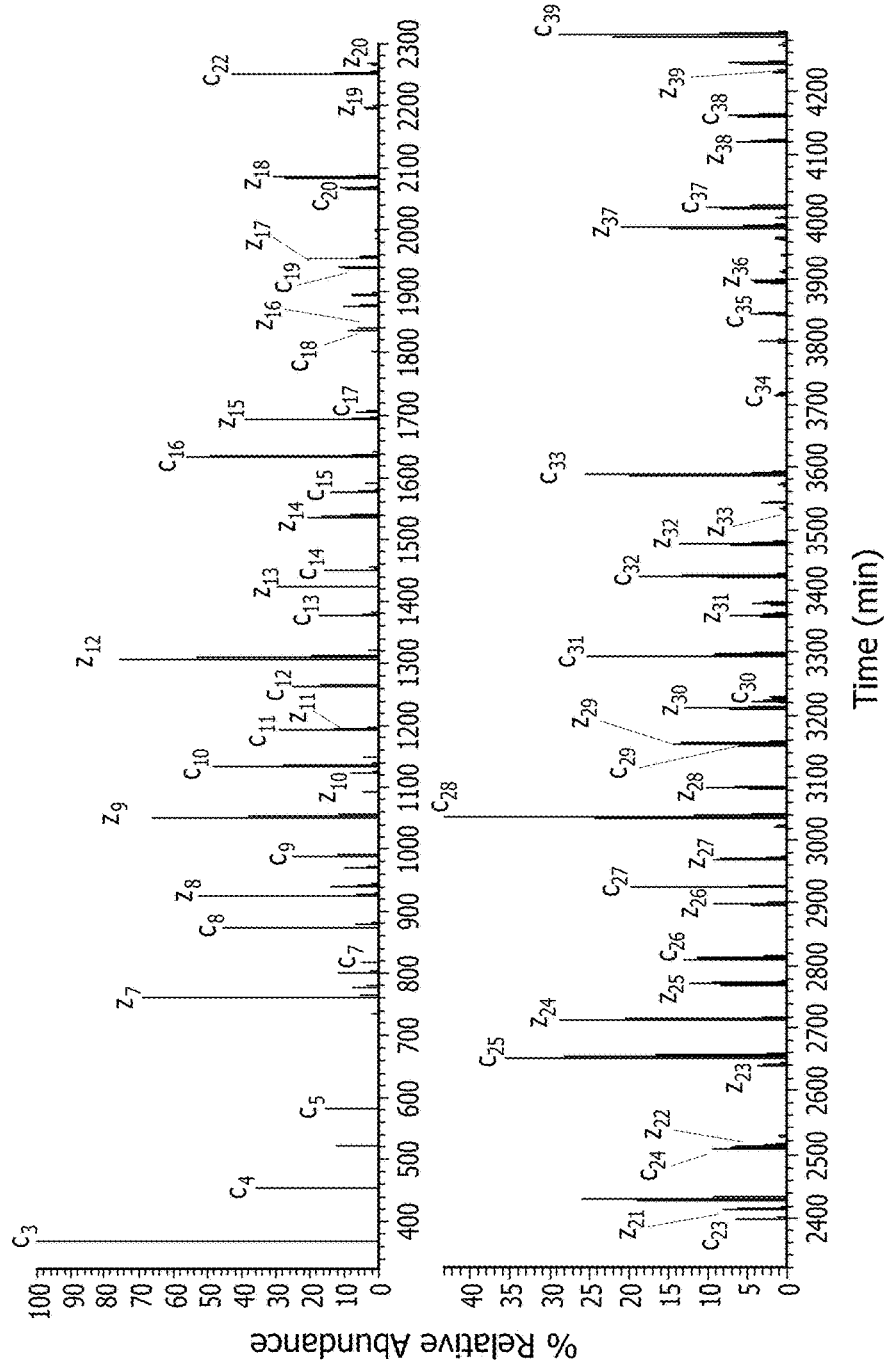

AGC—automated gain control
AspN—AspN endoproteinase (also referred to as flavastacin)
CAD—collision activated dissociation mass spectrometry
CDRs—complementarity-determining regions
cm—centimeter
DTT—dithiothreitol
ESI—electrospray ionization
ETD—electron transfer dissociation
F—force
FETD—front end electron dissociation
FT—fourier transformation
Glu-C—endoproteinase Glu-C
Hc—heavy chain
IAM—iodoacetamide
i.d.—inner diameter
IgG—immunoglobulin G
IIPT—ion-ion proton transfer
kDa—kilodalton
L—length
Lc—light chain
LysC—LysC endoproteinase
LysN—LysN protease
mAb—monoclonal antibody
mM—millimolar
MS—mass spectrometry
MS/MS—tandem mass spectrometry, also referred to as MS2
M.W.—molecular weight
NAEM—N-(2-aminoethyl) maleimide (also referred to as aminoethylmaleimide)
NL—normalized
NP-LC—normal phase liquid chromatography
o.d.—outer diameter
OmpT—outer membrane protein T, a protease formerly referred to as protein a
p—porosity
PTM—post-translational modification
RP-LC—reverse phase liquid chromatography
s—second
S/N—signal to noise
t—residence time
TCEP—tris(2-carboxyethyl)phosphine
TIC—total ion current
V—volume

Definitions

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element or "a protein" means more than one protein.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

As used herein the term, "accurate mass" refers to an experimentally or theoretically determined mass of an ion that is used to determine an elemental formula. For ions containing combinations of the elements C, H, N, O, P, S, and the halogens, with mass less than 200 Unified Atomic Mass Units, a measurement about 5 ppm uncertainty is sufficient to uniquely determine the elemental composition.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

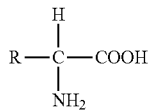

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "biological sample," as used herein, refers to samples obtained from a subject, including, but not limited to, skin, hair, tissue, blood, plasma, cells, sweat and urine.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

As used herein, the term "biologically active fragments" or "bioactive fragment" of the polypeptides encompasses natural or synthetic portions of the full-length protein that are capable of specific binding to their natural ligand or of performing the function of the protein.

A "chaotropic agent" is a substance which disrupts the structure of, and denatures, macromolecules such as proteins and nucleic acids (e.g. DNA and RNA). Chaotropic solutes increase the entropy of the system by interfering with intramolecular interactions mediated by non-covalent forces such as hydrogen bonds, van der Waals forces, and hydrophobic effects. Macromolecular structure and function is dependent on the net effect of these forces (see protein folding), therefore it follows that an increase in chaotropic solutes in a biological system will denature macromolecules, reduce enzymatic activity and induce stress on a cell (i.e., a cell will have to synthesize stress protectants). Tertiary protein folding is dependent on hydrophobic forces from amino acids throughout the sequence of the protein. Chaotropic solutes decrease the net hydrophobic effect of hydrophobic regions because of a disordering of water molecules adjacent to the protein. This solubilizes the hydrophobic region in the solution, thereby denaturing the protein. This is also directly applicable to the hydrophobic region in lipid bilayers; if a critical concentration of a chaotropic solute is reached (in the hydrophobic region of the bilayer) then membrane integrity will be compromised, and the cell will lyse. Chaotropic salts that dissociate in solution exert chaotropic effects via different mechanisms. Whereas chaotropic compounds such as ethanol interfere with non-covalent intramolecular forces as outlined above, salts can have chaotropic properties by shielding charges and preventing the stabilization of salt bridges. Hydrogen bonding is stronger in non-polar media, so salts, which increase the chemical polarity of the solvent, can also destabilize hydrogen bonding. Mechanistically this is because there are insufficient water molecules to effectively solvate the ions. This can result in ion-dipole interactions between the salts and hydrogen bonding species which are more favorable than normal hydrogen bonds. Chaotropic agents include butanol, ethanol, guanidinium chloride, lithium perchlorate, lithium acetate, magnesium chloride, phenol, propanol, sodium dodecyl sulfate, thiourea and urea.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates or carboxylic acids, on the antigen and the carrier molecule. Chemical conjugation also includes non-covalent linkage between the antigen and the carrier molecule.

The term "competitive sequence" refers to a peptide or a modification, fragment, derivative, or homolog thereof that competes with another peptide for its cognate binding site.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:
 I. Small aliphatic, nonpolar or slightly polar residues:
 Ala, Ser, Thr, Pro, Gly;
 II. Polar, negatively charged residues and their amides:
 Asp, Asn, Glu, Gln;
 III. Polar, positively charged residues:
 His, Arg, Lys;
 IV. Large, aliphatic, nonpolar residues:
 Met Leu, Ile, Val, Cys
 V. Large, aromatic residues:
 Phe, Tyr, Trp As used herein, a "derivative" of a compound, when referring to a chemical compound, is one that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains. As used herein, the term "effector domain" refers to a domain capable of directly interacting with an effector molecule, chemical, or structure in the cytoplasm which is capable of regulating a biochemical pathway.

By "equivalent fragment" as used herein when referring to two homologous proteins from different species is meant a fragment comprising the domain or amino acid being described or compared relative to the first protein.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 2-15 amino acids in length, at least about 15-25 amino acids, at least about 25-50 amino acids in length, at least about 50-75 amino acids in length, at least about 75-100 amino acids in length, and greater than 100 amino acids in length, depending on the particular protein or peptide being referred to.

As used herein, a "functional" molecule is a molecule in a form in which it exhibits a property or activity by which it is characterized. A functional enzyme, for example, is one that exhibits the characteristic catalytic activity by which the enzyme is characterized.

"Highly chaotropic environment" refers the concentration of a chaotropic agent in a solution. In certain embodiments, the concentration is exactly, about or at least, 1, 2, 3, 4, 5, 6, 7, 8, 9, 10, or more molar. In a particular embodiment it refers to about or at least 6, 7, 8 or 9 molar urea.

As used herein, "homology" is used synonymously with "identity." The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. The percent identity between two sequences can be determined using techniques similar to those described above, with or without allowing gaps. In calculating percent identity, typically exact matches are counted.

As used herein, the term "hydrolyzing agent" refers to any one or combination of a large number of different enzymes, including but not limited to trypsin, Lysine-C endopeptidase (LysC), arginine-C endopeptidase (ArgC), Asp-N, glutamic acid endopeptidase (GluC) and chymotrypsin, V8 protease and the like, as well as chemicals, such as cyanogen bromide. In the subject invention one or a combination of hydrolyzing agents cleave peptide bonds in a protein or polypeptide, in a sequence-specific manner, generating a predictable collection of shorter peptides (a "digest"). A portion of the biological samples are contacted with hydrolyzing agent(s) to form a digest of the biological sample. Given that the amino acid sequences of certain polypeptides and proteins in biological samples are often known and that the hydrolyzing agent(s) cuts in a sequence-specific manner, the shorter peptides in the digest are generally of a predicable amino acid sequence.

As used herein, an "instructional material" includes a publication, a recording, a diagram, or any other medium of expression which can be used to communicate the usefulness of the compositions and apparatuses of the invention in the kit. The instructional material of the kit of the invention may, for example, be affixed to a container which contains the identified compound(s) invention or be shipped together with a container which contains the identified compound. Alternatively, the instructional material may be shipped separately from the container with the intention that the instructional material and the compound be used cooperatively by the recipient. As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Liquid chromatography-mass spectrometry (LC-MS, or alternatively HPLC-MS)" is an analytical chemistry technique that combines the physical separation capabilities of liquid chromatography (or HPLC) with the mass analysis capabilities of mass spectrometry (MS). Liquid chromatography generally utilizes very small particles packed and operating at relatively high pressure, and is referred to as high performance liquid chromatography (HPLC). LC-MS methods use HPLC instrumentation for sample introduction. In HPLC, the sample is forced by a liquid at high pressure (the mobile phase) through a column that is packed with a stationary phase generally composed of irregularly or spherically shaped particles chosen or derivatized to accomplish particular types of separations. HPLC methods are historically divided into two different sub-classes based on stationary phases and the corresponding required polarity of the mobile phase. Use of octadecylsilyl (C18) and related organic-modified particles as stationary phase with pure or pH-adjusted water-organic mixtures such as water-acetonitrile and water-methanol are used in techniques termed reversed phase liquid chromatography (RP-LC). Use of materials such as silica gel as stationary phase with neat or mixed organic mixtures are used in techniques termed normal phase liquid chromatography (NP-LC).

The term "mass spectrometer" means a device capable of detecting specific molecular species and measuring their accurate masses. The term is meant to include any molecular detector into which a polypeptide or peptide may be eluted for detection and/or characterization. In the preferred MS procedure, a sample, e.g., the elution solution, is loaded onto the MS instrument, and undergoes vaporization. The components of the sample are ionized by one of a variety of methods (e.g., by electrospray ionization or "ESI"), which results in the formation of positively charged particles (ions). The positive ions are then accelerated by a magnetic field. The computation of the mass-to-charge ratio of the particles is based on the details of motion of the ions as they transit through electromagnetic fields, and detection of the ions. In one aspect, the mass measurement error of a mass spectrometer of the invention is about 10 ppm or less, in another it is about 7 ppm or less, and in yet another it is about 5 ppm or less. Fragment ions in the MS/MS and MS3 spectra are generally highly specific for peptides of interest.

The term "peptide" typically refers to short polypeptides.

The term "per application" as used herein refers to administration of a compositions, drug, or compound to a subject.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, a standard can be a known standard agent or compound which is administered or added to a control sample and used for comparing results when measuring said compound in a test sample. In one aspect, the standard compound is added or prepared at an amount or concentration that is equivalent to a normal value for that compound in a normal subject. Standard can also refer to an "internal standard," such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

As used herein, a "substantially homologous amino acid sequence" includes those amino acid sequences which have at least about 95% homology, preferably at least about 96% homology, more preferably at least about 97% homology, even more preferably at least about 98% homology, and most preferably at least about 99% homology to an amino acid sequence of a reference sequence. Amino acid sequences similarity or identity can be computed using, for example, the BLASTP and TBLASTN programs which employ the BLAST (basic local alignment search tool) algorithm. The default setting used for these programs are suitable for identifying substantially similar amino acid sequences for purposes of the present invention.

"Substantially identical" when referring to a subject protein or polypeptide relative to a reference protein or polypeptide (e.g., an enzyme such as aspergillopepsin I or a enzymatically active fragment thereof) means that the subject is either exactly, at least or about 99.9, 99.5, 99, 98, 97, 96, 95, 94, 93, 92, 91, 90, 89, 88, 87, 86, 85, 84, 83, 82, 81, 80, 75, 70, 65 or 60 percent identical in terms of amino acid sequence relative to the reference.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

Embodiments—

The demands for characterization of therapeutic mAbs are increasing with the rapid development of mAb-based pharmaceuticals. MS is the most powerful techniques for the structural characterization of therapeutic mAbs due to its high accuracy, resolution, and speed over other analytical techniques.

The basic antibody structural unit is known to comprise a tetramer. Each tetramer is composed of two identical pairs of polypeptide chains, each pair having one "light" (about 25 kDa) and one "heavy" chain (about 50-70 kDa). The carboxy-terminal portion of each chain preferably defines a constant region primarily responsible for effector function.

Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, Fundamental Immunology Ch. 7 (Paul, W., ed., 2nd ed. Raven Press, N.Y. (1989)) (incorporated by reference in its entirety for all purposes). The variable regions of each light ("VL")/heavy chain ("VH") pair preferably form the antibody binding site. Thus, an intact IgG antibody has two binding sites. Except in bifunctional or bispecific antibodies, the two binding sites are the same. The chains all exhibit the same general structure of relatively conserved framework regions (FR) joined by three hyper variable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, J. Mol. Biol. 196:901-917 (1987); Chothia et al., Nature 342:878-883 (1989).

Examples of molecules which are described by the term "antibody" herein include, but are not limited to: single chain Fvs (scFvs), Fab fragments, Fab' fragments, F(ab') 2, disulfide linked Fvs (sdFvs), Fvs, and fragments thereof comprising or alternatively consisting of, either a VL or a VH domain. The term "single chain Fv" or "scFv" as used herein refers to a polypeptide comprising a VL domain of antibody linked to a VH domain of an antibody. As such, the term antibody encompasses not only whole antibody molecules, but also antibody multimers and antibody fragments, as well as variants (including derivatives) of antibodies, antibody multimers, and antibody fragments. Included in the term are T cell receptors, single chain Fvs (scFvs), Fab fragments, Fab' fragments, F(ab') 2, disulfide linked Fvs (sdFvs), Fvs, and fragments thereof. One of ordinary skill in the art will appreciate that the compositions and methods of the invention can be applied that this approach can easily be applied to the characterization of antibody drug conjugates, (ADCs), antibody biosimilars, chimeric antigen receptors (CARs), and antigen T-cell receptors.

Sample proteins, e.g. antibodies and/or antibody like molecules or other proteins, which may be suitable for analysis in the methods, system, and apparatus of the invention include those which are about or less than 500, 400, 300, 200, 150, 100, 75, 50, 25, 10 or 5 kDa in mass. In one aspect, the protein is a membrane protein.

The present application discloses a method of characterizing a protein in a sample. In one aspect, the protein is first denatured. In one aspect, the denatured protein is reduced and alkylated. In one aspect, the denatured protein is passed through an enzyme reaction chamber, also referred to herein as an enzyme reactor or reaction chamber for a selected period of digestion time, in order for the protein to be exposed in a time-controlled manner to the hydrolyzing agent. Digestion times can vary depending on several conditions and parameters and whether a disulfide analysis is to be performed. Digestions times for sequencing can include, for example, 0.7 s and 5.7 s. Digestion times for disulfide analysis are longer when the same protein is to be analyzed and can be, for example, 12 s, 93 s, 260 s, and 740 s. One of ordinary skill in the art can determine the digestion times (times in the column/reactor) based on factors such as the protein being characterized, the hydrolyzing agent being used, the buffer being used, the chaotropic agent being used, the length and diameter of the column/chamber and can use the three Equations provided herein to aid in the process.

In one aspect, the protein is exposed to the hydrolyzing agent under acidic and highly chaotropic conditions to obtain peptides (fragments) from the protein. Then mass spectroscopy is performed on the peptides to obtain characterization data. In one aspect, the method is performed in a single LC-MS apparatus. In one aspect, the method is performed in a single run. In one aspect, the characterization data comprises at least 85, 90, 95, 99% of the protein amino acid sequence. In one aspect, the characterization data comprises the identity and/or location of substantially all of the protein's post-translational modifications.

In one embodiment, the protein is selected from the group consisting of an antibody, an antibody-like molecule, an antibody light chain, and antibody heavy chain, or biologically active fragments and homologs thereof.

In one embodiment, the hydrolyzing agent is aspergillopepsin I enzyme or a biologically active fragment or homolog thereof, or a substantially identical enzyme having aspergillopepsin I enzyme activity.

In one embodiment, the time of passage through the column is about, at least or exactly 1, 2, 3, 5, 6, 7, 8, 9, 10 milliseconds, seconds or minutes.

In one embodiment the highly chaotropic conditions include about 6 to about 9 Molar urea. In one aspect, it includes at least or about 6, 7, or 8 Molar urea. In one aspect, the condition comprises 8M urea.

As a "compromise" between the bottom-up and top-down approaches, "middle-down" analysis has drawn increasing interest. This concept inherits some of the advantages of intact protein MS analysis, but has lower instrumental requirements (e.g. sensitivity, resolution) in achieving sufficient signal-to-noise ratio (S/N) of fragment ions for protein sequencing. Middle-down protein analysis typically involves protein digestion using proteases or chemicals that cleave proteins at single type of amino acid residue to generate peptides generally larger than 3 kDa. Frequently used tools include Lys-C (cleaves at C-terminal size of Lys), Asp-N (cleaves at N-terminal side of Asp), and Glu-C (cleaves at C-terminal side of Glu). High concentrations of formic acid and acetic acid with assistance of microwave radiation have also been employed to cleave C-terminal side of Asp. Some dibasic-site specific proteases are also reported to create even larger peptides (Tsybin et al., J. Proteome Res. 2013, 12, 5558-5569).

Compared to small tryptic peptides, medium or large peptides generally reveal more information of protein isoforms, variants, and combinatorial PTMs. They have fewer source protein candidates in protein databases, leading to higher protein identification confidence by database search. In the aspect of MS analysis, larger peptides tend to have a higher number of basic amino acid residues, which facilitates peptide sequencing by ETD or ECD. Recent studies have shown the power of middle-down approach in characterization of histone PTMs as well as other proteins.

However, the limitations of currently available tools for middle-down protein analysis are also substantial. For example, none of the twenty amino acids are evenly distributed along protein chains. Protein digestion at single-type amino acid sites still produces many small (<3000 Da) or ultra large (>15 kDa) peptides. Identification/characterization of proteins based on these peptides cannot take advantage of middle-down approach (Tsybin et al., J. Proteome Res., 2013, 12, 5558-5569). Additionally, the enzymatic digestion efficiency is often low for proteins with highly folded structure or low solubility.

Although high concentrations of chaotropic agents such as 8M urea are often used to unfold proteins during protein reduction and alkylation, direct protein digestion in this condition quickly deactivates commonly used enzymes. Moreover, normal online data-dependent MS/MS analyses adopt a single MS2 setting (often with unit mass resolution) for dissociation of several most abundant ions regardless of their charge states. Uniform setting is incompatible with electron-based dissociation of large peptides with a diverse charge state distribution. Compared to small peptides, large peptides are often highly charged and require tailored parameters for electron-based dissociation to achieve optimal fragmentation. In addition, large peptides require averaging high-resolution MS2 scans, which results in extended duty cycle, to compensate for decreased fragment signals due to more fragmentation channels.

For example, in one embodiment, to hydrolyze a 150 kDa mAb into mainly 3-10 kDa peptide fragments for MS analysis, an enzyme reactor was prepared by packing a capillary column with 20 µm beads coated with aspergillopepsin I that had been covalently immobilized to the beads (see Examples). Precise control of the sample flow rate as the sample passed through the column lead to determined residence time of the substrate protein in the reactor. A short residence time (t) results in a few cuts along the protein chain and ultimately the formation of large peptides (FIG. 5), and it is disclosed as useful for time-controlled digestion of originally highly folded mAb. The Bruening group first demonstrated this "time-control" concept using a nylon membrane electrostatically adsorbed with pepsin or trypsin with polystyrene sulfonate as a medium layer (15). Pushing the protein through the membrane-based enzyme reactor in <1 s breaks the protein into large peptides that facilitate mapping the sequence of apomyoglobin (17 kDa) and bovine serum albumin (66 kDa) by infusion electrospray ionization (ESI) MS.

Aspergillopepsin I, also known as protease type XIII, generally catalyzes the hydrolysis of substrate proteins in P1 and P1' of hydrophobic residues, but also accepts Lys in P1. The novelty of this work and the rationale of using immobilized aspergillopepsin I for time-controlled digestion lie in that:

1) aspergillopepsin I has sustained activity in 8M urea at pH ~4. This extreme chaotropic condition may disrupt the higher-order structure of proteins to the most extent and allows for easy access of the protease to most regions of the substrate protein;

2) the broad protease specificity allows for near random chance of enzymatic cleavage along the unfolded protein chain; and 3) in-tube digestion by free aspergillopepsin I is difficult to quench due to the sustained activity of the protease in broad pH range. The enzyme reactor however automatically "quenches" proteolysis as the sample flows out of the column.

The features of immobilized aspergillopepsin I described above and in the Examples, along with the time-controlled digestion mode, resulted in the generation of mainly 3-10 kDa highly charged large peptides that facilitate online ETD MS/MS analysis. Also disclosed herein is alkylation of mAb Cys residues with a new reagent, N-(2-aminoethyl)maleimide (NAEM), prior to digestion. This new alkylation reagent improves ETD characterization of mAb peptides by adding additional basic groups to Cys. Selecting the most abundant ~40 large peptides for online MS/MS revealed near complete sequence of mAb and multiple PTMs. Native mAb was also digested using this concept. ETD/ion-ion proton transfer (IIPT) of the disulfide-containing peptides quickly identified their N- and C-terminal sequences and localized the disulfide(s) within/connecting different mAb domains.

In one embodiment, digestion of a protein with a hydrolyzing agent results in about 2 to about 20 fragments. In one aspect, it generates about 5 to about 15 fragments. In another aspect, it generates about 10 fragments. One of ordinary skill in the art will appreciate that the number of fragments refers to fragments with strong signals/high abundance, so the numbers referred might also be construed to be major fragments.

In one embodiment, the present invention provides a liquid chromatography mass spectrometer system, method, and apparatus useful for rapid protein sequence analysis and detection of post-translational modifications. In one aspect, the apparatus comprises an immobilized hydrolyzing agent. In one aspect, the agent is immobilized to an aldehyde-functionalized particle. In one aspect, the agent is a protease. In one aspect, the system comprises an adjustable flow rate.

In one aspect, the system is capable of analyzing a protein sample. In one aspect, the system comprises an immobilized hydrolyzing agent, wherein the hydrolyzing reagent is selected from the group consisting of: aspergillopepsin I or a biologically active fragment or homolog thereof; a protease substantially identical to aspergillopepsin I or a biologically active fragment thereof of the protease; and a protease that is capable of hydrolyzing the protein sample under acidic and highly chaotropic conditions to generate peptides in the range of about 3 to about 10 kDa in mass. In one aspect, the range is about 4 to about 9 kDa in mass. In another aspect, the range is about 5 to about 8 kDa in mass. In another aspect, the range is from about 6 to about 7 kDa in mass. In one aspect, the hydrolyzing agent is aspergillopepsin I. In one aspect, the hydrolyzing agent is immobilized on beads within a flow through column. In one aspect, the highly chaotropic conditions consist of 8M urea. In one aspect, the protein sample is an antibody sample. In one aspect, the protein sample comprises a protein of about 150 kDa in mass. In one aspect, the pH is about 3.5 to about 4.0.

In one embodiment, urea is used as a chaotropic agent. In one aspect, it is effective at a pH range of about 3.0 to about 5.0. In one aspect, it is about 3.5 to about 4.0.

In one aspect, protein denaturation is done in the absence of urea, and is done instead at high heat at temperatures up to about 100° C. In one aspect, the digestion buffer comprises 0.5% acetic acid at temperatures up to about 100° C.

In one aspect, a protease other than aspergillopepsin is used. In one aspect, a protease that is active under weak basic conditions (e.g., pH 8-9) can be used. In one aspect, an acid-cleavable surfactant, such as RapiGest, can be used to improve protein denaturation and digestion under weak basic conditions. Then, following digestion, acid can be added to the sample to degrade the surfactant so that the surfactant does not affect LC MS analysis. Proteases that work at ph 8-9 include Lys-C, Lys-N, Asp-N, and Glu-C. Additionally, if one of these proteases, such as Lys-N were immobilized into the column/reactor of the invention, high temperatures of about 70° C. can be used or buffers containing 50% acetonitrile can be used to improved protein denaturation.

In one embodiment, the invention comprises using time limited proteolysis (i.e., digestion) to produce 3-10 kDa fragments and a combination of ETD and CAD tandem mass spectrometry to characterize the resulting peptides.

In one embodiment, the present invention provides compositions and methods that disrupt the limitation in the art of conventional in-solution protein digestion that solely relies on enzyme specificity and extends the digestion condition to 8M urea that favors unfolding of many compact proteins. In addition, the employment of aminoethylmaleimide as a new Cys alkylating reagent enhances the charge states of peptides containing Cys and improved ETD MS2. This strategy shows superior ability in digesting mAb into 3-10 kDa peptides compared to in-solution digestion by LysC and AspN, and yields 98% sequence coverage for mAb LC (25 kDa) and 94% for mAb HC (50 kDa). Moreover, PTMs on mAbs including pyroglutamic acid formation, oxidation, amidation, and glycation have been identified using this novel method.

Other proteases can be used to practice the invention, such as in the context of micro-column enzyme reactors for generating large protein fragments (Switzar et al., Protein Digestion: An Overview of the Available Techniques and Recent Developments, J Proteome Res 2013; 12:1067-1077). Other useful proteases (specificities) include: Lys-N (n-terminal of Lys); Lys-C (c-terminal to Lys); and OmpT (between two consecutive basic residues Lys/Arg-Lys/Arg). Lys C works in 8M urea (Choksawangkarn et al., Enrichment of Plasma Membrane Proteins Using Nanoparticle Pellicles: Comparison Between Silica and Higher Density Nanoparticles, J Proteome Res 2013; 12:1134-1141). Lys-N works in both 8M urea and 80% acetonitrile (Taoutas et al., Evaluation of Metalloenopeptidase Lys-N Protease Performance Under Different Sample Handling Conditions, J Proteome Res 2010; 9(8):4282-4288) and OmpT has been shown to cleave proteins into 6 kDa fragments (Wu et al., A Protease for 'Middle-down' Proteomics, Nat Methods 2012; 9(8):822-824).

It is disclosed herein that Lys-N digests proteins under harsh conditions that improved protein solubility or denaturation, including 8M urea, 70° C., and buffer containing 50% acetonitrile (data not shown).

The present application discloses an apparatus to practice the methods of the invention. Disclosed herein are MS apparatuses and strategies which utilize an immobilized hydrolyzing agent, e.g., an aspergillopepsin I enzyme, an enzymatically active fragment thereof, or a polypeptide substantially identical to any of the foregoing, with broad specificity and consistent activity in highly chaotropic environment, (e.g. 6-10M urea), to digest denatured proteins into large peptides via a size-control mode. Selecting a proper flow rate as the protein sample passes through the protease column precisely controls digestion time.

In one embodiment, the methods of the invention generate mainly medium size peptides of about 3 to about 10 kDa. In another embodiment, the methods of the invention can be used to generate peptides of about 10 to about 20 kDa. In yet another embodiment, the methods of the invention can be used to generate ultra-large size peptides of about 20 to about 50 kDa. This includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, and 50, and all numbers and fractions subsumed within that range.

In one embodiment, the methods disclosed herein generate mainly peptides in size ranges of about 1-20, 2-15, 3-12, 3-10, 3-9 or 3-8 kDa, and includes all numbers and fractions subsumed within that range, from proteins such as mAbs. Peptides in this size range are favorable for protein sequencing when coupled with online LC-ETD MS/MS. In another embodiment, the employment of an alkylating agent (e.g., NAEM as a new Cys alkylating reagent disclosed herein) improves ETD of peptides containing complementary determining regions (CDRs) by enhancing the peptide charge state.

In another embodiment, the methods and apparatuses described herein can be used in conjunction with a multi-segment online LC-MS/MS strategy, allow for the sequencing of a 150 kDa protein such as an mAb with 98% sequence coverage on the light chain and 94% sequence coverage on the heavy chain. In another embodiment, the methods and apparatuses described herein allow for the identification of multiple PTMs on proteins, such as mAbs, including, but not limited to, pyroglutamic acid formation, oxidation, amidation, deamidation, phosphorylation, methylation, acetylation, and glycosylation. One of ordinary skill in the art will appreciate that many PTMS can be identified and localized using the compositions and methods of the invention. In one aspect, a PTM that is stable at about pH 3-4 is detected. Additionally, most PTMs that have been found in the art using LC MS should be applicable to the present methods because the present method encompasses a pH similar to that used for LC-MS.

Another embodiment involves an apparatus and method for rapid amino acid sequence analysis and characterization of large proteins such as antibodies or antibody-like molecules, membrane proteins, or large fragments of such proteins at the low picomole level. The method involves: 1) reduction, alkylation and digestion of the protein sample while it is fully denatured in a solution that is highly chaotropic, e.g., 8M in urea; 2) choosing a protease that functions under acidic conditions (e.g., a pH 3.9) and is that is not denatured in 8M urea; (3) a flow-thru reactor constructed from 360 micrometer o.d.×150 micrometer i.d. fused silica capillary equipped with a 2 mm Kasil frit and packed with POROS 20 beads covalently linked to the protease, aspergillopepsin 1; (4) generation of peptide fragments in the 3-15 kDa mass range by control the sample flow rate through, and thus sample residency time (about 1-6 seconds) in, the capillary reactor; and (5) amino acid sequence analysis of the resulting fragments by nanoflow-HPLC interfaced to electrospray ionization on a tandem high resolution mass spectrometer equipped for both collision activated dissociation and electron transfer-dissociation.

The present application discloses how to calculate flow rates and determine digestion times. For example, one flow rate range of the invention is based on an 8-cm long enzyme reactor, and this range is proportional (has a linear relationship) to the length of the enzyme reactor. One of ordinary skill in the art will understand that the linear relationship can be used to make the calculations necessary when digesting a protein.

At least two factors can affect desired sample flow rate: IgG concentration (or other test protein) and the length of packed enzyme reactor. To produce peptides with a desired size range (i.e. medium size 3 to 10 kDa) using a given enzyme reactor column, lower protein concentration requires a higher flow rate (i.e. less digestion time) (data now shown). For example if 0.2 mg/mL (i.e. 1.35 pmol/microliter) IgG were being used, the factor that controls the general size of final peptides is the digestion time. In one aspect, to achieve an optimal peptide size range of about 3 kDa to about 10 kDa, include all numbers and fractions subsumed within that range, one would need 5.7 sec digestion time, which is realized by flowing the sample at 4.5 microliter/min through an 8-cm long enzyme reactor. However, if an enzyme reactor longer than 8 cm is used, the sample will need to flow through the column faster in order to achieve a 5.7 s digestion time.

Additionally, if a protein at a concentration of 0.2 mg/ml, such as alkylated IgG, were subjected to flow through a 8 cm long enzyme reactor, and in an effort to create IgG peptides with a size ranging from medium size (i.e. 3 k-10 kDa) to ultra-large size (i.e. 20-50 kDa), the digestion time would probably range from about 0.5 s to about 6 s. To realize this, the corresponding flow rate should be adjustable in the range of about 50 to about 4.0 µl/min. Flow rate can be calculated using Equation (3).

It is disclosed herein that the invention does not require that a column be packed exactly at 8 cm every time. According to Equation (3), to achieve a certain digestion time, one can select the flow rate based on the actual length of packed enzyme reactor. This technique provides an advantage over the art. For example, if one would like to repeat the digestion with a certain digestion time (e.g. 5.7 s), one does not need to pack a new column with exactly the same enzyme reactor length as the previous column, which is not practical. Therefore, if the new column is half the length of the previous column, the flow rate should also drop to half in order to achieve the same digestion time.

In one aspect, the units for describing flow rate are µL/min. These units were used to determine the flow rate using a 5 or 10 µL calibrated pipette by collecting a certain volume of liquid flowing out of the column in 1 minute or half a minute and calculating the flow rate.

The present invention provides an apparatus and a method for sequencing proteins and detecting post-translational modifications. In one aspect, a rapid method for sequence analysis of proteins of about 150 kDa is provided. In one aspect, a protein of interest is denatured and then digested. In one aspect, the protein is digested in urea. In one aspect, the urea is used at a pH of about 4.0. In one aspect, the concentration of urea is about 8M. In one aspect, the digestion is controlled by passing the protein sample in urea through a column comprising an immobilized protease using a precisely controlled digestion time. In one aspect, the method generates fragments of about 3-9 kDa.

The invention further provides steps of denaturing proteins.

In one aspect, the flow rate is measured and adjusted by tuning the pressure applied to the column.

In one aspect, the invention is useful for disulfide bond localization. In one aspect, the protein digestion time is increased to enhance disulfide bond localization.

In one aspect, the alkylating agent is NAEM.

The amount of time for protein digestion can be varied to achieve different results as to disulfide bond localization. In one aspect, longer digestion times are required to locate disulfide bonds.

In one embodiment, a protein to be sequenced is denatured and then digested. In one aspect, the protein is an antibody. In one aspect, the antibody is a monoclonal antibody. In one aspect the denatured proteins are reduced and alkylated. In one aspect, the proteins are fully denatured.

In one aspect, disulfides of a protein are reduced with tris(2-carboxyethyl)phosphine (TCEP). In one aspect, the protein comprising reduced disulfides is alkylated. In one aspect, the alkylating agent is NAEM. In one aspect, the alkylated protein is diluted to about 0.2 µg/µL with urea. In one aspect, the urea is used at about 8M and a final pH of 3.90. This solution is then used for on-column digestion of the protein. The protein is then subjected to size-controlled proteolysis by passing the sample through the column at a flow rate that is adjustable.

In one aspect, the digestion buffer comprises urea. In one aspect, urea is used at 8M. In one aspect, the pH of the buffer is about 3.9.

The invention provides an enzyme reactor, also referred to as a chamber. In one aspect, the enzyme reactor comprises a protease that has been immobilized. In one aspect, a column is prepared comprising immobilized protease. In one aspect, the enzyme is a hydrolytic enzyme. In one aspect, the enzyme is a protease. In one aspect, the protease has broad specificity. In one aspect, the protease with broad specificity is aspergillopepsin I.

In view of the structural/functional information available about aspergillopepsin I protein, one of skill in the art would be able to determine which fragments of the protein would be capable of being cleaved at hydrophobic residues in P1 and P1', but also accepting Lys in P1 under highly chaotropic conditions. This is referred to herein as "aspergillopepsin I" activity.

In one aspect, aspergillopepsin I is immobilized on aldehyde-functionalized particles by reductive amination under "salting out" conditions. In one aspect, the aldehyde-functionalized particles are 20 µM particles. In one aspect, the enzyme modified particles are suspended in water and packed into a fused silica capillary to form an enzyme reactor. In one aspect, the fused silica capillary is 360 µM o.d.×150 µM i.d. In one aspect, the enzyme reactor can be from about 1 to about 15 cm long. In another aspect, the reactor is from about 2 to about 14 cm long. In one aspect, the reactor is about 8 cm long. One of ordinary skill in the art can readily determine the size of the reactor needed based on the methods disclosed herein.

The flow rate can be adjusted based on the time needed for digestion to occur. Factors to be considered include, for example, the length of the column or chamber or vessel being used, the inner diameter of the column, the length of the column, the volume of the column, the amount of hydrolyzing agent that is immobilized, the amount of protein to be passed through the column, the amount time that the protein should be in contact with the hydrolyzing agent, the particular hydrolyzing agent being used, the size of the protein or polypeptide being digested and the size of the peptides desired for analysis of the sequence, PTMs, or disulfide bond localization.

For disulfide bond location, a native mAb or another protein of interest can be subjected to the same procedure but with longer digestion times controlled by sample flow rate through the micro column reactor. Release of disulfide containing peptides from accessible regions of the folded protein occurs with short digestion times. The identity of two peptides connected by a disulfide bond is determined using a combination of ETD and ion-ion proton transfer chemistry to read the two N-terminal and two C-terminal sequences of the connected peptides. (See: (1) Protein Identification Using Sequential Ion/Ion Reactions and Tandem Mass Spectrometry, Coon J J, Ueberheide B, Syka J E P, Dryhurst D D, Ausio J, Shabanowitz J, Hunt D F, Proc Natl Acad Sci USA, 2005 Jul. 5; 102(27):9463-8. PMCID: PMC1172258 (2) Analysis of Intact Proteins on a Chromatographic Time Scale by Electron Transfer Dissociation Tandem Mass Spectrometry, Chi A, Bai D L, Geer L Y, Shabanowitz J, Hunt D F, Int. J. Mass Spectrom., 2007, 259, 197-203. PMCID: PMC1826913 (3) Protein Derivatization and Sequential Ion-Ion Reactions to Enhance Sequence Coverage Produced by Electron Transfer Dissociation Mass Spectrometry, Anderson L C, English A M, Wang W-H, Bai D L, Shabanowitz J, and Hunt D F, Int J Mass Spectrom 2014, DOI: 10.1016/j.ijms.2014.06.023).

In one embodiment, more than one protease is used.

In one aspect, the digestion occurs while the solution comprising the protein passes through the column.

In one aspect, the digested peptides are less than about 10 kDa and greater than about 3 kDa or less than about 20 kDa and greater than about 10 kDa or less than about 50 kDa and greater than about 20 kDa.

In one aspect, PTMs are selected from the group consisting of pyroglutamic acid formation, oxidation, amidation, and glycosylation.

In one aspect, the protease is selected from the group consisting of a aspergillopepsin I, LysN protease (Lys-N), LysC endoproteinase (Lys-C), endoproteinase Asp-N (Asp-N), endoproteinase Glu-C (Glu-C) and outer membrane protein T (OmpT).

The present invention provides advantages over current methods in the art. For example, the in-tube digestion method in the art mixes target proteins (e.g. IgG) with a protease in a ~1:20 mass/mass ratio. However, the in-tube digestion has drawbacks. Using the in-tube method it would be difficult to quench a digestion that utilizes aspergillopepsin I as the protease. This is because the digestion is active at pH 3-4, which is also the condition for the following LC-MS analysis after digestion. For in-tube digestion, one has to load the digest sample to the HPLC column while the digestion is still going on. If, for example, one were to perform a 20 min in-tube digestion for IgG, then one would need at least 5 min to load the digest onto the column, and this 5 min adds 25% error to the digestion time. Then, another 10 min is required for column washing. This can add another 50% error to digestion time. Adding together the total digestion time error could be 75%.

In contrast, the on-column digestion mode as disclosed herein quenches the digestion easily and the sample protein stops digestion immediately after it flows out of the enzyme reactor. This allows for accurate control of the flow rate (error within 5%) and for accurate control of the digestion time (error is also 5%). which directly leads to the size of the final peptides. Another embodiment includes using a syringe pump to push the protein sample through the column, which provides even more stable flow rate (flow rate error could be <1%; data not shown).

The present application discloses the use of both "time-controlled" and "size-controlled" digestion which is done rapidly in the enzyme reactor/chamber as described herein. However, the present invention provides other advantages over the art as well. In fact, using the present compositions, methods, system, and apparatus as described herein, the amount of time for the entire procedure for prepping a protein, digesting it, running it through the reactor, and having a sample ready for LC MS analysis is greatly reduced. Because the digestion time is so fast and the samples can be stored and are re-useable, the methods provide additional advantages. For example, a set up and run procedure to obtain digested protein may take only 45 minutes once the column/enzyme reactor is prepared. Once the column/enzyme reactor chamber is prepared, a test of sample flow rate is performed using a "blank" solution which contains only the buffer used to prepare the IgG sample. Then the bomb pressure can be adjusted to achieve the desired flow rate. This step takes 5-10 min. Then, the protein (e.g., IgG) sample is passed through the column using the same bomb pressure, and it flows with very similar (sometimes ~10% lower but still stable) flow rate as for the "blank" test. Typically, the first ~10 microliter of solution flowing-out is discarded as it contains buffer or diluted IgG digest from the dead volume of the column. Then up to 20 microliter digest sample is collected. The total time for processing the sample through the column and collecting the digested protein may be up to about ten minutes. Also, there may be a need to collect 3 digest samples that correspond to 3 different digestion time (i.e. 3 different flow rates), which would yield peptides with medium, large, and ultra large sizes, and if that is done then the entire process from beginning to end may take only up to 45 minutes. Further advantages of this procedure over in-tube collection are provided below.

Contrary to the in-chamber (column) digestion procedure and apparatus disclosed herein, for in-tube digestion each digestion takes 10-30 min depending on the peptide size desired. To obtain three different IgG digest samples that yield peptides from medium size to ultra large size, it would take at least 1 hr because the 3 digestions cannot be done in parallel as you have to do one digestion and run the sample immediately, then later do another digestion, and so on. It should also emphasize that, each in-tube digestion allows only a single LC MS analysis because the digestion is continuous after an aliquot of the digest sample is loaded to the HPLC for LC MS analysis. The rest of the IgG digest must be discarded after sample loading. In contrast, the presently disclosed method creates digest samples that can be stored and reusable (up to 20 times LC MS analyses for a 20 μL digest sample). Considering all the above factors, the following estimation is provided:

Therefore, for a given new protein sample (such as IgG), in one aspect it is desirable to create three digest samples that correspond to three peptide size classes: medium size (3-10 kDa), large size (10-20 kDa) and ultra-large size (20-50 kDa). With the on-column digestion system disclosed herein, only 45 min is required for preparation of the sample and its digestion, and the samples obtained after passing through the column provide enough material for up to 20 times LC-MS analysis/sample. However, using the in-tube digestion known in the art, the procedure may allow up to 5 LC MS analyses/sample, and this will require three separate procedures (at least 1 hr×3×5=15 hrs total time for in-tube digestions) for a total of 15 hours. Based on this comparison and the results described herein, the present method is referred to as "rapid" relative to other methods and apparatuses used in the art for the characterization of proteins.

Although some proteins can be denatured for the most desirable result using the methods of the invention, the invention also encompasses the use of proteins that are not denatured before being dissolved in a digestion buffer of the invention. For example, one of the purposes of denaturing a protein as disclosed herein is to cause the molecule to be as linear as possible, so that the chances of digesting different regions of the protein are equal from one site to another. However, if the protein is natively very flexible (such as proteins that do not crystallize, like casein), denaturation using urea would not be required and the protein can then be subjected to flow through the reactor by dissolving it in a simple buffer such as an acid buffer.

In one embodiment, the present invention provides compositions and methods for characterizing the native structure of a protein such as IgG (e.g. localization of the disulfide bonds in IgG), or other highly folded proteins, by preserving the structure of the protein in its native state. As demonstrated herein, intact unalkylated IgG in 8M urea can be digested to generate ultra-large peptides that contain disulfide bond. In data not disclosed herein, the results show that using a non-denatured condition can sometimes be useful for this type of study. However, without denaturation, the digestion will occur preferably to the most flexible region of a protein and should result in a simple final digest.

The present invention further provides compositions and methods useful for preparing a reaction chamber of the invention.

The present invention further provides a kit for practicing the methods of the invention. The kit may comprise reagents as disclosed herein, compositions as disclosed herein, and an apparatus as disclosed herein. The kit may also comprise components needed to build all or part of the apparatus. The kit comprises and instructional material for practicing the methods, building and/or using the apparatus, and instructions for use of the system of the invention.

Various techniques and methods for the use of mass spectrometry, etc. are known in the art and can be found in, for example, U.S. patent application Ser. No. 13/391,331 (Syka et al.), U.S. Pat. No. 8,692,187 (Hunt et al.), U.S. Pat. No. 7,749,769 (Hunt et al.), U.S. Pat. No. 7,534,622 (Hunt et al.), and U.S. Pat. No. 8,119,984 (Shabanowitz et al.).

Other embodiments of the invention will be apparent to those skilled in the art based on the disclosure and embodiments of the invention described herein. It is intended that the specification and examples be considered as exemplary only, with a true scope and spirit of the invention being indicated by the following claims.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

Materials and Methods

Enzyme Reactor/Chamber Fabrication.

The protease aspergillopepsin I was immobilized on 20 μm aldehyde-functionalized particles by reductive amination under a "salting out" condition. See Supplemental Information (S.I.) below for details. The enzyme modified particles were suspended in water and packed into a 360 μm o.d.×150 μm i.d. fused silica capillary to form a 2-14 cm long enzyme reactor.

Aspergillopepsin I (Enzyme Commission Number 3.4.23.18; GenBank Accession Number BAA04988.1; SEQ ID NO:32) is an enzyme with broad specificity that catalyzes the hydrolysis of proteins. It generally favors hydrophobic residues in P1 and P1', but also accepts Lys in P1.

The coding region of the aspergillopepsin I gene occupies 1340 base pairs of the genomic DNA and is separated into four exons by three intros. The predicted amino-acid sequence of aspergillopepsin I consists of 325 residues and is 32% and 27% homologous with those of human pepsin and calf chymosin. The cDNA of the gene prepared from mRNA has been cloned and expressed in yeast cells. To identify the residue of the substrate-binding pocket in determining the specificity of aspergillopepsin I towards basic substrates, this residue was replaced with a serine residue by site-directed mutagenesis. The mutation is a single amino-acid change, Asp-76 converted to Ser-D76S, in the enzyme.

The striking feature of this is that only the trypsinogen activating activity was destroyed. See for example, Shintani et al., Volume 1204, Issue 2, 16 Feb. 1994, Pages 257-264.

The crystal structure of aspergillopepsin I (AP) from *Aspergillus phoenicis* has been determined at 2.18 Å resolution and refined to R and Rfree factors of 21.5 and 26.0%, respectively. AP has the typical two β-barrel domain structure of aspartic proteinases. The structures of the two independent molecules are partly different, exemplifying the flexible nature of the aspartic proteinase structure. Notably, the 'flap' in one molecule is closer, with a largest separation of 4.0 Å, to the active site than in the other molecule. AP is most structurally homologous to penicillopepsin (PP) and then to endothiapepsin (EP), which share sequence identities of 68 and 56%, respectively. However, AP is similar to EP but differs from PP in the combined S1'-S2 subsite that is delineated by a flexible ψ-loop in the C-terminal domain. The S1' and S2 subsites are well defined and small in AP, while there is no definite border between S1' and S2 and the open space for the S2 subsite is larger in PP. Comparison of the structures indicates that the two amino-acid residues equivalent to Leu295 and Leu297 of AP are the major determining factors in shaping the S1'-S2 subsite in the fungal aspartic proteinases. See Cho et al., Acta Cryst. Section D Volume 57, Part 7 (July 2001).

Sample Preparation and Protein Digestion

Apomyoglobin from equine skeletal muscle (Sigma) was dissolved in the digestion buffer (pH 3.9 containing 8M urea) at a concentration of 0.2 μg/μL and pressure-loaded through the enzyme-column at different flow rates to achieve different digestion times. The samples were collected in Eppendorf tubes separately and stored at −35° C. prior to analysis. To digest mAb (mouse IgG1, Waters) with the enzyme column, the disulfides of mAb were reduced with tris(2-carboxyethyl)phosphine (TCEP) and alkylated with NAEM in buffers containing 8M urea. The alkylated mAb was acidified and diluted to 0.2 μg/μL (final pH 3.9 with 8M urea) for on-column digestion as described above. MAb was also reduced and alkylated with iodoacetamide (IAM) in pH 8 buffer containing 8M urea and diluted fivefold (final pH 8.0 with 1.6M urea) for conventional in-tube digestion with Lys-C and Asp-N. See Supplemental Information (S.I.) below for detailed procedures.

Chromatography and Mass Spectrometry.

An Agilent Technologies (Palo Alto, Calif.) 1100 Series binary HPLC system was interfaced with LTQ-Orbitrap Velos mass spectrometer for online separation of protein digests. One pmol protein digest was pressure-loaded onto a precolumn (360 μm o.d.×150 μm i.d. fused silica capillary packed with 11 cm long POROSHELL 300SB-C18 (5 μm diameter, Agilent)). After desalting, the precolumn was connected to an analytical column (360×50 μm i.d. capillary packed with the same material) which was equipped with a laser-pulled nanoelectrospray emitter tip. Peptides were eluted at a flow rate of 60 nL/min using the following gradient: 0-25% B for 5 min, 25-60% B for 105 min, 60-100% B for 4 min (A=0.3% formic acid in water; B=0.3% formic acid, 72% acetonitrile, 18% isopropanol and 9.7% water).

Mass spectrometric analyses included a LC-MS experiment with only full MS scans in Orbitrap for sample evaluation (Experiment I), followed by multi-segment LC-ETD MS/MS scans in Orbitrap (Experiment II) targeting on major large peptides (3000-9000 Da) selected from Experiment I. Each segment in Experiment II included a group of peptides that eluted close to each other. For each selected large peptide, the ion with the highest charge state (but with sufficient intensity) was selected as the precursor for MS2. The ETD reaction time was set based on the following formula, $t=50 \text{ ms} \times (3/\text{charge state})^2$. For mAb analysis, CAD MS/MS was performed as Experiment #3 in a similar way as in Experiment II to generate complimentary peptide sequence information. See S.I. for detail MS settings.

Supplemental Information

Materials and Methods

Protease Immobilization

Near saturated $Na_2SO_4$ solution was prepared by dissolving 0.28 g $Na_2SO_4$ in 1 mL of water at 80° C., letting it cool down, and removing all the residual insoluble $Na_2SO_4$ using centrifugation. Aspergillopepsin I (protease from Aspergillussaitoi, Type XIII, Sigma) was dissolved in the saturated $Na_2SO_4$ solution at 10 mg/mL followed by centrifugation to remove the precipitations. Next, 200 μL of the clear aspergillopepsin I solution was mixed with 7 mg of aldehyde-functionalized particles (POROS® AL 20 am Self Pack® Media, Life Technologies) followed by addition of 1 μL of 80 mg/mL of $NaCNBH_3$ (prepared in saturated $Na_2SO_4$ solution). The mixture was gently shaken for 19 hours at room temperature for protease conjugation, and then transferred into a spin column filter (pore size<20 μm). The conjugation solution was filtered through the column by centrifugation (2,000 rcf for 30 s, the same for the following steps). The enzyme-modified POROS AL beads were washed by adding 0.5 mL of water into the spin column, shaking for 1 minute, and removing the water by centrifugation. This step was repeated for two more cycles. The unreacted aldehyde groups on the POROS AL particles were blocked with tris(hydroxymethyl)aminomethane(Tris) by adding 300 μL of 0.2M Tris-HCl buffer (pH 6.5) containing 0.27 mg/mL $NaCNBH_3$ to the washed particles in the spin column, followed by shaking the particle suspension for 2 hours at room temperature. Finally, the enzyme-modified particles were washed with water for three times in the spin column, dried by centrifugation, and stored at 4° C.

Sample Preparation and Size-Controlled Proteolysis

Digestion buffer was prepared by mixing 100 μL of 8M urea in 0.5M ammonium acetate, 8 μL of 25% formic acid, and 892 μL of 8M urea in 0.5% acetic acid (final pH 3.9). Prior to protein digestion, the enzyme-column was washed with the digestion buffer. In the meantime, the flow rate was measured and adjusted to a desired value with the digestion buffer by tuning the pressure applied to the enzyme-column. To digest apomyoglobin (apomyoglobin from equine skeletal muscle, Sigma), the protein was dissolved in the digestion buffer at a concentration of 0.2 μg/μL and pressure-loaded through the enzyme-column at different flow rates to achieve different digestion times. The protein digest was collected in an Eppendorf tube and stored at −35° C. prior to analysis.

For mAb sequence verification and PTM characterization, monoclonal mouse IgG1 (Waters) was reduced and alkylated prior to on-column size-controlled digestion. Specifically, 20 μg of mAb was dissolved in 10 μL of 10 mM tris(2-carboxyethyl)phosphine hydrochloride (TCEP.HCl) prepared in 8M urea containing 0.1% acetic acid. After incubation at 50° C. for 10 minutes, the sample was neutralized to pH 6.8 by adding 2.0 μL of 0.2M ammonia. Cys was alkylated by adding 10 μL of 20 mM NAEM freshly prepared in 0.5M ammonium acetate buffer containing 8M urea (pH 6.8) followed by 10 minutes incubation. The sample was immediately acidified to pH 3.9 by adding 1 μL of 25% formic acid. The alkylated mAb was finally diluted to 0.2 μg/μL with the digestion buffer, and on-column digested as described above.

To digest mAb with Lys-C and Asp-N, 20 µg of mouse IgG1 was dissolved in 7 µL of 2 mM TCEP.HCl prepared in 0.1% acetic acid containing 8M urea, and incubated at 50° C. for 10 minutes. The sample was then added with 7 µL of 20 mM iodoacetamide (IAM) prepared in 2M ammonium bicarbonate containing 8M urea, followed by incubation in the dark at room temperature for 30 minutes. Unreacted IAM was quenched by adding 6 µL of 30 mM dithiothreitol (DTT) prepared in 100 mM ammonium bicarbonate containing 8M urea, followed by incubation in the dark at room temperature for 20 minutes. To prevent protease from being deactivated by 8M urea, the sample was diluted by fivefold with 100 mM ammonium bicarbonate, followed by adding 2 µL of 0.5 µg/µL LysC or AspN (enzyme to substrate ratio 1:20, final pH 8.0 with 1.6M urea). The digestion was carried out at 37° C. for 10 hours and quenched to pH 3 with glacial acetic acid.

For mAb disulfide localization, 0.2 µg/µL mouse IgG$_1$ was directly dissolved in the pH 3.9 digestion buffer containing 8M urea, followed by on-column digestion. Four different digestion times, 12 s, 93 s, 260 s, and 740 s, were adopted to produce disulfide-containing large peptides (mostly 5-12 kDa) hydrolyzed gradually from different portions of the mAb. An aliquot of each digest sample was also reduced with TCEP at pH 3.9. All the samples were stored at −35° C. prior to analysis.

Mass Spectrometry

In this work, to characterize protein sequence and PTMs, typical mass spectrometric analyses included a LC-MS experiment with only full MS scans for sample evaluation (Experiment #1), and one or two LC-MS experiments with targeted MS/MS scans for peptide sequencing and PTM characterization (Experiment #2 for ETD and #3 for CAD). Specifically, Experiment #1 included high-resolution MS1 scans (m/z 300-2000) in the Orbitrap (resolving power of 60,000 at m/z 400), which gives the m/z information of each peptide. The following MS/MS experiments were designed according to the size of the target protein.

(1) For small or medium size proteins (apomyoglobin in this work), to achieve optimal ETD MS/MS, the MS/MS settings in Experiment #2 were divided into multiple 5-10 min period segments such that each segment was targeted only on the base peak peptide with 3000-9000 Da molecular weight (MW) found in Experiment #1. The ETD MS/MS settings in each time segment of Experiment #2 included repeated alternate MS1/MS2 scans in Orbitrap (60,000 resolving power at m/z 400 and 500 ms maximum ion injection time for both MS1 and MS2; 1 micro scan for MS1 and 3 micro scans for MS2). Precursor isolation window for MS2 was typically set as 5 m/z. To achieve optimized ETD of the targeted peptide in each time segment, the ion with the highest charge state was chosen as the precursor for ETD, instead of using the most abundant ion as in most data dependent mode bottom-up analyses. However, the optimized ETD also considered the abundance level of the chosen precursor ion (should be at least 5E6) and whether the 5 m/z isolation window included other ions with comparable abundance as the target ion (these information was obtained from Experiment #1). If so, the ion with the second highest charge state was chosen as the precursor for ETD. For peptides with the selected m/z too close to other nearby ions, 3 m/z or 4 m/z isolation window was chosen. For optimal ETD kinetics, the ETD reaction time was set based on the following formula, t=50 ms×(3/charge state)$^2$. Automated gain control (AGC) was set as 1E6 for both FTMS and FTMSn, and 3E5 for ETD reagent.

(2) For large size proteins (mAb in this work), a higher number of large peptides need to be targeted in MS/MS experiment. The MS1 total ion count (TIC) chromatogram from Experiment #1 was divided into multiple 5-15 min period segments where the division points were selected at the lowest valleys of the TIC signals. To pick the major large peptides from Experiment #1 without being complicated by the multiple charge states of each large peptide, the MS1 data in each time segment of Experiment #1 was simplified by converting the m/z to peptide monoisotopic MW using Xcalibur Xtract.

The rules for selecting major large peptides from each time segment are as follows. First, only peptides with MW between 3000-9000 Da and the intensity above 2E6 (after conversion to MW) were selected. However, peptides in 1000-3000 Da range were also included if they appeared as the base peak with exceptional high abundance (above 1E7 in MS1 after conversion to MW) compared to other major large peptides. The selected peptides in each time segment were then ranked according to their intensity and some weaker ones were discarded from the selection list such that the number of peptides per time segment is no more than averagely 1 peptide/minute. The original m/z and the elution time information of the finally selected major peptides (39 in total, including 38 in 3000-9000 Da size range and 1 in 1000-3000 Da size range) were used in Experiment #2 and #3 where targeted MS/MS were performed for each peptide. To perform efficient MS2 in Experiment #2, these selected peptides were grouped into 11 new time segments (3-10 min each) according to their elution time in Experiment #1, such that the peptides in each new segment have close elution time (averagely no more than 1 peptide/minute in each time segment). MS/MS settings in each time segment followed the same principle as for apomyoglobin as describe above (except for that each MS2 scan included 2 micro scans). To obtain complementary sequence information, Experiment #3 which consists of multiple CAD MS/MS scans was utilized following the same setting as in Experiment #2, except that ETD settings were replaced by CAD with default activation time (10 ms).

Principle of Size-Controlled Proteolysis

Determination of the Porosity (p) of the Protease Particles in an Enzyme Reactor.

Figure 6:
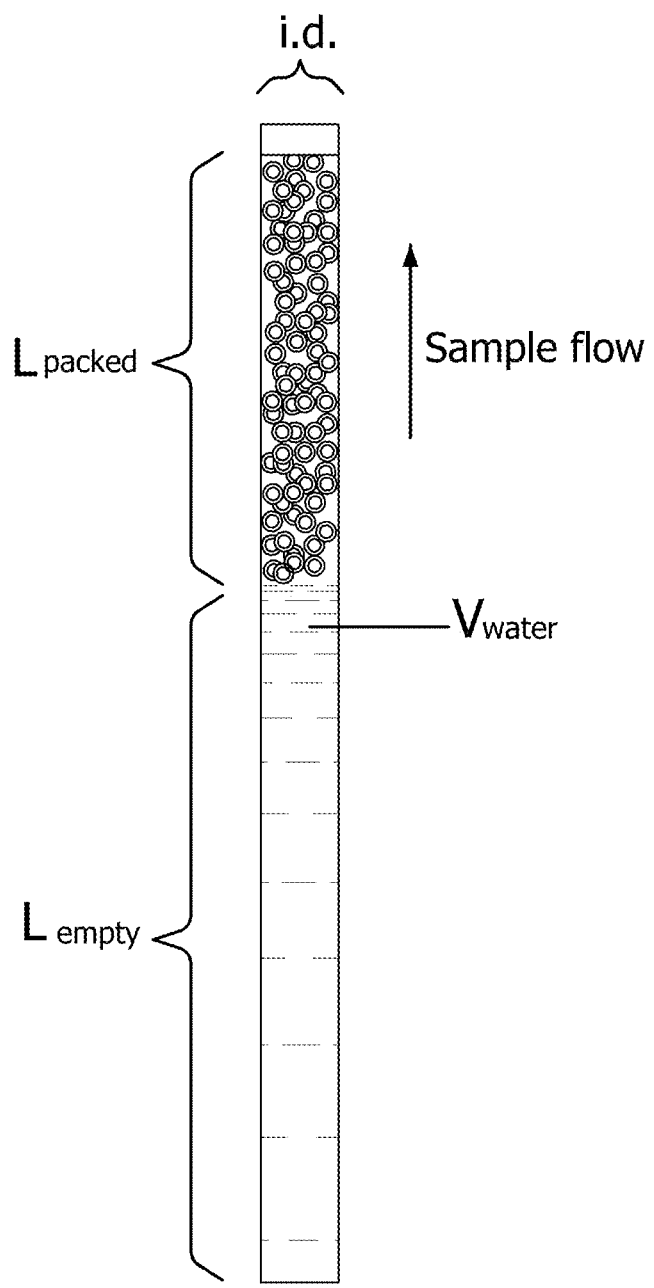
FIG. 6. Diagram of enzyme reactor. The fused silica capillary (i.d. 150 µm) was packed with POROS AL particles covalently linked with the protease, aspergillopepsin I. Three measureable values are labeled as $L_{packed}$, representing the length of the portion packed with protease particles; $L_{empty}$, representing the length of the empty portion of the column; and $V_{water}$, representing the total volume of water trapped in the whole column including the portion packed with protease particles. An entry point is provided for the sample which passes through the column at an adjustable flow rate and digestion occurs in the chamber, and an exit point allows for retrieval of digested protein to be used for characterization of protein fragments using techniques such as LS MS/MS.

The porosity, p, of the 20 µm protease particles packed in the capillary column was determined to be 30% in this work. This value was determined by first loading the enzyme-column with water, then measuring the volume of the water trapped in the whole enzyme-column (including both the packed portion and the empty portion) using a 5-µL calibrated pipet as the water was pressure-pushed off the column. The porosity p was calculated according to Equation 2 (also referred to as Equation S2), where $V_{water}$ is the volume of the water trapped in the whole column (shown in grey in FIG. 6), $V_{empty}$ is the volume of the portion with no protease particles packed, and $V_{packed}$ is the volume of the portion of the column packed with protease particles (see Equations 1, 2, and 3 below).

$$t = \frac{\pi (i.d./2)^2 L_{packed} p}{F} \quad (1)$$

$$p = \frac{V_{water} - V_{empty}}{V_{packed}} \times 100\% \quad (2)$$

$$V_{empty} = \pi \left(\frac{i.d.}{2}\right)^2 L_{empty}$$

$$V_{packed} = \pi \left(\frac{i.d.}{2}\right)^2 L_{packed}$$

-continued $$t(s) = \frac{L_{packed}(cm)}{F(\mu L/min)} \times 3.19 \quad (3)$$

Results

Principle of Time-Controlled Protein Digestion.

Figure 5:
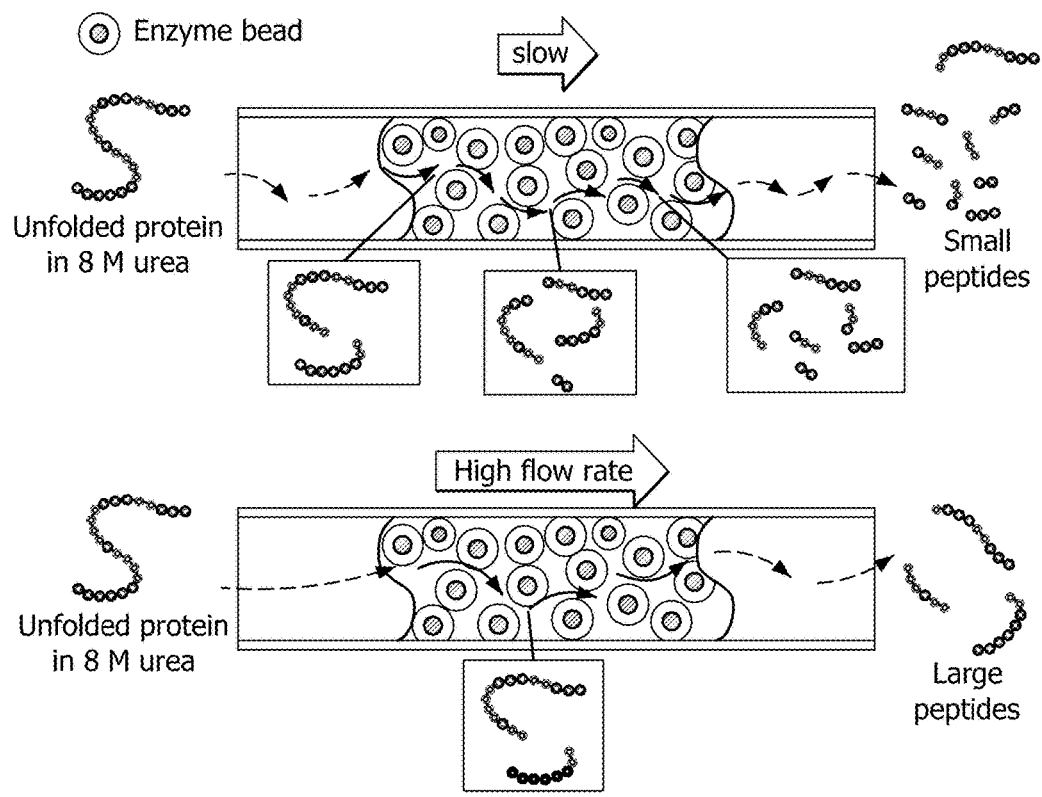
FIG. 5. Principle of size-controlled proteolysis using an enzyme reactor. See also FIG. 6.

In this work, we applied pressure to drive the protein sample through the enzyme reactor packed with a certain length of protease particles ($L_{packed}$, which can be easily measured, see FIG. 5). Maintaining a stable pressure leads to constant flow rate (F) of the sample stream in the column, and consequently constant residence time for any moving cross-section of the flowing stream as it passes through the protease particles. Assuming there is no retention of proteins or peptides on the hydrophilic protease particles, the residence time (t) of any single protein "molecule" (here defined as a given protein molecule in either the starting intact form or its following hydrolyzed forms) should be the same as that of the stream cross section where the protein "molecule" exists. Based on this assumption, the residence time t, also defined as the on-column digestion time, for each single protein "molecule" can be calculated using Equation S1, where i.d. is the inner diameter of the capillary column, $L_{packed}$ is the length of packed protease particles, F is the sample flow rate, and p is the porosity of the packed protease particles in the column (see Equation S2 for the determination of p). As p in the 150 µm i.d. column is a constant value (30% in this work) independent of other parameters, Equation S1 can be simplified to Equation S3. Thus, the digestion time t can be precisely controlled by maintaining a proper flow rate F that is proportional to $L_{packed}$. This is beneficial to repeating a time-controlled digestion using a new enzyme reactor with a different $L_{packed}$ from before. Equations S1, S2, and S3 are also referred to as Equations 1, 2, and 3 herein.

Sequencing Medium Size Protein Using Base Peak Large Peptides.

Figure 8C:
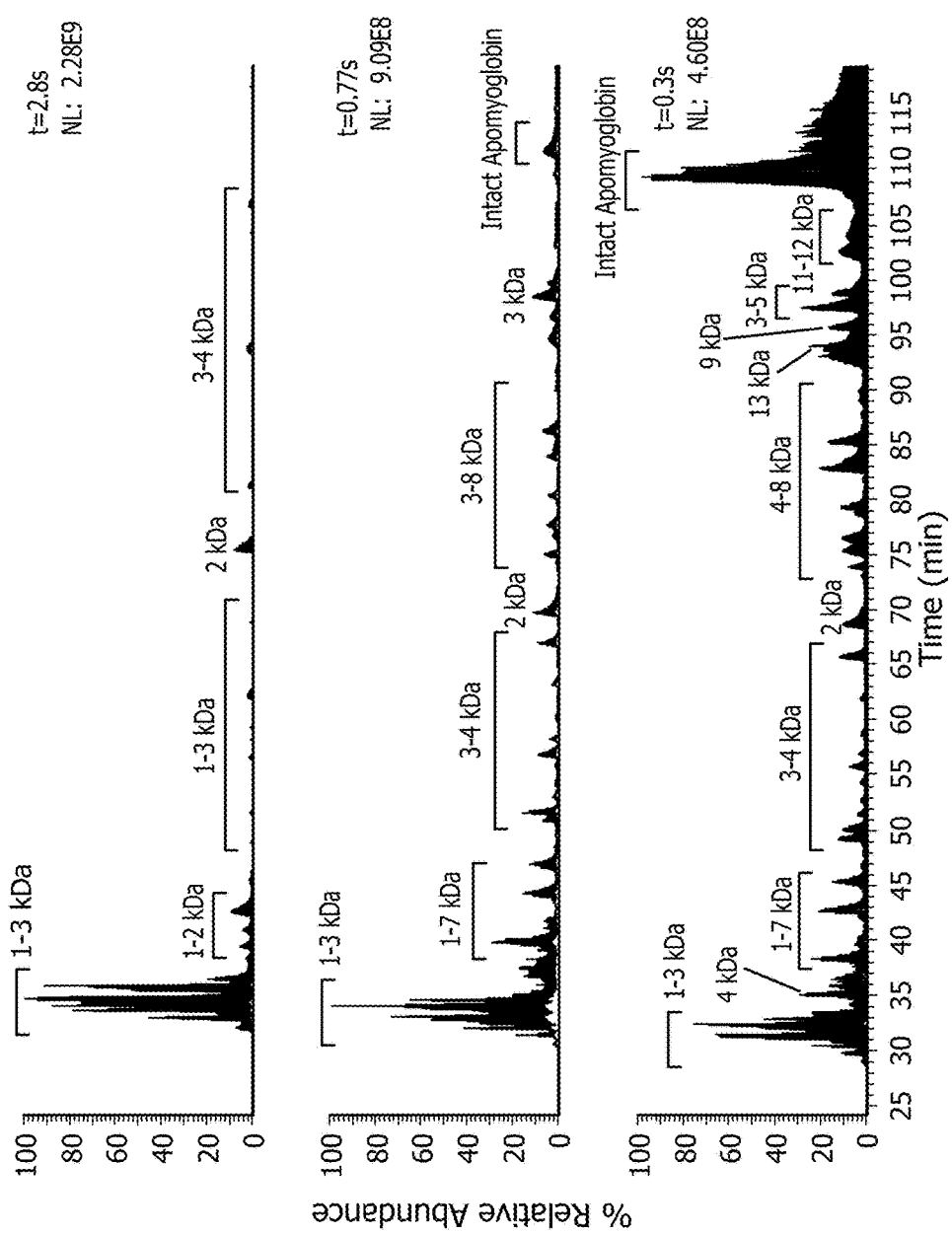
FIG. 8, comprising FIGS. 8A to 8C. Sample preparation and protein digestion. Sequences of mouse (A) Lc (SEQ ID NO:6) and IgG1 He (SEQ ID NO:7) (B) mapped by ETD (labeled as c and z ions) and CAD (labeled as b and y ions) using XXX major large peptides generated by 5.7 s size-controlled digestion. The major proteolysis sites are labeled by dashed lines between two adjacent amino acids. (C) Total ion current (TIC) of LC-Orbitrap MS for apomyoglobin digests produced from size-controlled digestion with three different digestion times. The digestion time (t) and normalized ion count (NL) are notified in each TIC chromatogram. Peptides sizes and undigested apomyoglobin are labeled within each chromatogram.

On-column digestion of apomyoglobin (17 kDa) with different residence times results in peptides of different size ranges, as displayed in FIG. 8. Small peptides with the molecular weight (MW) below 3 kDa dominate the total ion current (TIC) chromatogram when the digestion time was controlled as 2.8 s. The total amount of small peptides drops to ~40% after shorting the digestion time to 0.77 s. In the meantime, 3-9 kDa large peptides appear in the majority of the chromatography with base peak separation. Further decreasing the digestion time to 0.30 s creates even larger peptides (9-13 kDa). However, these ultra-large peptides are accompanied with high abundant undigested apomyoglobin appearing in the end of the gradient, suggesting an inefficient digestion. To confirm that the varied peptide size is not due to the decrease of enzyme activity in 8M urea, we continuously passed the pH 3.9 loading buffer containing 8M urea through the enzyme reactor for 60 min, but on-column digested apomyoglobin (6.2 s residence time) at the 20 min and 60 min time points. The similar TIC chromatograms of the two digests (FIG. 14) suggest consistent activity of immobilized Aspergillopepsin in this extreme chaotropic condition. Considering both the benefit brought by large peptides and the digestion efficiency, we chose the 0.77-s digestion sample for apomyoglobin sequencing in the following ETD MS/MS experiment (Experiment II).

Experiments also show that other proteases are useful. For example, Lys-N digests proteins under harsh conditions that improved protein solubility or denaturation, including 8M urea, 70° C., and buffer containing 50% acetonitrile (data not shown).

Large peptides typically appear as a series of highly charged ions with a Gaussian-like distribution of different charge states. To simplify analysis and achieve efficient MS/MS, we divided the MS/MS method of Experiment II into multiple time segments according the elution time of each base peak large peptide (information obtained from Experiment I). Each segment includes repeated ETD MS/MS scans on a 3-9 kDa base peak peptide, with the precursor selected on the ion with the highest charge state, and the ETD reaction time set inversely proportional to the square of the charge state of the precursor ion (16, 17). In the example shown in FIG. 1A, MS1 spectrum presents three major ions with +5-+7 charge states from the base peak eluting near 80 min. Selecting the +7 ion, instead of the most abundant ion (+6), for ETD (9.2 ms ion-ion reaction time) in Experiment II resulted in a high quality MS2 spectrum. This spectrum yields complete sequence coverage (except for P due to the connected H-P residues by the Proline ring after ETD) of this 4332 Da peptide, which is identified to be Myo 114-153.

Figure 9A:
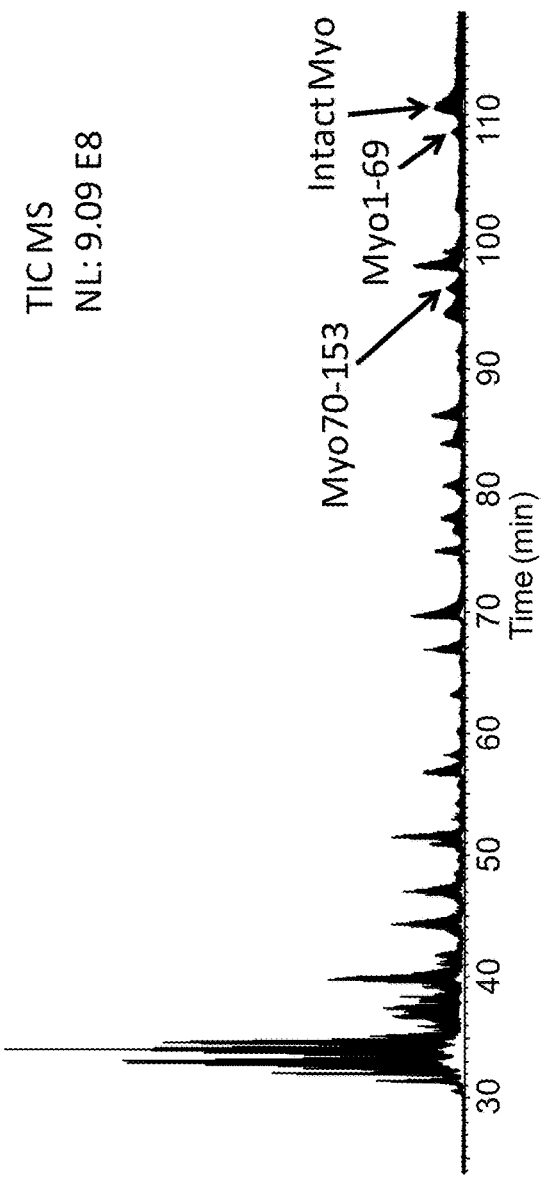
FIG. 9, comprising FIGS. 9A to 9B. (A) Total ion current (TIC) of LC-Orbitrap MS for apomyoglobin digest produced from 0.77 s on-column digestion. Two large peptides, Myo1-69 and 70-153, and the leftover undigested apomyoglobin are labeled. (B) Schematic drawing of mouse IgG1, with Fab representing the antigen-binding fragment, and Fc representing the crystallizable fragment.

Among all the base peak peptides targeted for MS/MS in Experiment II, four of them, corresponding to Myo 1-31, 32-69, 70-113, and 114-153, compose the whole sequence of apomyoglobin (FIG. 7). Peptide 70-113 has two missing ETD cleavage sites; however, ETD of another base peak peptide 105-153 covers the two sites. With the five large peptides, targeted ETD MS/MS mapped 142 amino acids of apomyoglobin. Adding two additional sites contributed from the time-controlled digestion, this strategy identified 97% of apomyoglobin sequence (not considering Pro) as shown in FIG. 7. We also found two base-peak peptides, Myo 1-69 and 70-153, which make up the whole apomyoglobin (FIG. 9A). Performing ETD/IIPT on the two peptides resulted in 86% sequence coverage of apomyoglobin.

Application of Time-Controlled Digestion and Multi-Segment LC MS/MS to MAb Sequencing.

Figure 12A:
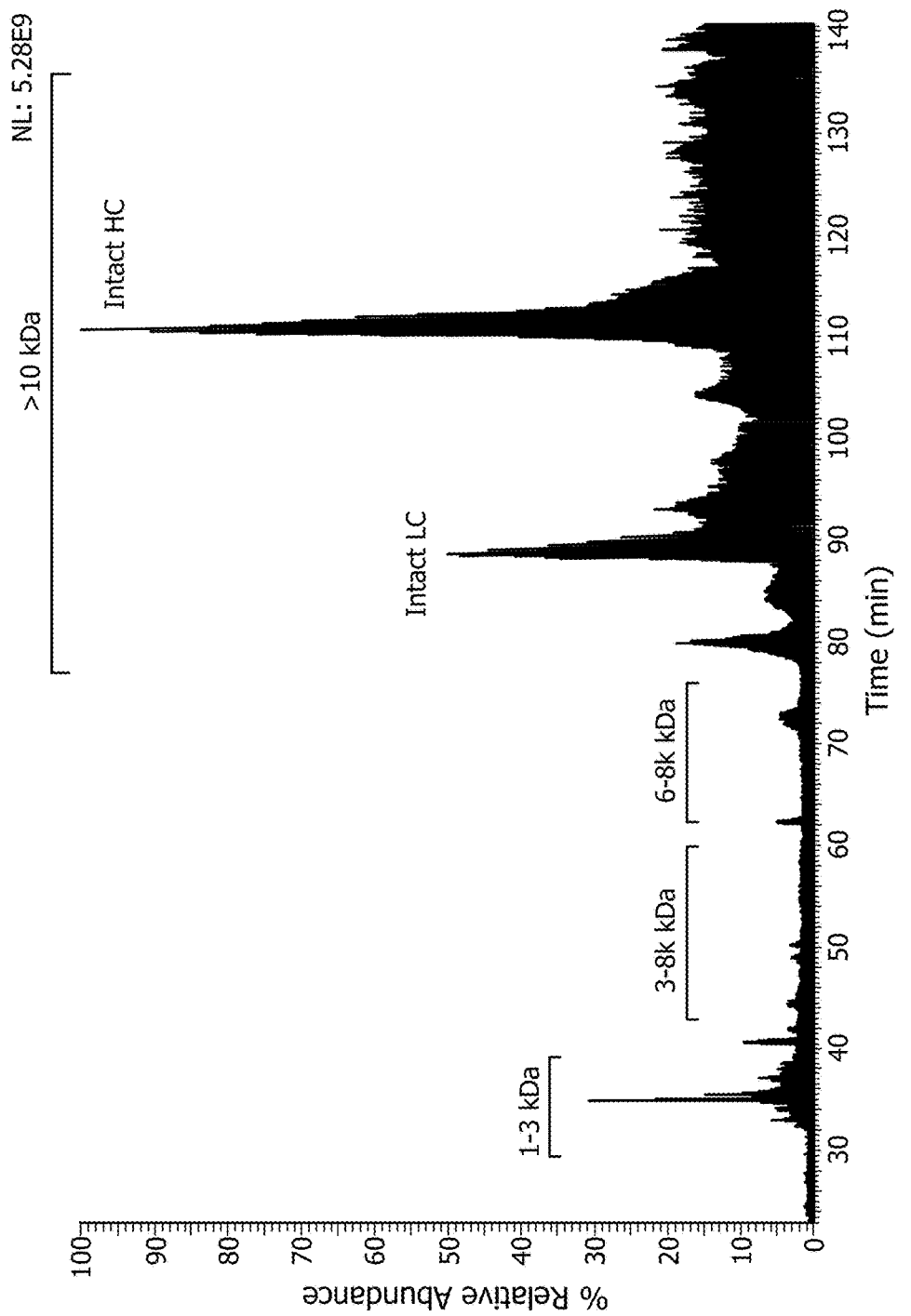
FIG. 12, comprising FIGS. 12A to 12B. TIC chromatogram of fully alkylated IgG after 10-hour in-tube digestion by Asp-N (A) and Lys-C (B) performed in pH 8 buffers containing 100 mM $NH_4HCO_3$ and 1.6M urea at 37° C., with 1:20 protease/IgG mass ratio. Peptides of different size ranges are labeled in each chromatogram.
Figure 12B:
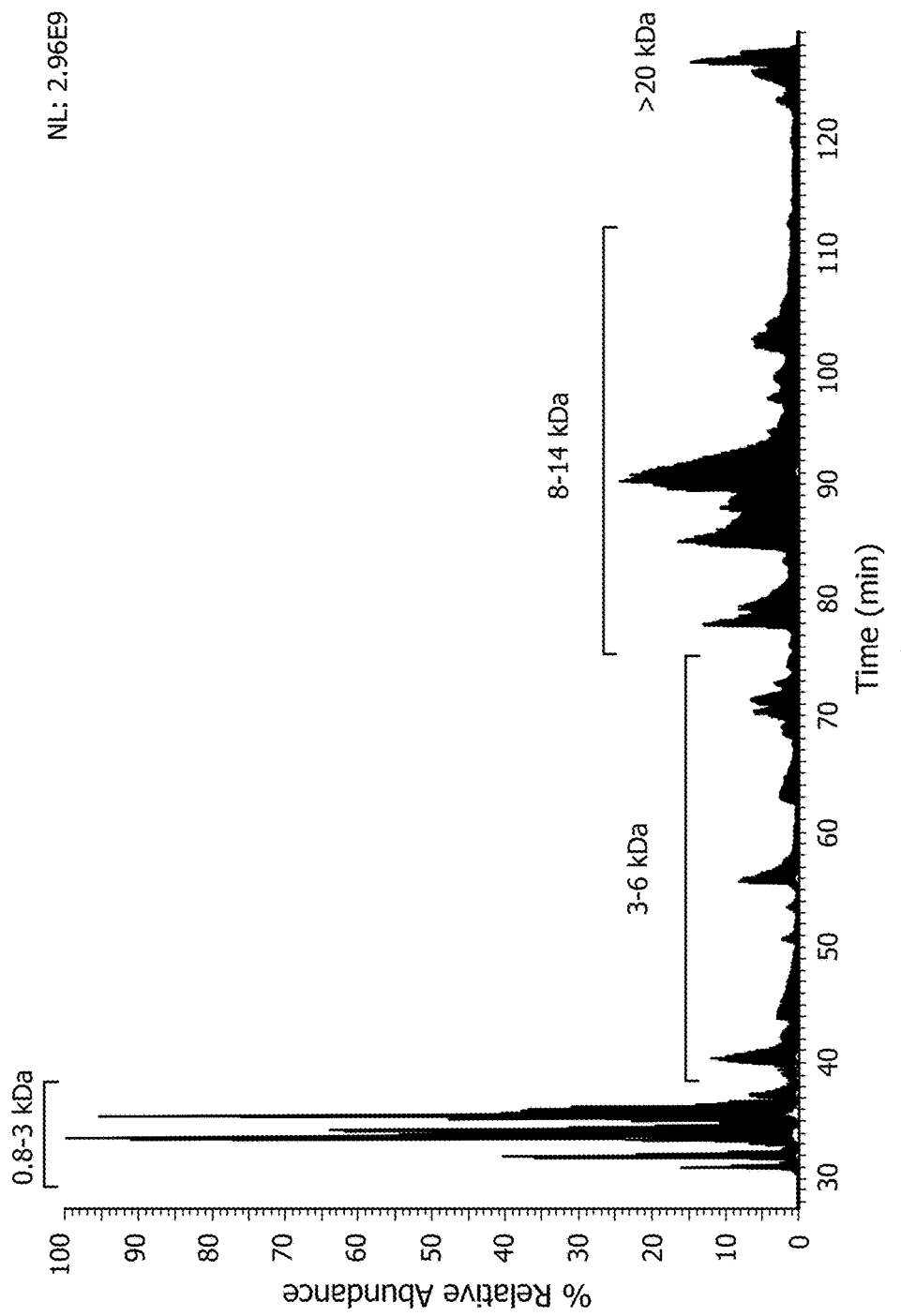

We applied the time-controlled digestion and multi-segment targeted LC MS/MS to mAb sequencing and identification of mAb PTMs. A typical mAb is a 150 kDa IgG composed of two identical heavy chain polypeptides (Hc, ~50 kDa) and two identical light chain polypeptides (Lc, ~25 kDa). They are highly folded and held together by multiple intra- and inter-molecular disulfide bonds to form a Y-shaped structure (18). In this work, we found that 8M urea is more favorable for complete reduction and alkylation of IgG disulfides compared to other less chaotropic conditions (FIG. 10). Furthermore, opening additional intra-chain disulfides of Lc and Hc greatly increases the gas-phase charge state of Lc and Hc (FIG. 11). These results suggest that unfolding IgG secondary structure facilitates the exposure of protein backbone to the solvent, which may enhance the access of protease to some originally folded structure of IgG. Unfortunately, 8M urea deactivates most commonly used proteases. We found that adding Lys-C or Asp-N to the fully alkylated mAb sample containing only 1.6M urea still results in either protease deactivation (FIG. 12A) or the generation of many peptides with their sizes either too small (<3 kDa) or too large (8 to over 20 kDa) (FIG. 12B). The size of some peptides generated by Lys-C even far exceeds that of the expected largest peptides upon in silico digestion (FIG. 12B vs. FIG. 13A).

Figure 3A:
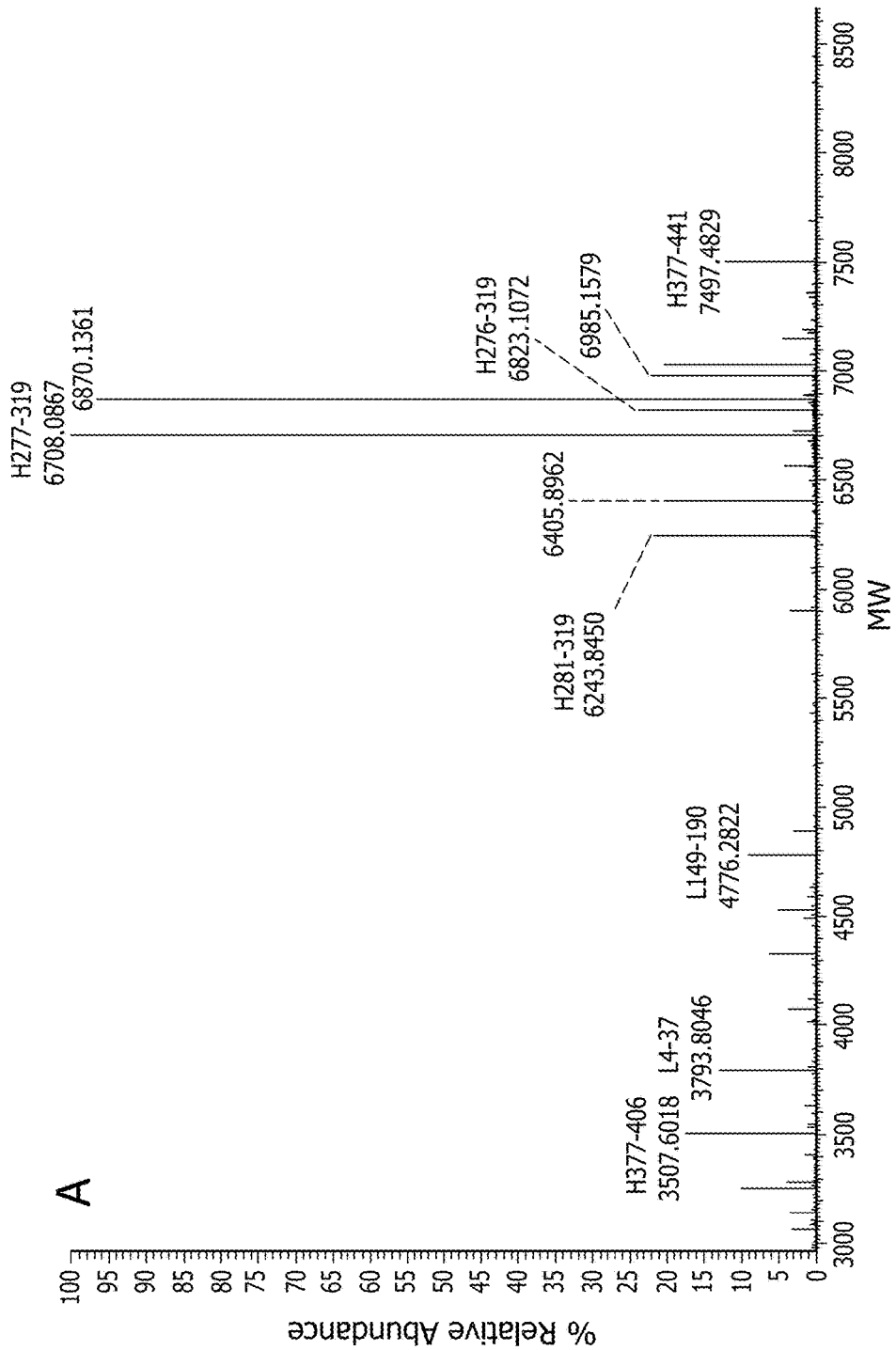
FIG. 3, comprising FIGS. 3A to 3D. (A) Merged full MS (ions converted to monoisotopic MW) of Segment I-3 of mAb digest. The labeled peptides are those picked for targeted MS/MS. The three groups of peptides correspond to three large peptides with potential N-glycans. (B, C, D) ETD MS2 of the peptide (SEQ ID NO:3) of 6780 Da MW in (A). All the ions in the original MS2 spectrum were converted to +1 charge state by Xcalibur Xtract with c and z. fragments labeled. Under the spectrum shows the sequence coverage and N-glycosylation assigned by ProSite PC (with manual verification) based on the original MS2 spectrum. More ions were labeled in the peptide sequence than in the spectrum because some fragment ions were lost in Xcalibur Xtract deconvolution.
Figure 3B:
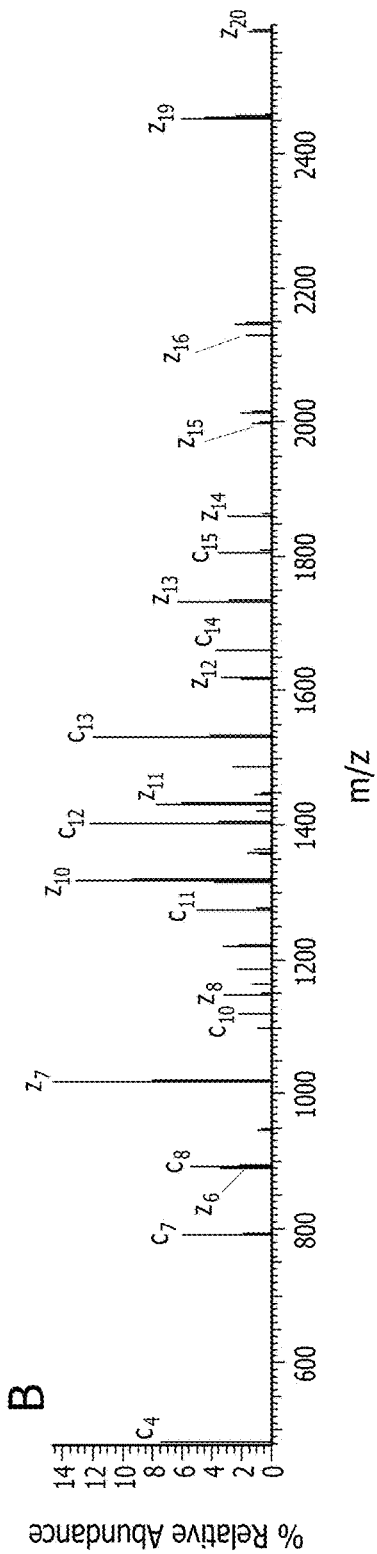
Figure 3C:
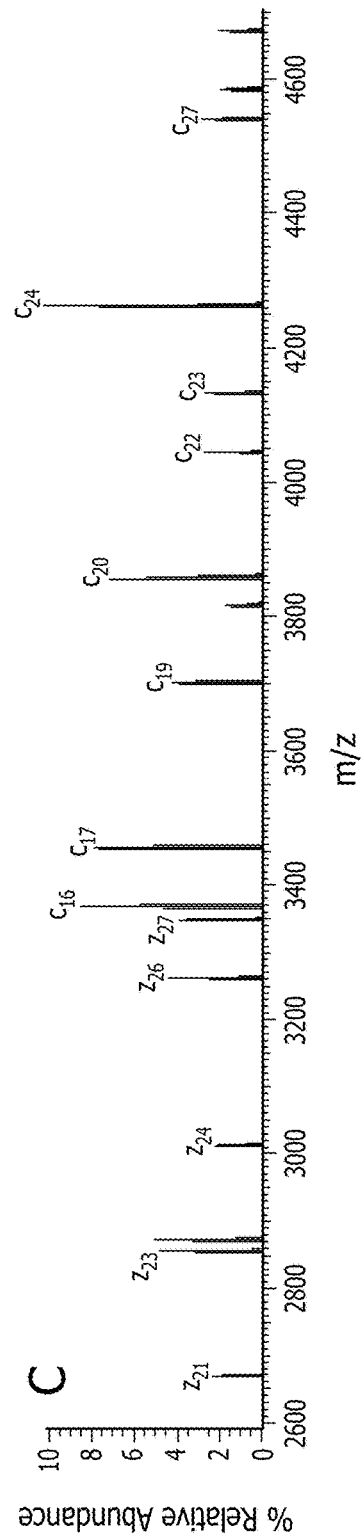
Figure 3D:
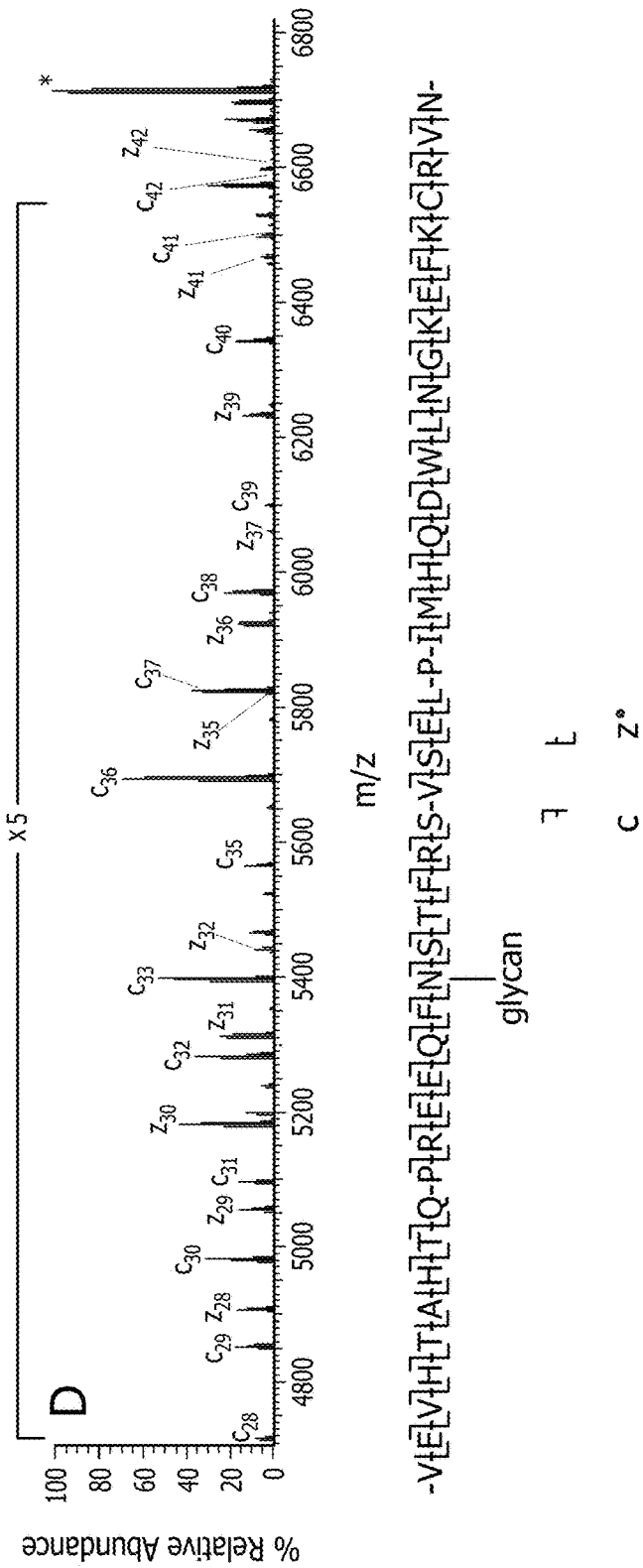
Figure 14:
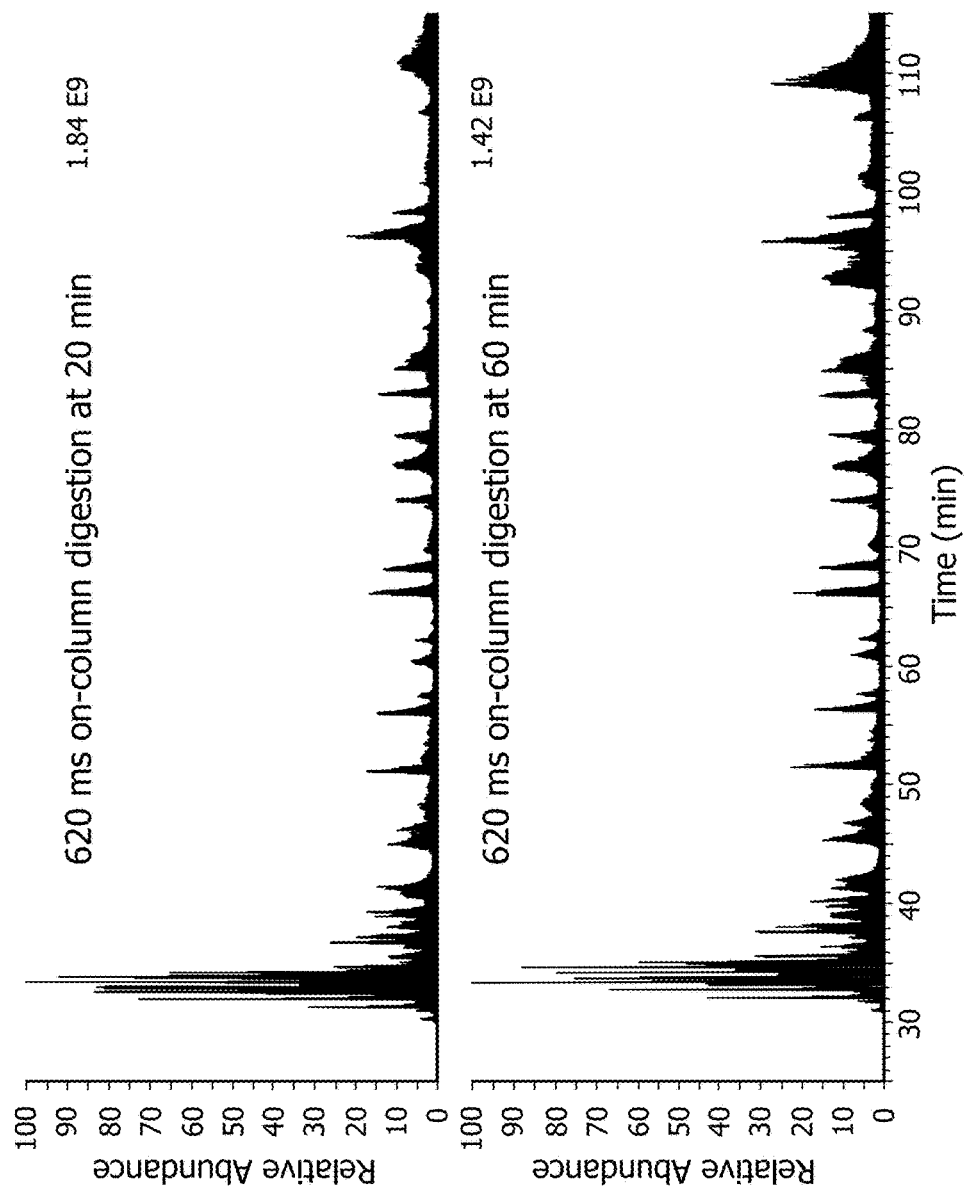
FIG. 14. Total ion current chromatograms of LC-Orbitrap MS for apomyoglobin digests produced by enzyme reactor in the 8M urea (pH 3.9) condition at 20 min (top) and 60 min (bottom) time points as the loading buffer (pH 3.9 containing 8M urea) was continuously passed though the enzyme reactor.
Figure 15A:
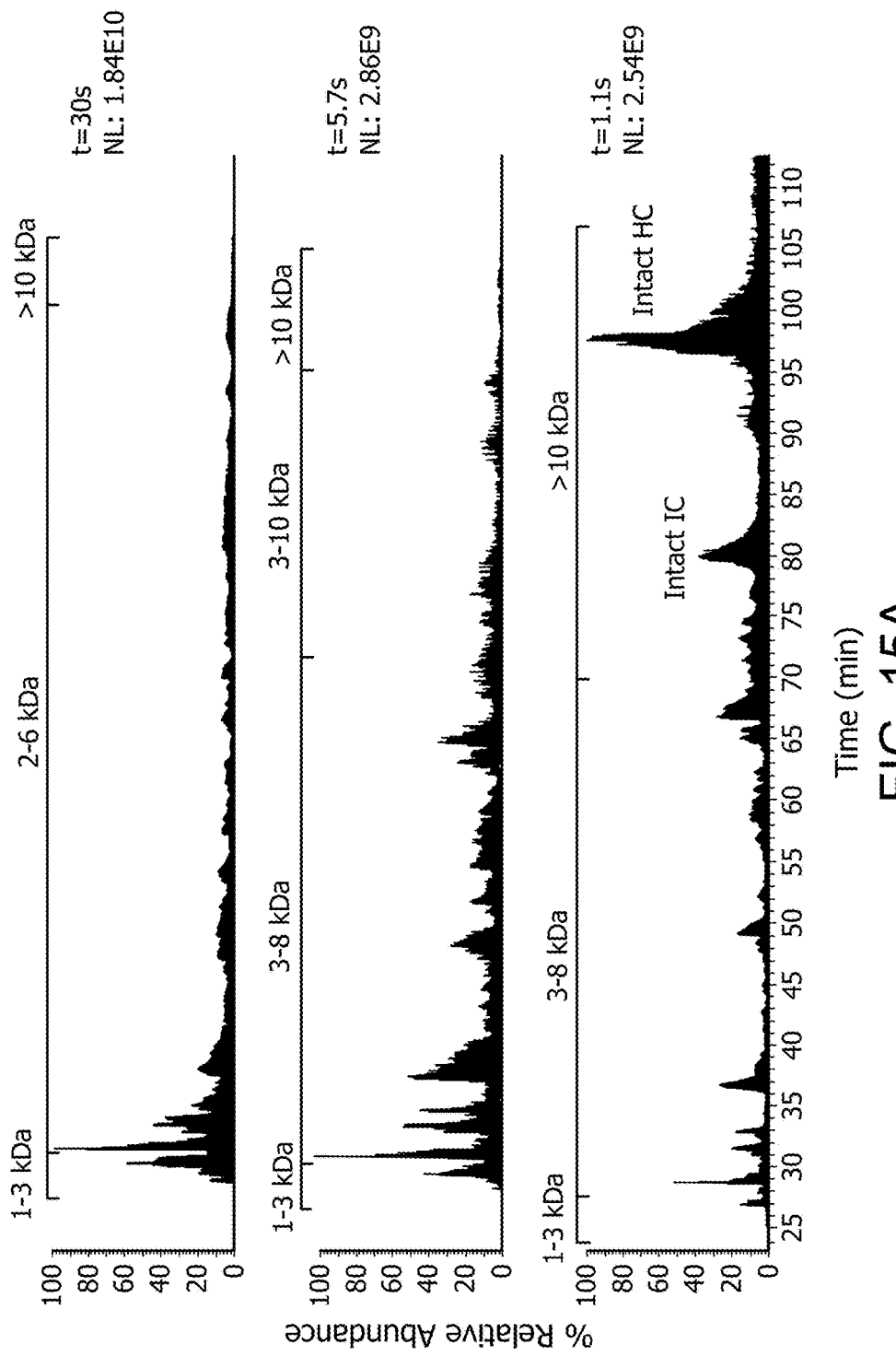
FIG. 15, comprising FIGS. 15A to 15B. (A) Total ion current chromatograms of LC-Orbitrap MS for mAb digests produced from size-controlled digestion with three different digestion times. The digestion time (t) and normalized ion count (NL) are notified in each TIC chromatogram. Peptides sizes and undigested mAb Lc and He are labeled within each chromatogram. The LC gradient is shorter than described in the experimental part. (B) TIC chromatogram of LC-Orbitrap full MS scan of mAb digest generated by 5.7 s size-controlled digestion. The whole chromatogram (gradient described in the experimental part) was divided into 8 segments for selecting major large peptides from each segment for the following targeted MS/MS analysis.
Figure 15B:
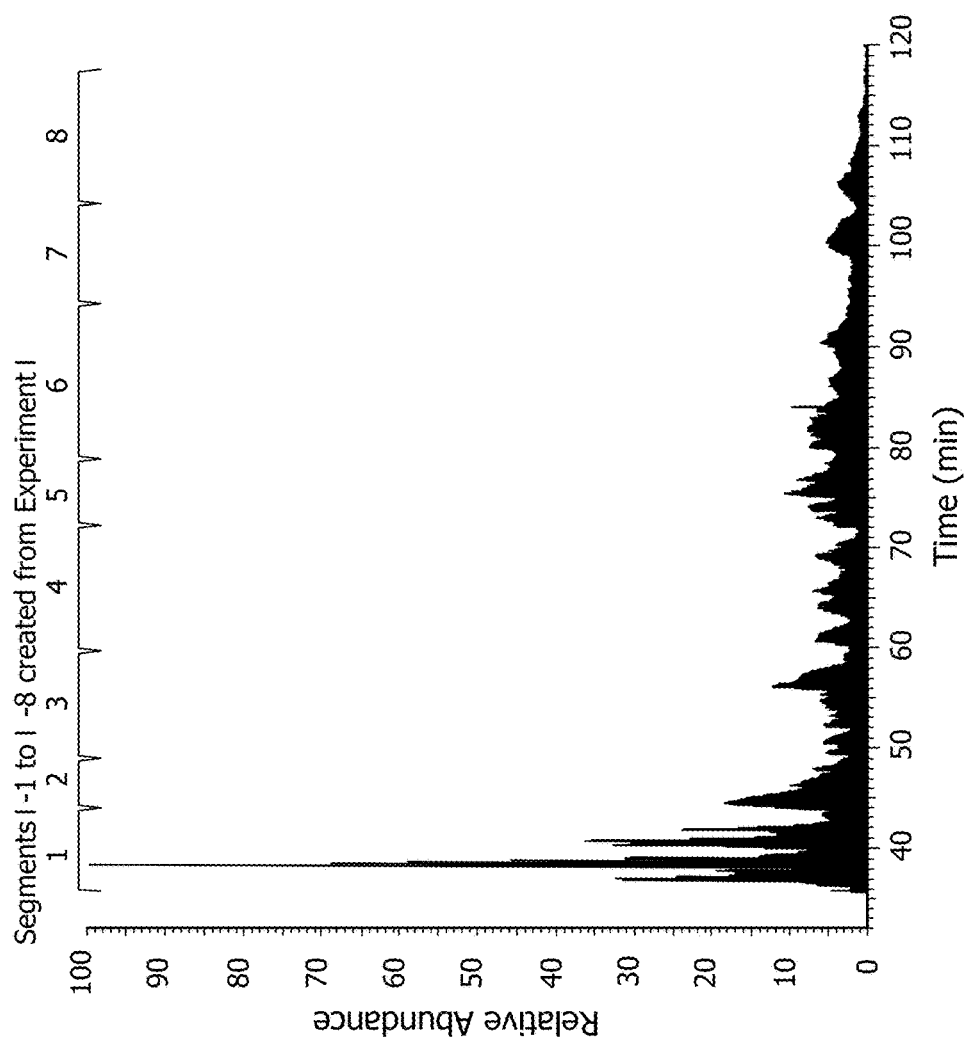
Figure 16A:
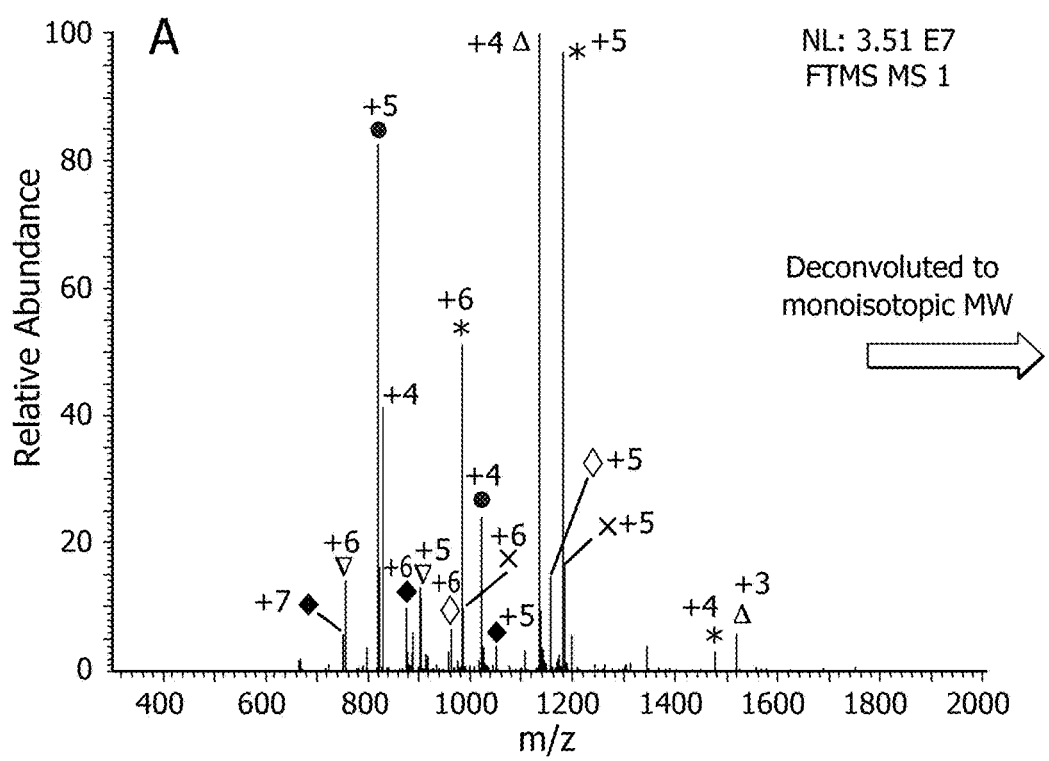
FIG. 16, comprising FIGS. 16A to 16D. (A) Merged full MS in Segment I-5 from Experiment I. Most strong ions are labeled with their charge states and symbols representing their corresponding peptides found in B. Red symbols represent the peptides that will be targeted for ETD MS/MS in Experiment II. (B) Full MS data after converting the original full MS (in A) to neutral form (molecular weight). The 7 most abundant peptides are labeled with 7 different symbols, respectively. (C) Portions of LC-MS gradient (68-80 min) in Experiments I and II. Below the gradient portion of Experiment II are 9 peptide peaks found from Segments I-4 and I-5 (Experiment I). These peptides are re-grouped in Segments II-6 and II-7 in Experiment II for targeted ETD MS/MS. (D) The ETD MS2 spectrum corresponds to the merged two scans from a peptide labeled as red V in A and C. The peptide sequence and its sequence coverage by this ETD MS2 is presented below the MS2 spectrum (SEQ ID NO:8).
Figure 16B:
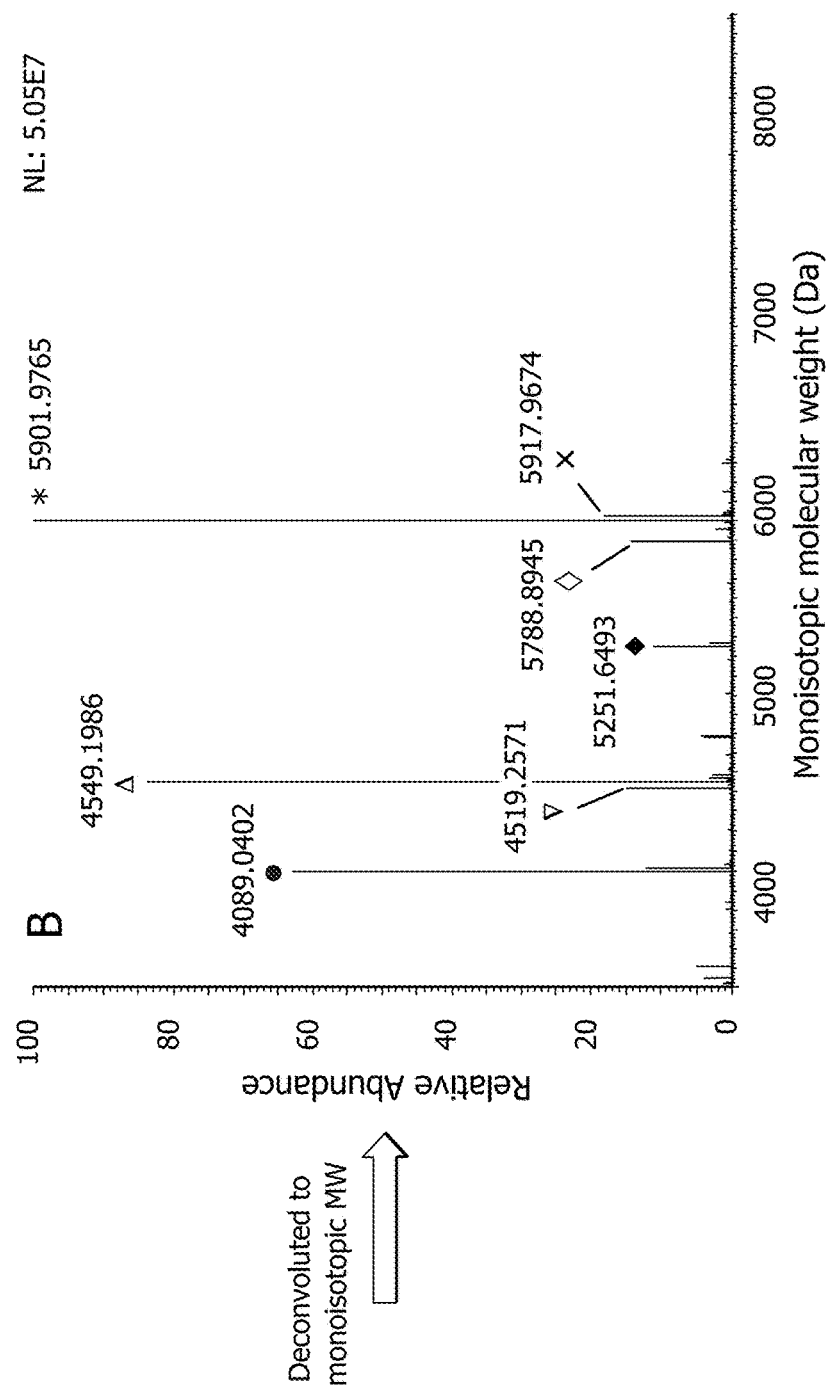
Figure 16C:
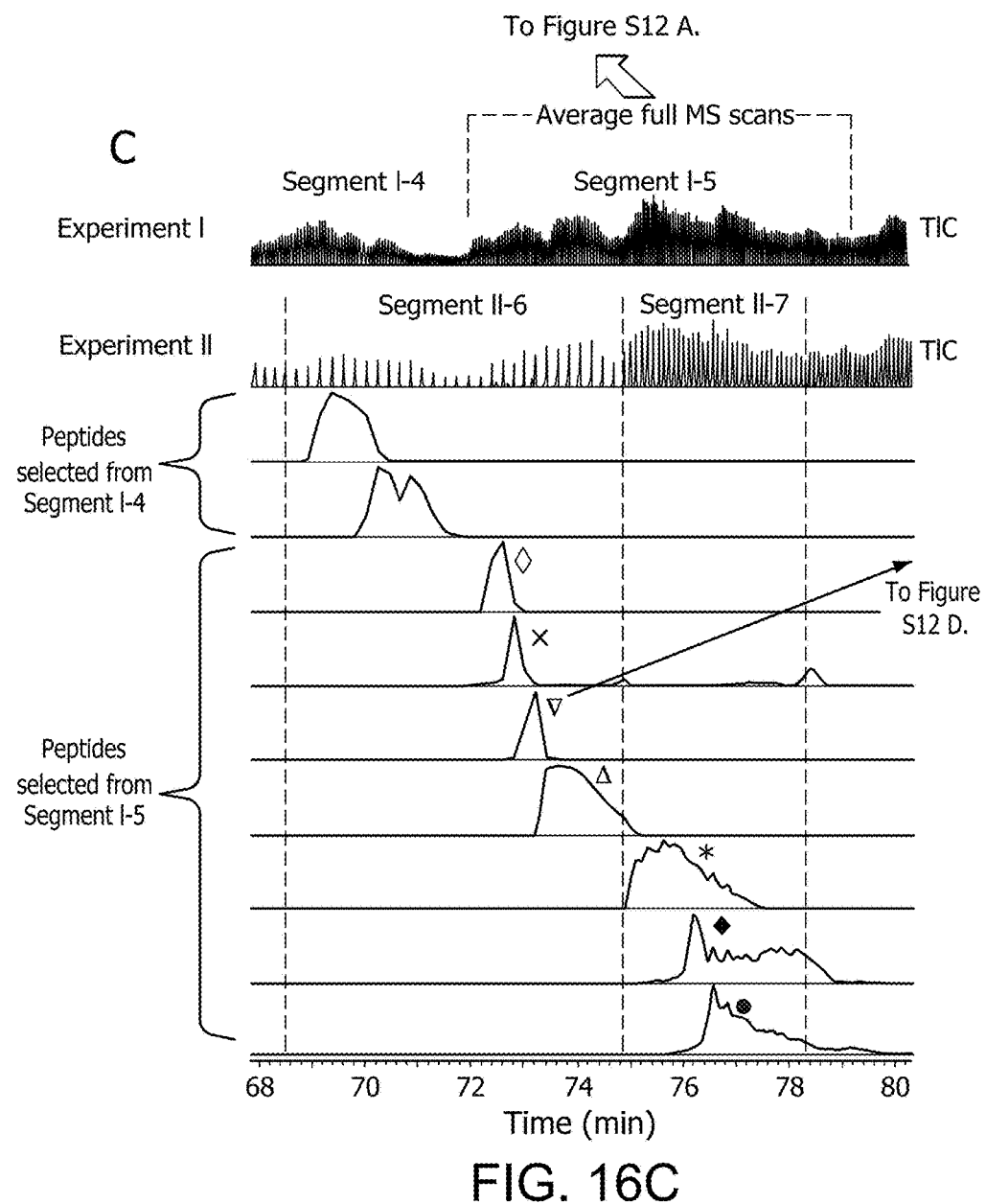
Figure 16D:
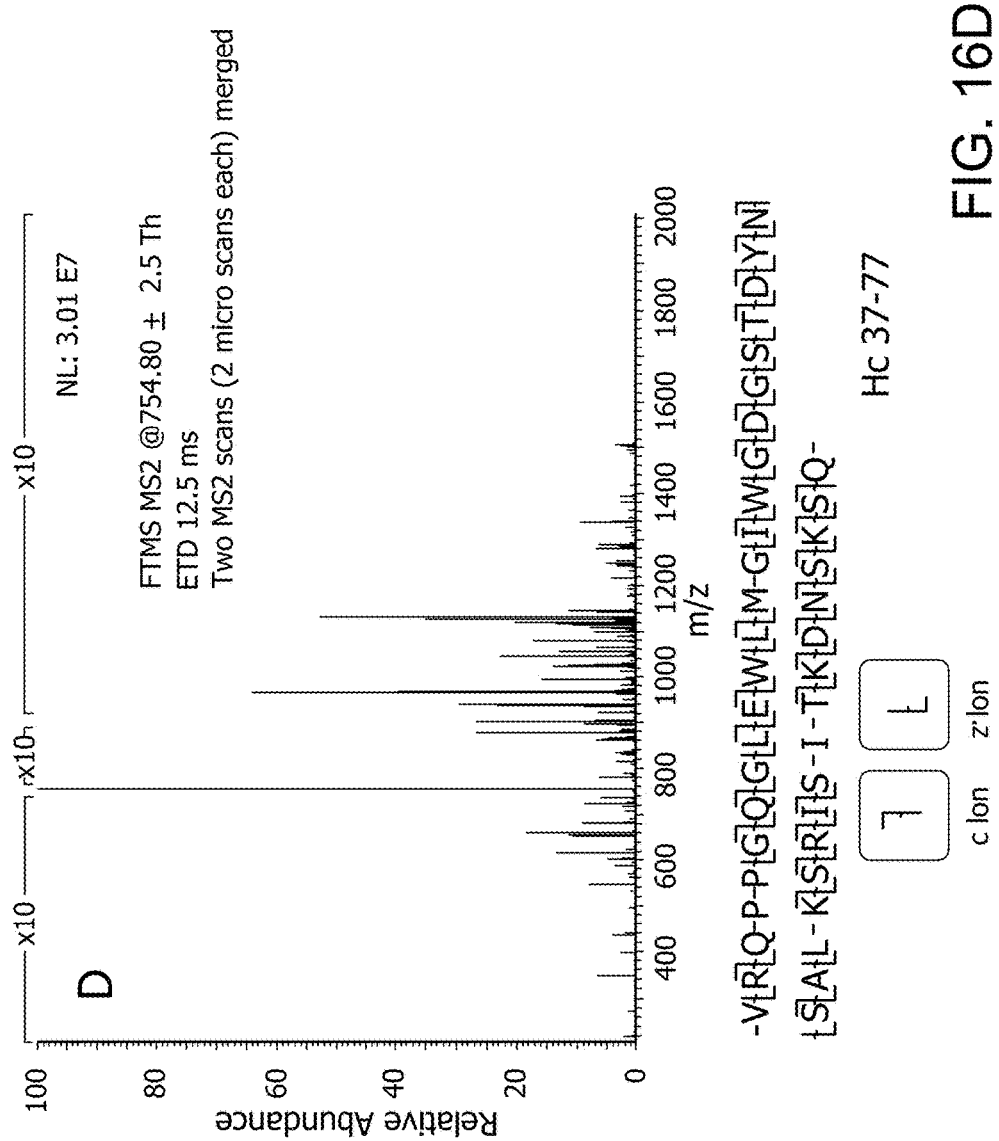

Fortunately, the aspergillopepsin I enzyme reactor has consistent activity in 8M urea at pH 3.9 for at least 1 hour (FIG. 14). Similar as for apomyoglobin, we tested several residence times for on-column digestion of alkylated mAb prepared in 8M urea, and found that 5.7 s generates mainly 3-9 kDa peptides with no noticeable undigested mAb Lc and Hc (FIG. 15). As mAb is much larger than apomyoglobin, simply targeting the base peak large peptides for MS/MS in Experiment II is not enough to obtain complete mAb sequence. After a quick screening of the most abundant large peptides along the LC gradient of Experiment I, we divided the full MS data into 8 segments as shown in FIG. 16. Converting the highly charged peptide ions in each segment to their neutral forms by Xtract facilitates the selection of major large peptides for the following MS/MS analysis. FIG. 16 illustrates this procedure using the 5th segment in Experiment I (i.e. Segment I-5). In this example, averaging the full MS data collected in Segment I-5 (FIG. 16C, gradient 72-79 min) generates a mixture of multiply charged peptide ions (FIG. 16A). Directly picking major large peptides from this complex spectrum is time consuming and inaccurate in estimating the peptide abundance. However, converting these highly charged ions into their neutral forms greatly simplifies the original MS data to 7 major peptides with 4-6 kDa MW (FIG. 16B). Calculating the m/z values of multiply charged ions based the MW values facilitates the identification of original ions for each of the 7 major peptides in FIG. 16A (each peptide marked with a specific label) as well as the localization of the corresponding peptide peak in the chromatogram (FIG. 16C). Using this procedure, we picked 39 most abundant peptides from Experiment I and re-grouped them into 11 new time segments according to their elution times for targeted ETD MS/MS in Experiment II. For example, Segment II-6 includes six peptides that elute close with each other (FIG. 16C), so the MS/MS settings in Segment II-6 includes 1 full Orbitrap MS scan followed by 6 ETD Orbitrap MS2 scans targeted on the 6 peptides, respectively. The 7 scan events repeat in Segment II-6 until Segment II-7 begins. FIG. 3D displays the ETD MS2 of one of the peptides (precursor ion m/z 754.8 with +6 charge state). Searching the fragment ions of this peptide against the reference mAb sequence using ProSightPC identified the peptide sequence as He 37-77.

With the multi-segment MS/MS method described above, our strategy revealed 98% sequence of mAb Lc (218 total amino acids) covered by 6 large peptides, and 94% sequence of mAb Hc (441 total amino acids) covered by 14 large peptides (FIG. 8).

Charge Enhancement on Cys Improves mAb Sequence Coverage by ETD.

Although ETD cleaves large peptide backbones generally more evenly and extensively compared to CAD, some large peptides with m/z>900 often yield low sequence coverage upon ETD due to limited number of charges (basic residues). Low sequence coverage of some peptides may lead to incomplete identification/verification of mAb CDRs.

Figure 2A:
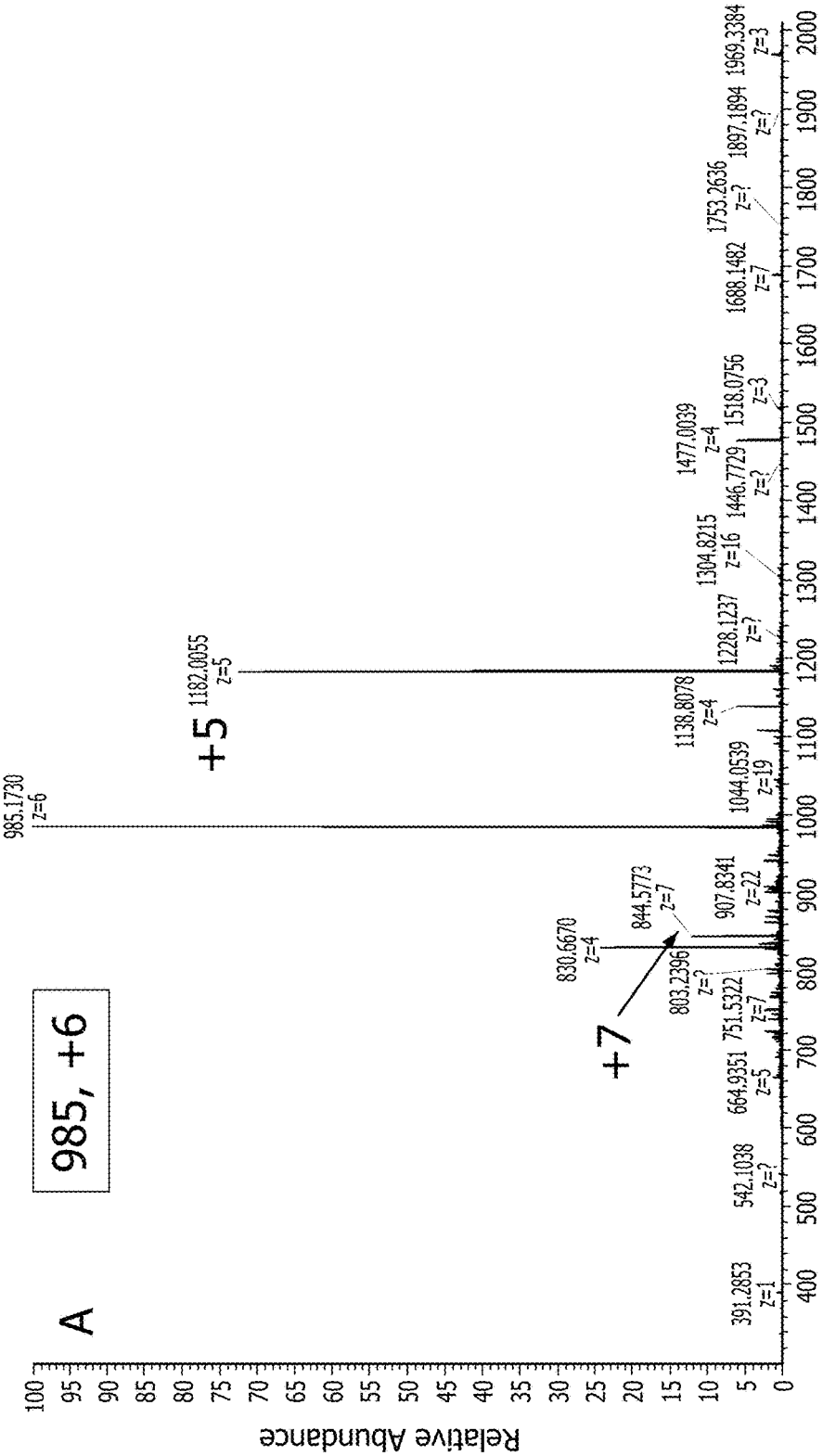
FIG. 2, comprising FIGS. 2A to 2E. Improvement of ETD on charge enhanced mAb Lc1-52. A-D: Charge state distribution (A, B) and the ETD (C, D) of peptide Lc1-52 with its Cys alkylated with (A, C) NAEM and (B, D) IAM. E: Sequence coverage of peptide Lc1-52 (SEQ ID NO:2) by ETD, or ETD and CAD. The underline indicates CDR1 of Lc.
Figure 2B:
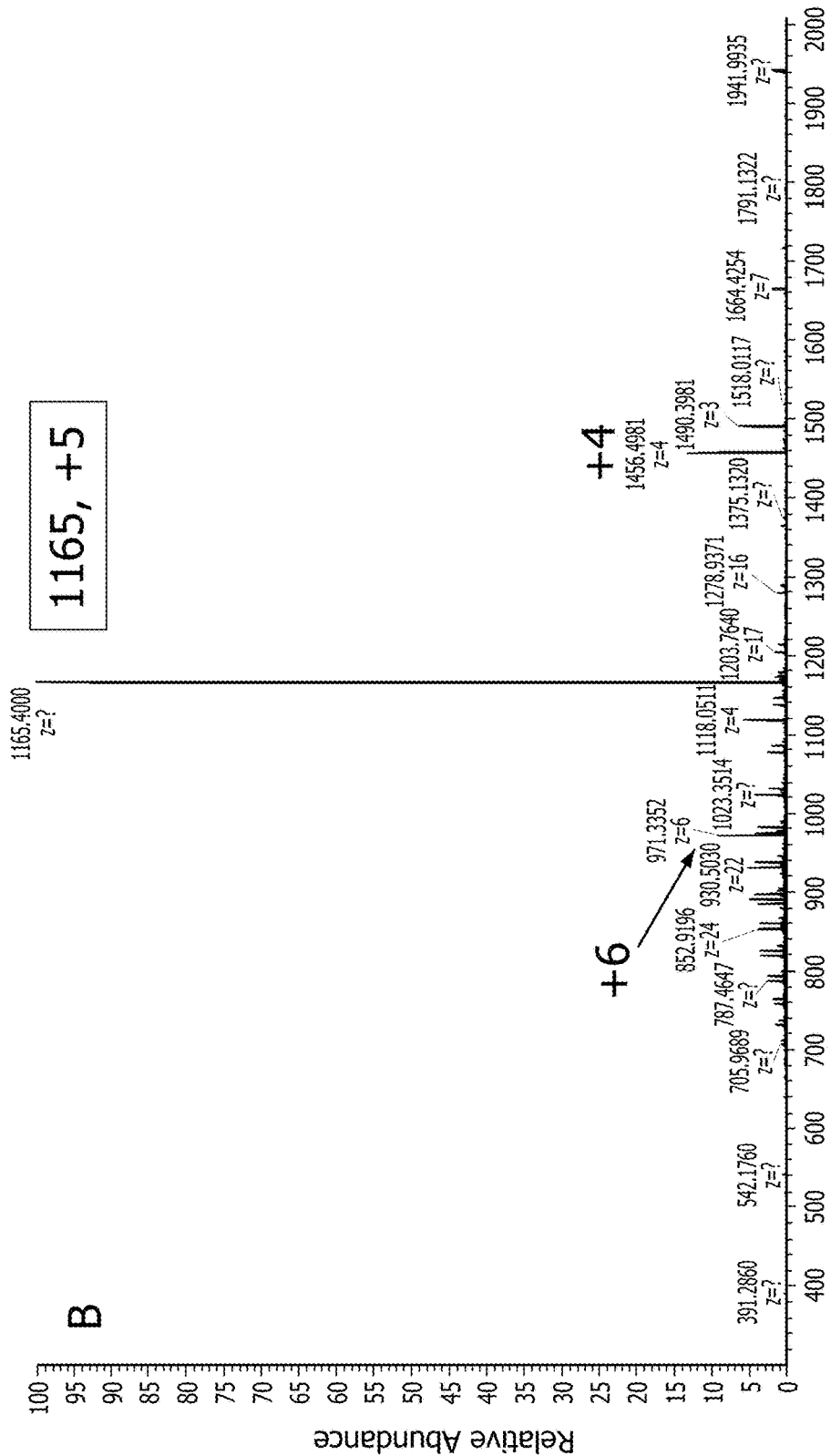
Figure 2C:
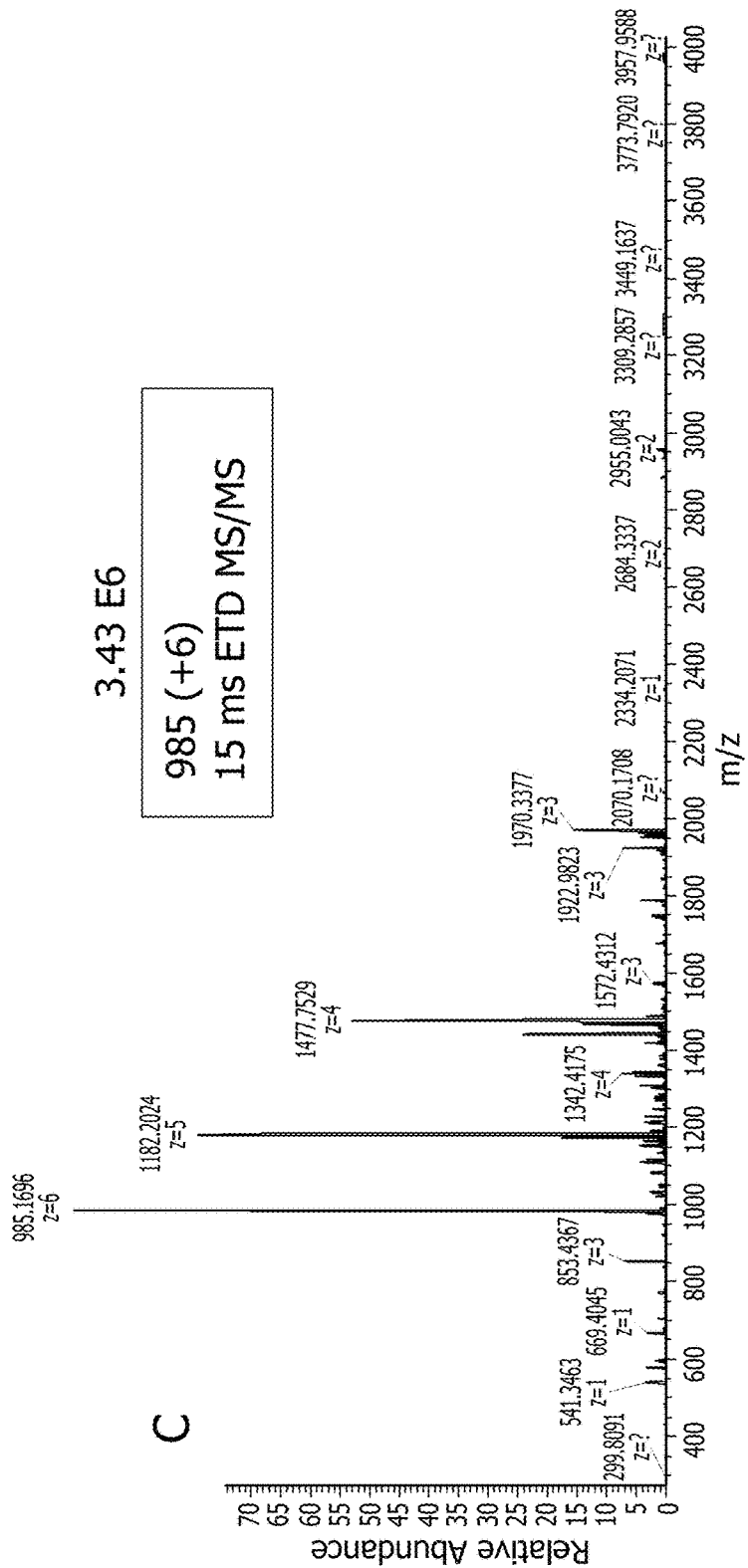
Figure 2D:
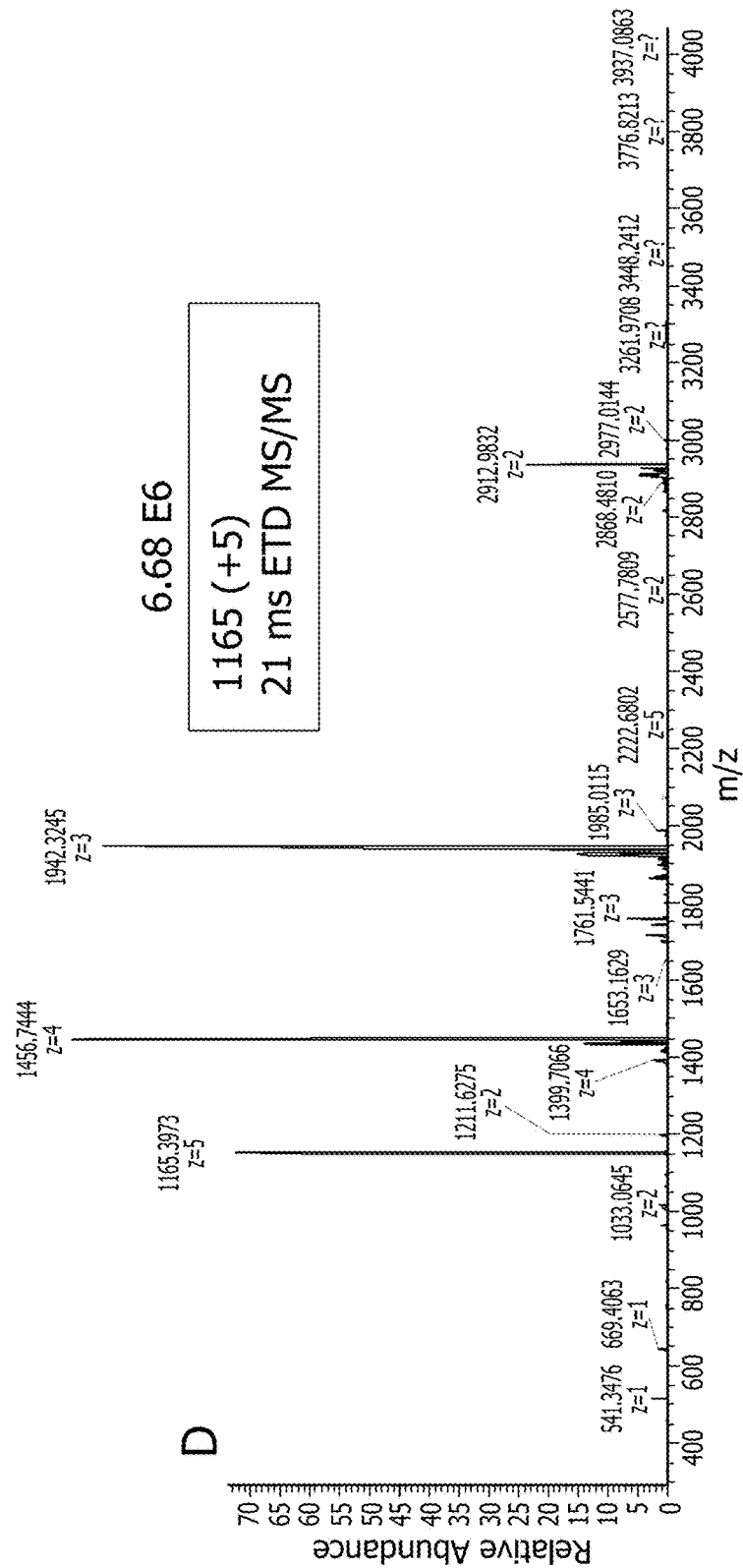
Figure 17:
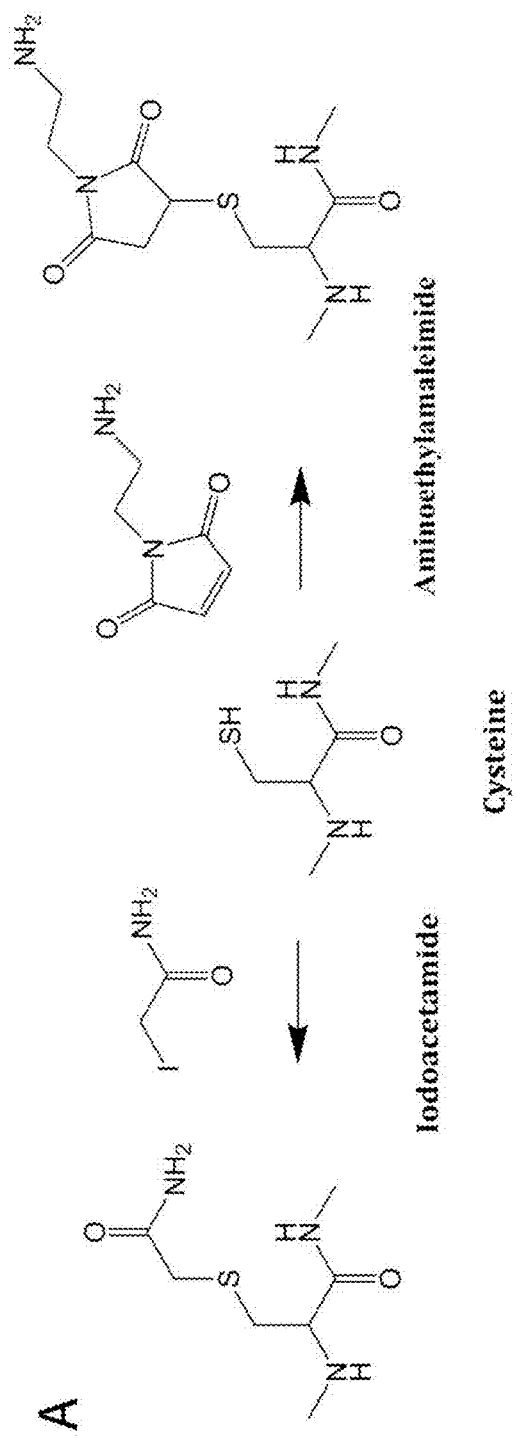
FIG. 17. Alkylation of cysteine side chain using iodoacetamide (IAM) and N-(2-aminoethyl) maleimide (NAEM).

Previous studies correlating antibody sequence with protein higher-order structure have shown that CDR1 and CDR3 of both Lc and Hc are in close approximation to Cys residues (19). In this work, to improve mAb sequence coverage, we improved ETD of Cys-containing peptides by alkylating mAb Cys residues with NAEM prior to protein digestion. This strategy introduces a primary amine (i.e. +1 charge once protonated) to the side chain of each Cys (FIG. 17), and can potentially enhance ETD of mAb sequence nearby Cys. For example, Lc1-52 (5767 Da) with its Cys derivatized by NAEM has +1 charge state higher compared to the traditional IAM-derivatized form (FIG. 2 A, B). Surprisingly, this modification improves the sequence coverage of L1-52 upon ETD by over two folds (FIG. 2E).

Many of the newly appeared c and z fragments come from CDR1 close to the Cys residue, suggesting the potential role of the aminoethyl group on Cys side chain in proton transfer during ETD. Similarly, alkylating the 5 Cys of Hc211-260 (5431 Da) with NAEM increases +3 charges on the peptide, and improves peptide sequence coverage from 53% to 73% compared to the IAM-derivatized form (FIG. 19).

Overall, this novel charge enhancement strategy significantly enhances ETD of the 4 most abundant Cys-containing peptides that make up the whole Lc. Sequence coverage of the 4 peptides upon ETD increases from 52.1% (112 ETD cleavages) to 79.1% (170 ETD cleavages), including 11 additional cleavage sites within CDRs (Table S1). Table S1 compares peptides having SEQ ID NOs: 2 and 9-18. Similarly, sequence coverage of the 7 most abundant Cys-containing Hc peptides upon ETD increases from 54.4% (202 ETD cleavages) to 56.9% (211 ETD cleavages), including 2 additional cleavages within CDRs. If considering both ETD and CAD, this charge enhancement strategy increases the sequence coverage of the 11 most abundant Cys-containing peptides from 89.3% (192 cleavages) to 94.0% (202 cleavages) for Lc, and from 83.6% (310 cleavages) to 85.4% (317 cleavages) for Hc (Table S1).

Identification of mAb PTMs.

Among the 39 large peptides sequenced by the multi-segment MS/MS (Experiments II and III) and ProSightPC search (with manual verification), 8 were identified to carry one or more PTMs. FIG. 3 displays an example, in which the full MS (after conversion to neutral form) of Segment I-3 includes three groups of colored major large peaks with Δ162.0528 Da monoisotopic mass difference between two neighboring peaks (FIG. 3A). This mass shift corresponds to addition of a hexose, suggesting the potential existence of N-linked glycan on these peptides (a common modification on mAb Hc). ETD of the peptide with MW 6708 Da (FIG. 3B, C, D) followed by ProSightPC search of the c and z ions reveal the peptide identity Hc299-319 with monoisotopic mass shift of 1444.5338 Da (corresponding to G0F) at N314 (FIGS. 3B, C, D). This Asn glycosylation site is also consistent with the known antibody Fc N-glycan motif Asn-X-Ser/Thr where X can be any amino acid except for Pro (20). The second peak with 6870 Da MW should correspond to the isoform with glycan G1F, and the third peak (7032 Da) to G2F isoform.

Another identified PTM is amidation at Hc138D. Extracted ion current corresponding to m/z 903.4500 (+8 ion for one of the selected major large peptides) shows three peaks near 25-27.5 min (FIG. 20). The monoisotopic mass of the stronger peak is 0.9736 Da lighter than that of the minor peak, suggesting the existence of amidation on Asp or Glu. CAD MS2 targeted on m/z 903.55 (from Experiment III) shows identical $y_1$-$y_{10}$ ions for the two peaks, while the 1 Da mass shift starts from $y_{11}$, confirming that the amidation occurred on Hc138D (FIG. 20).

Met oxidation occurs very often in mAb and is an indicator of mAb stability. The multi-segment MS/MS strategy identified two Met sites with high-level oxidation (Lc Met4 and Hc Met304). To identify low level Met oxidation, we performed extra MS/MS experiments targeted on some low level peptides with their monoisotopic mass Δ15.9949 Da higher than the sequenced large peptides containing Met. Table 1 lists all the PTMs identified in this work.

Localization of mAb Disulfides.

Figure 9B:
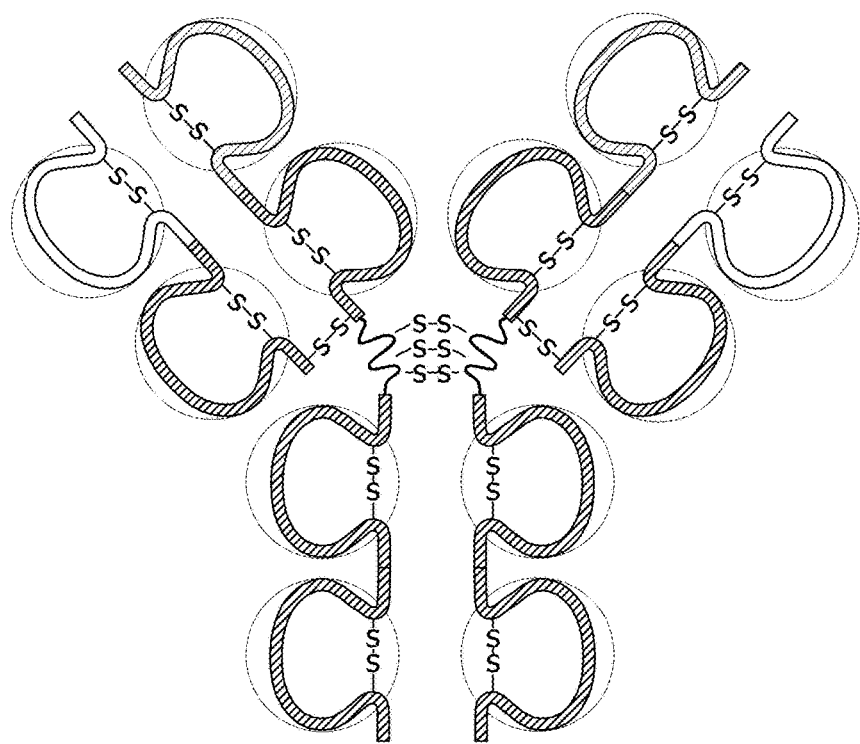
Figure 11A:
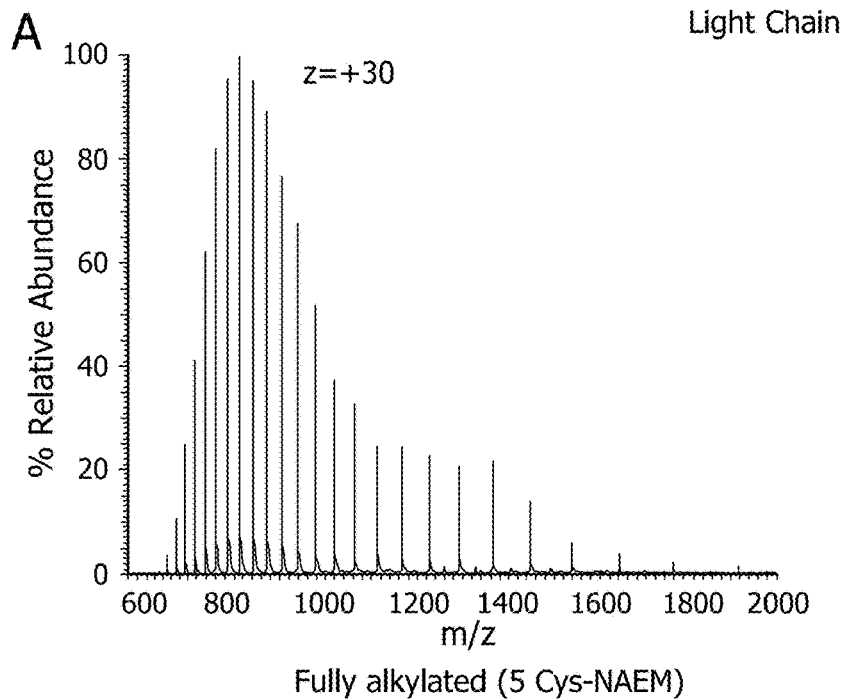
FIG. 11, comprising FIGS. 11A to 11D. Comparison of the charge state distributions of the fully (A and C) and partially (B and D) alkylated IgGLc (A and B) and He (C and D) obtained by online LC-LTQ MS, with the most abundant charge state (z) labeled in each MS spectrum. Aminoethyl-maleimide (NAEM) was used as the alkylation reagent.
Figure 11B:
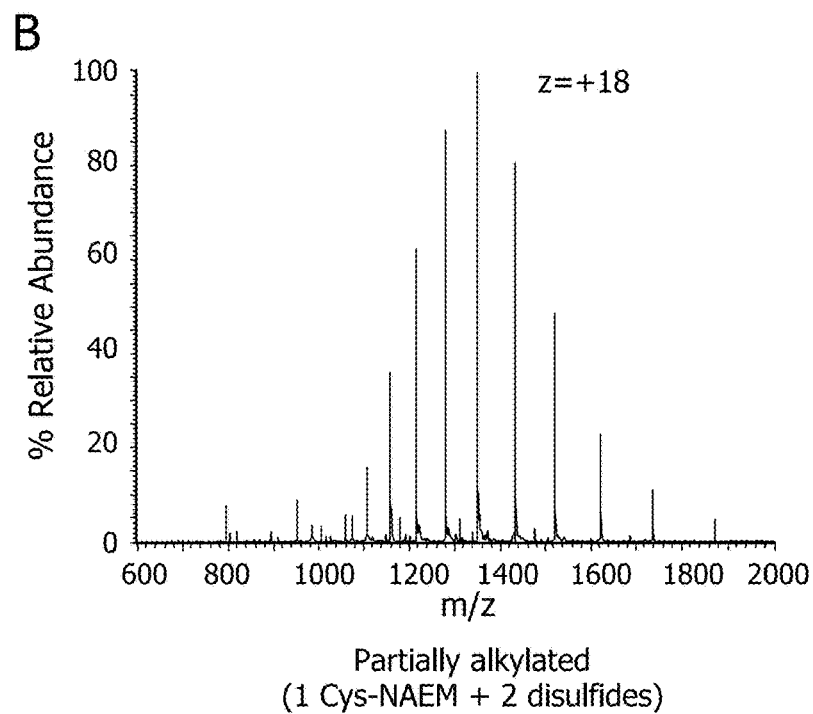
Figure 11C:
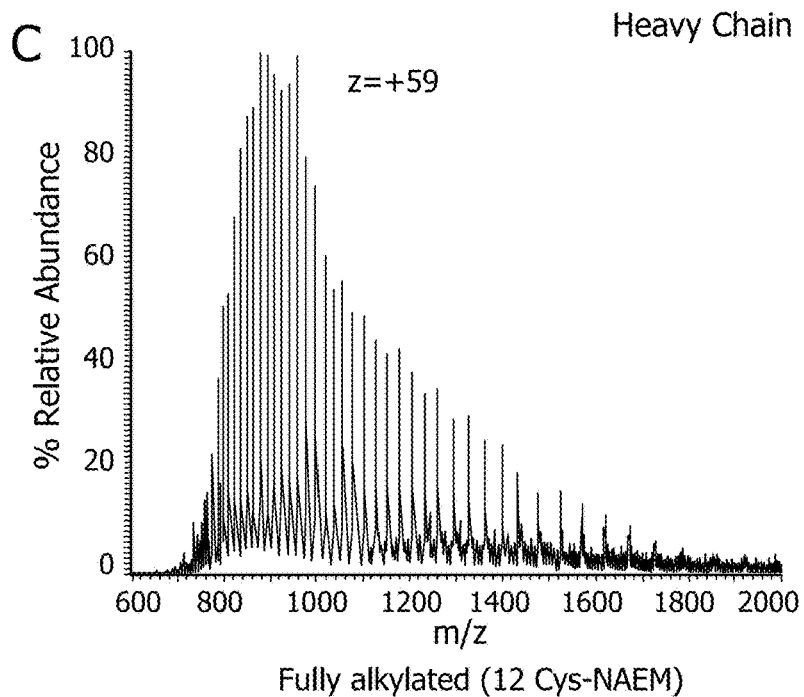
Figure 11D:
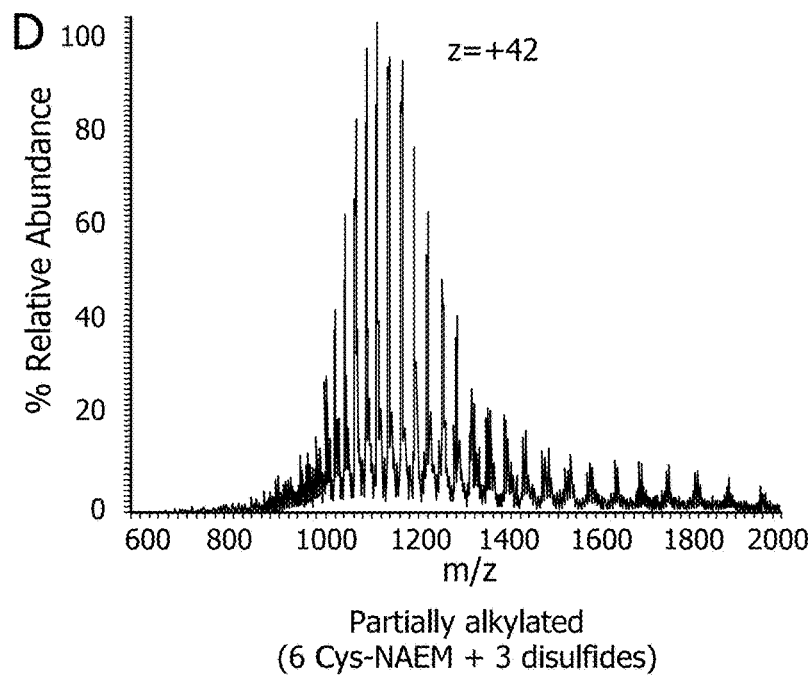

To characterize the disulfide linkages within mAb, we performed on-column digestion of the denatured intact mAb to produce disulfide-containing peptides. Compared to disulfide-reduced mAb, intact mAb requires longer digestion time to hydrolyze into peptides due to its rigid secondary structures supported by over a dozen of disulfides (FIG. 9). Moreover, some mAb domains are more easily digested than other domains, depending on their solvent accessibility due to its compact 3D structure. For the above reasons, there is no optimized on-column digestion time that can evenly cleave the whole mAb into several large peptides with similar sizes (as found for reduced/alkylated mAb). Instead, extending the digestion time results in detectable large peptides come firstly from the terminal domains of mAb Lc and He, then from the domains in the inner portion of mAb.

Figure 18A:
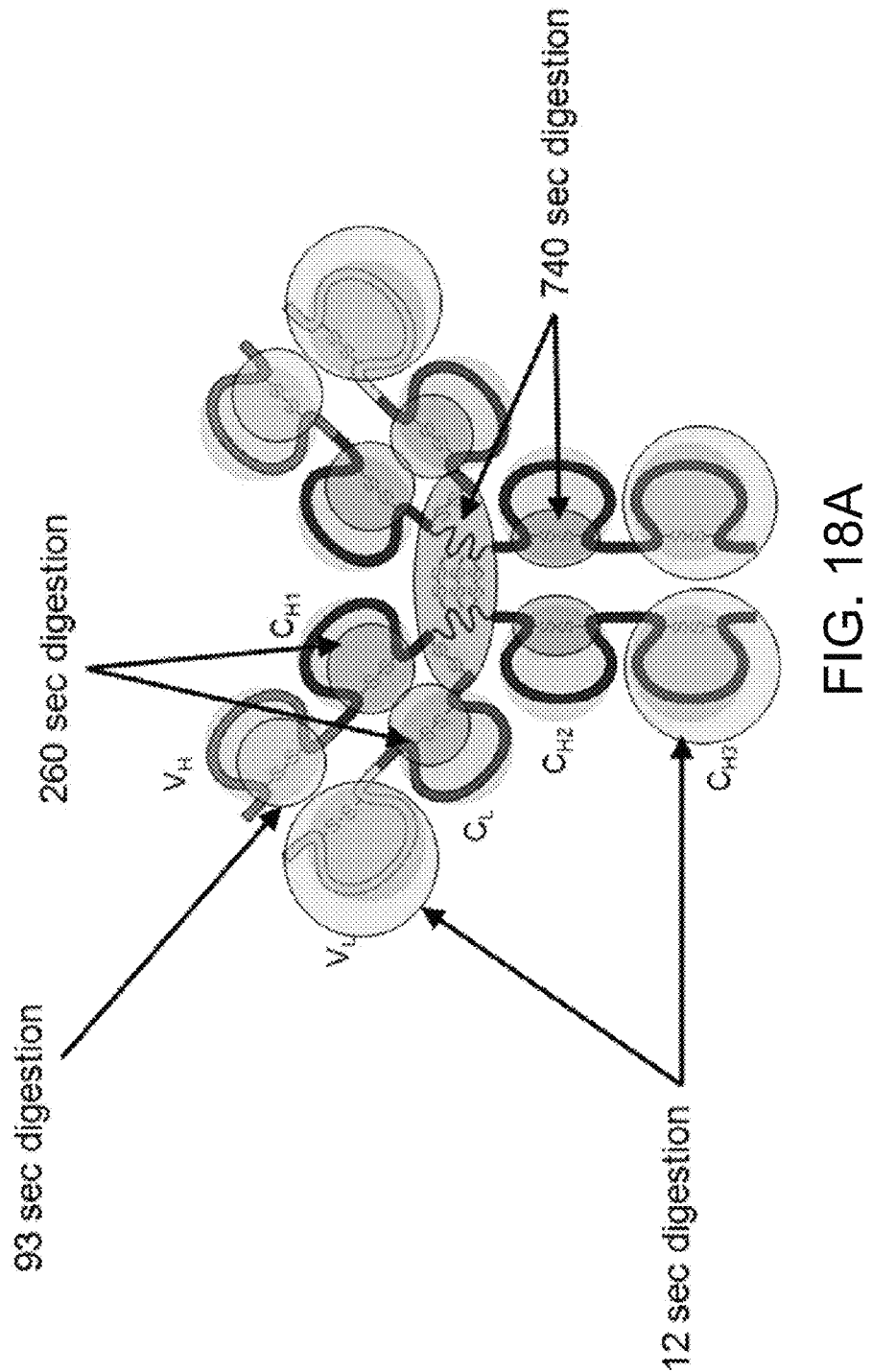
FIG. 18, comprising FIGS. 18A to 18B. Overview of the peptides used to map the location of disulfides in mAb structure (A) and their amino acid sequence (arrows indicating hydrolysis sites) (B). (SEQ ID NO:6—Light Chain; SEQ ID NO:7—Heavy Chain).
Figure 19A:
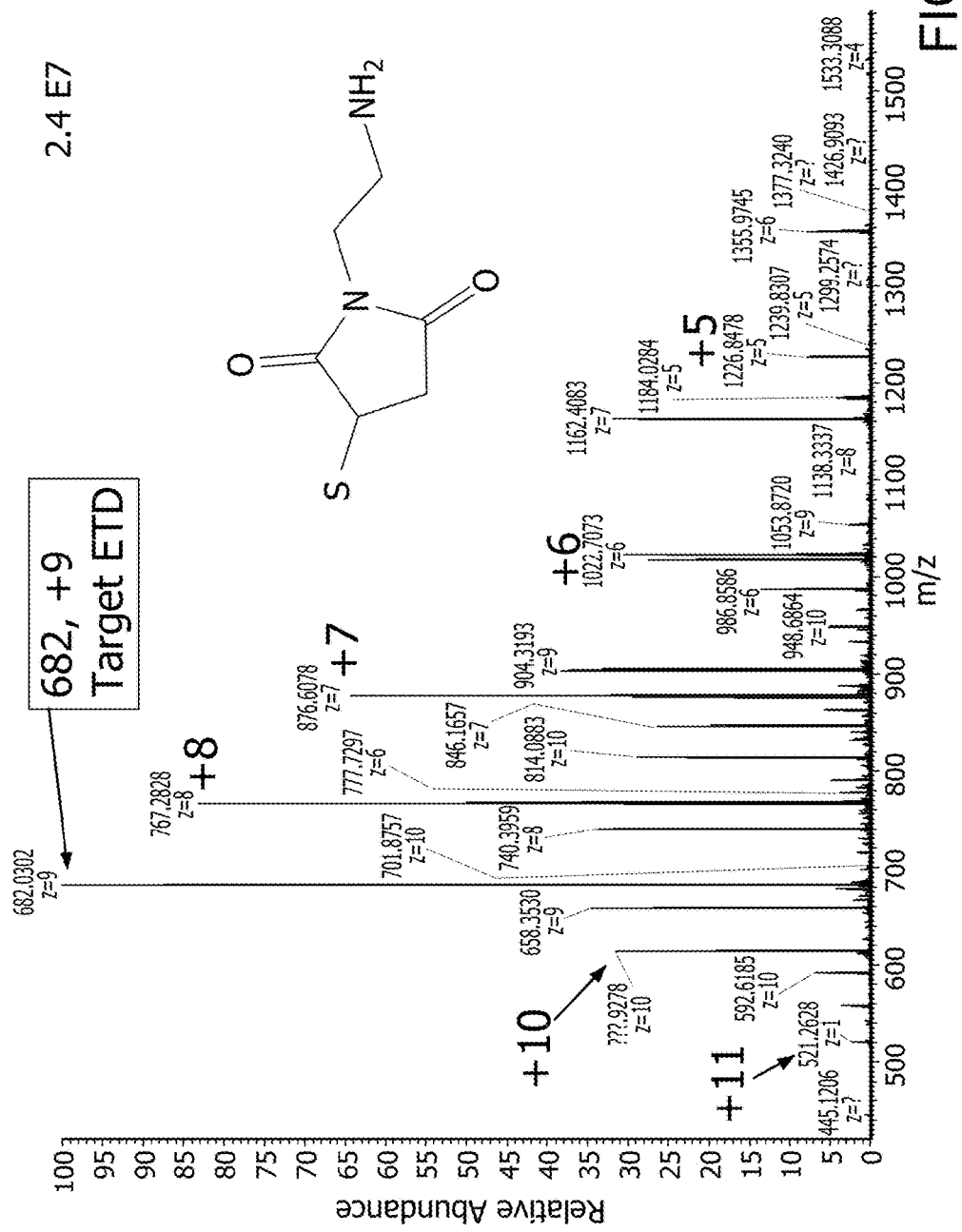
FIG. 19, comprising FIGS. 19A to 19D. Comparison of ETD MS2 generated from NAEM- and IAM-derivatized Cys-containing peptides. Charge state distribution (A, B) and the ETD (C, D) of peptide H211-260 with its 5 Cys alkylated with (A, C) NAEM and (B, D) IAM.
Figure 19B:
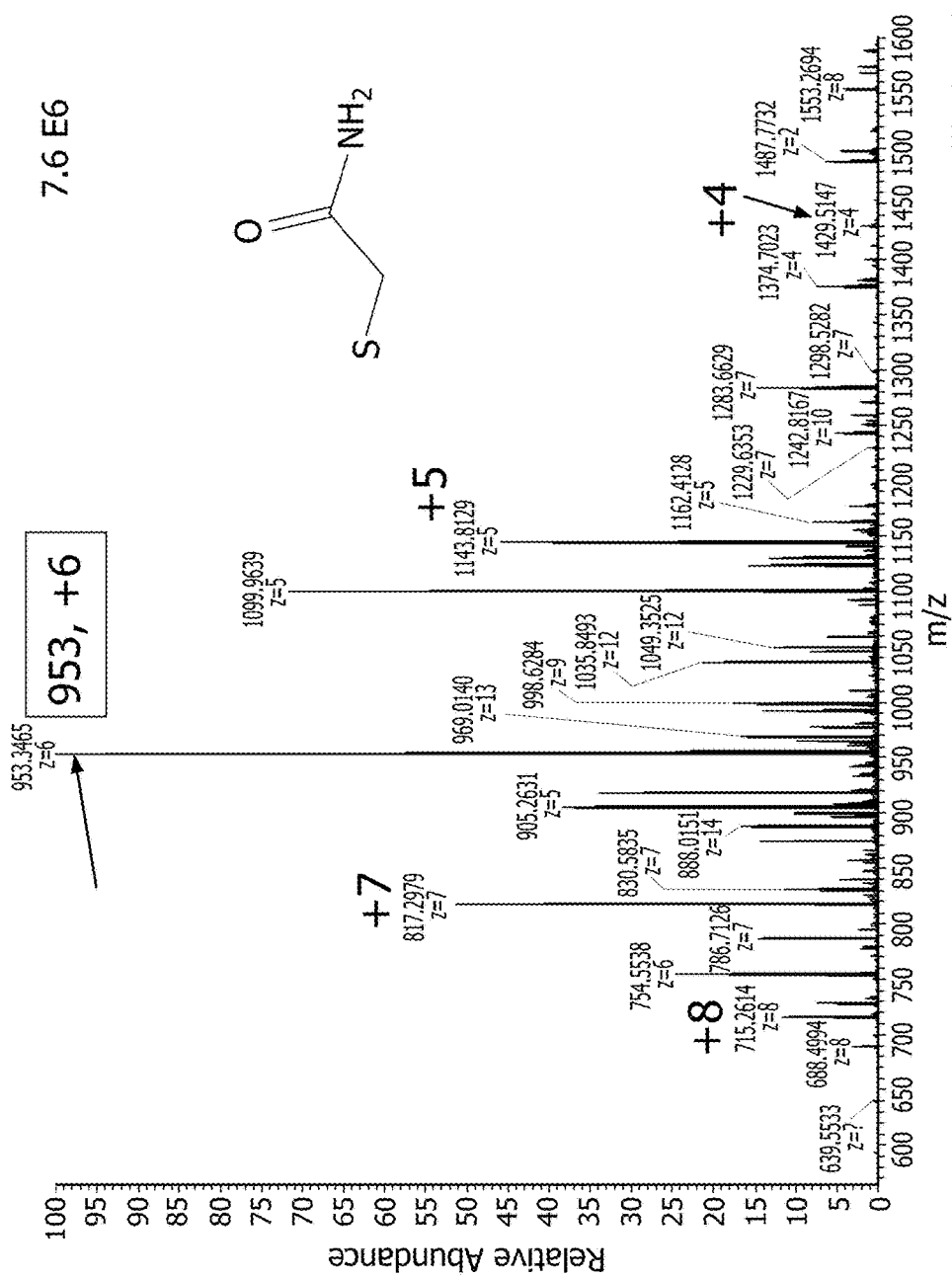
Figure 19C:
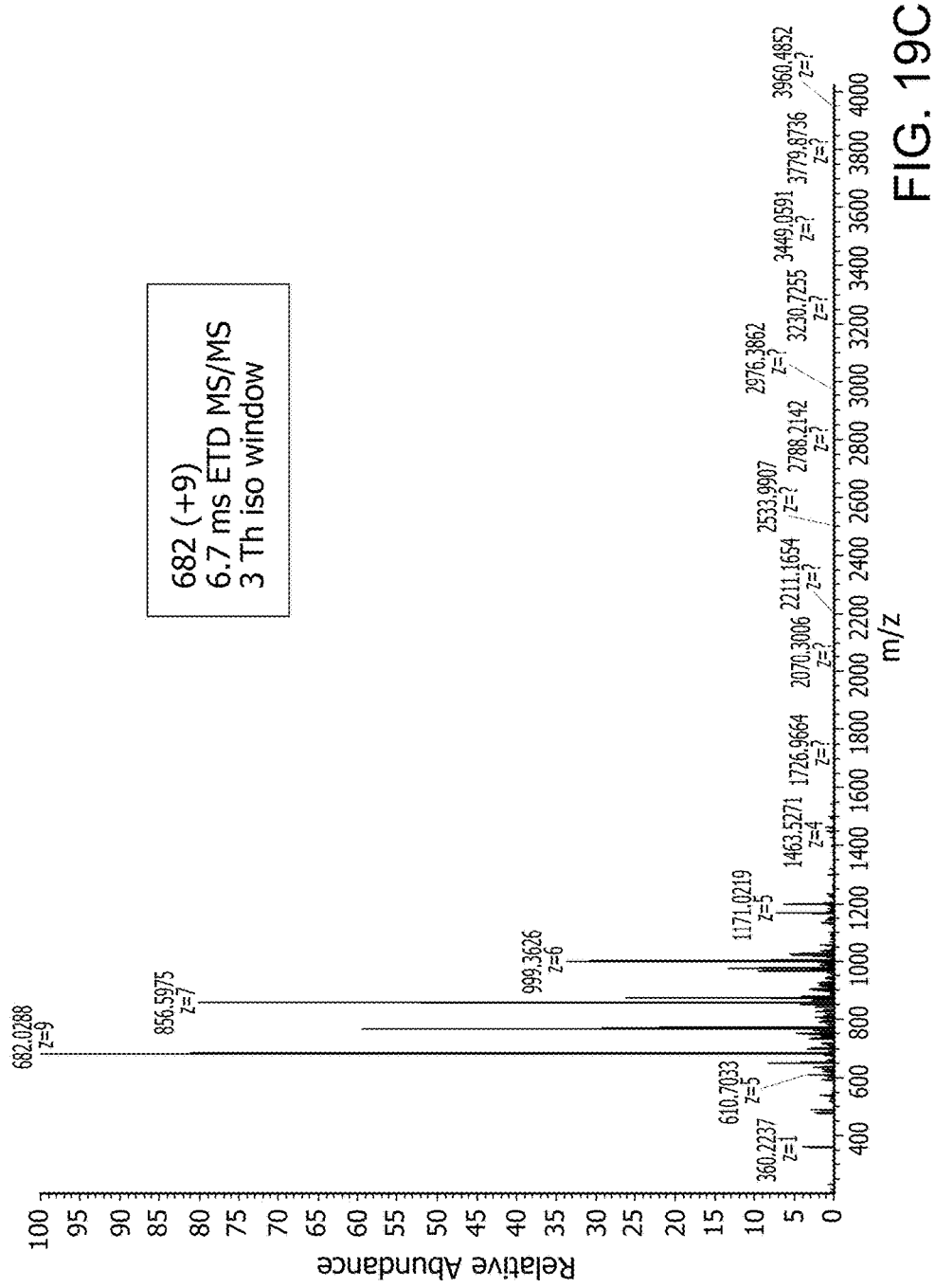
Figure 19D:
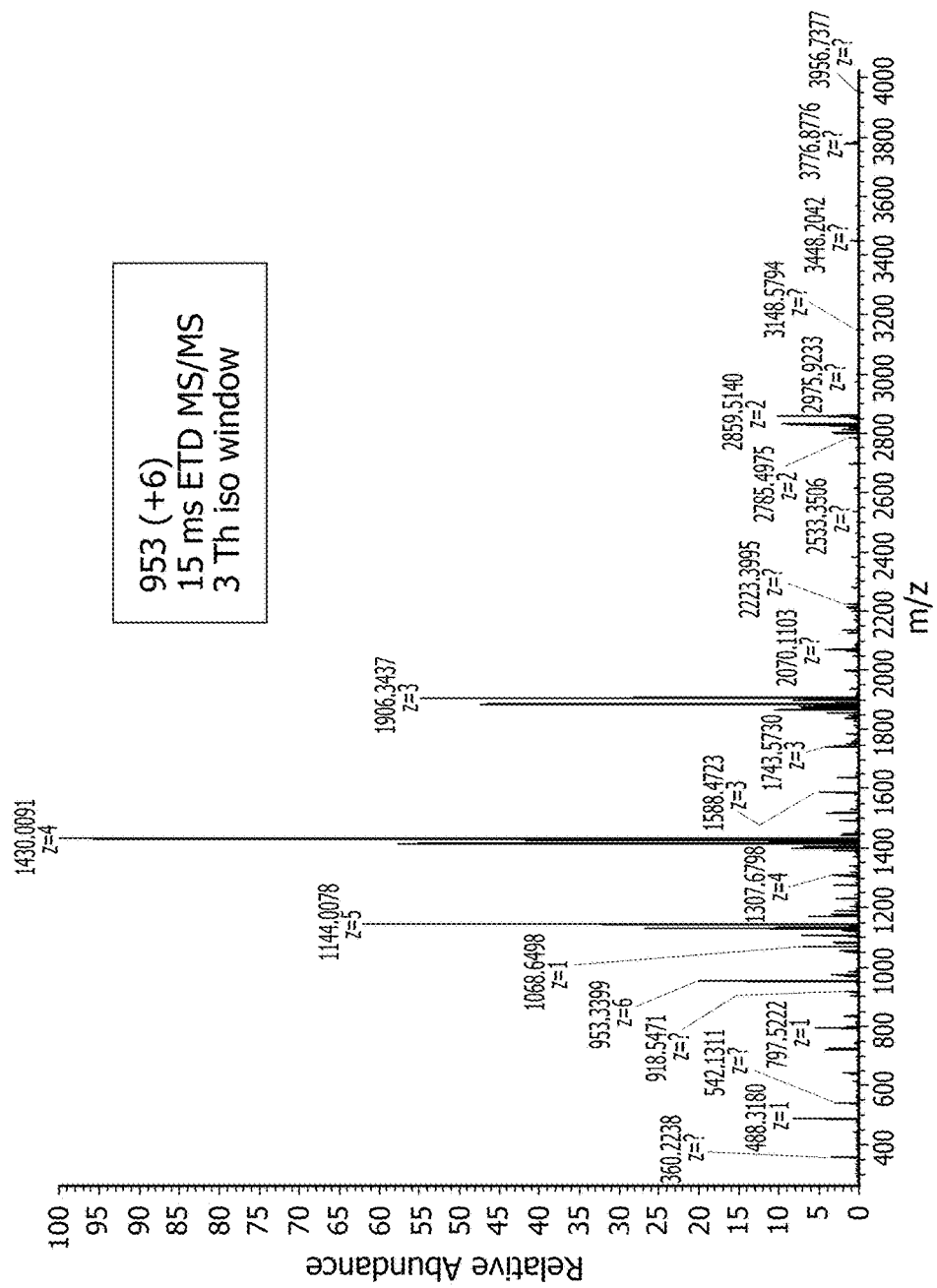
Figure 20A:
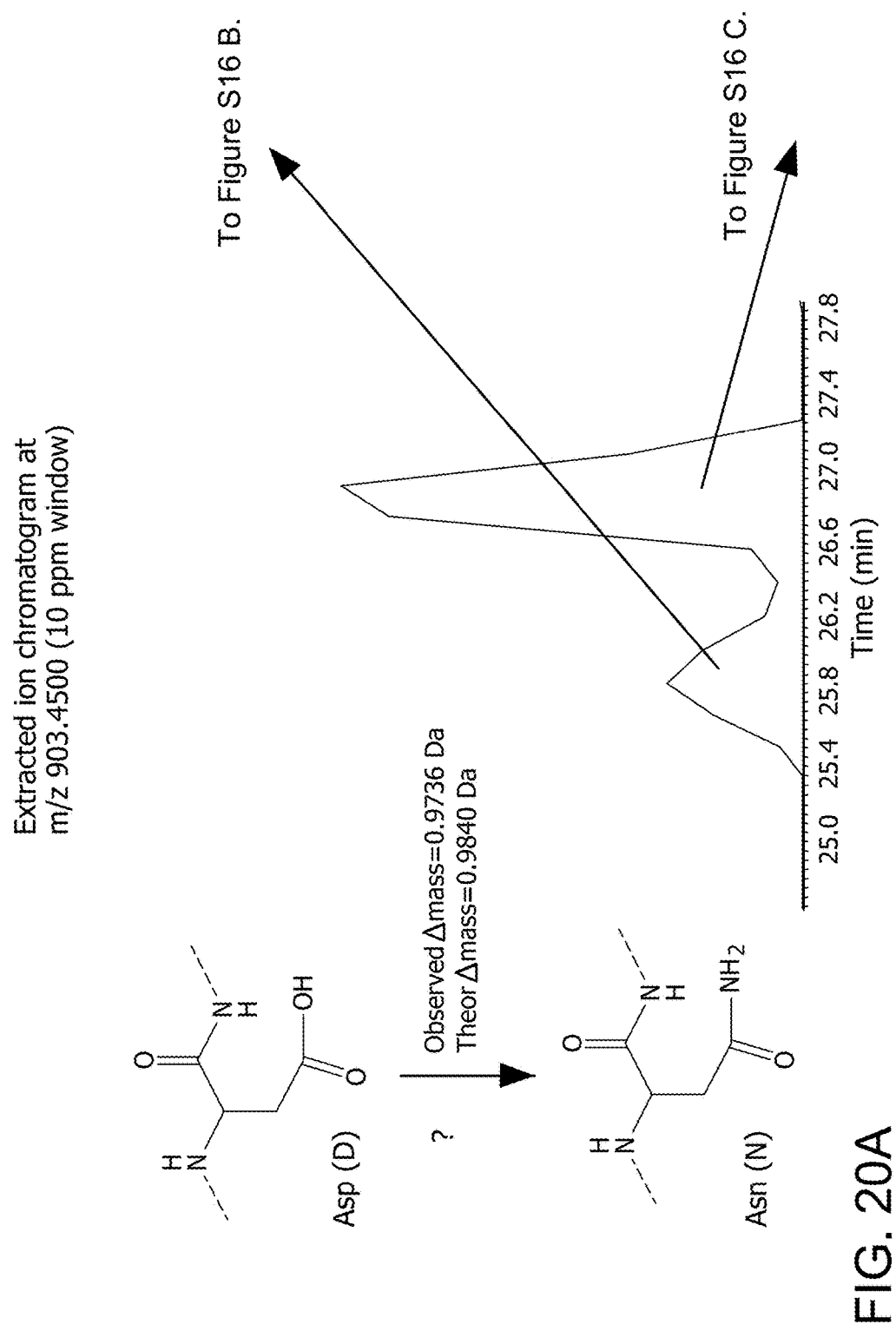
FIG. 20, comprising FIGS. 20A to 20F. Identification of mAb PTMs. Amidation of Hc138D evidenced by full Orbitrap MS (A, B, C) and CADOrbitrap MS2 (D, E, F; upper sequence of F-SEQ ID NO:19; lower sequence of F-SEQ ID NO:20).
Figure 20B:
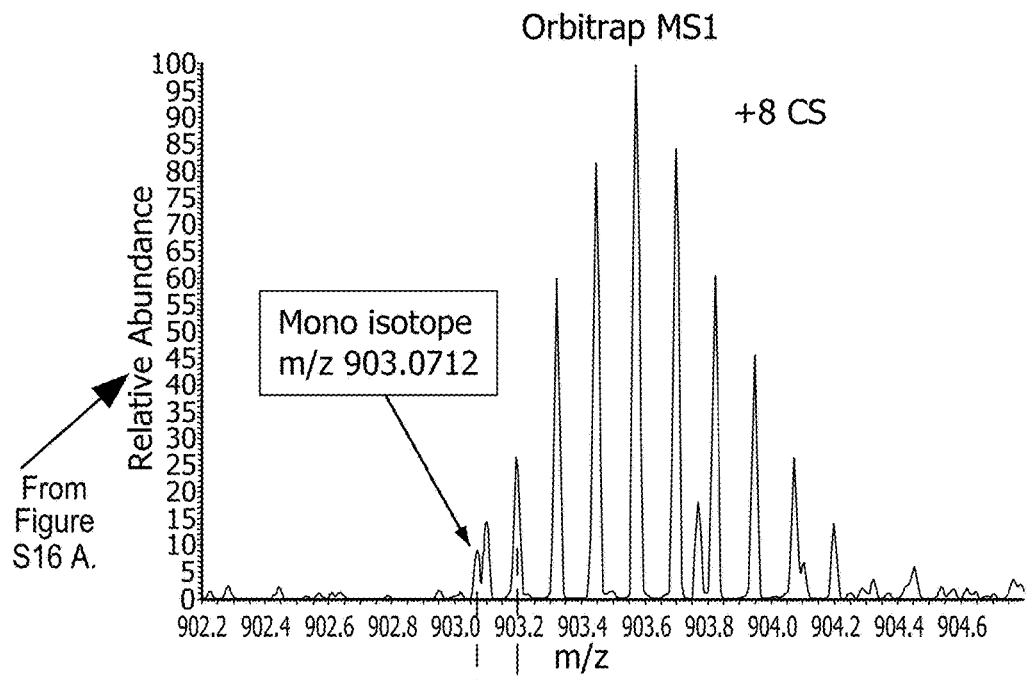
Figure 20C:
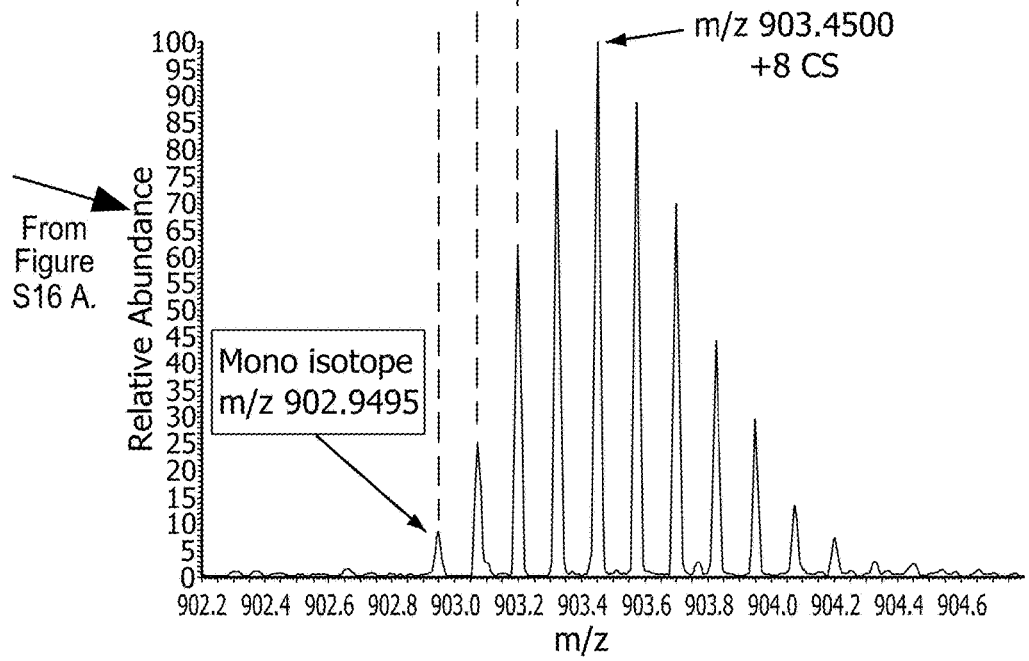
Figure 20D:
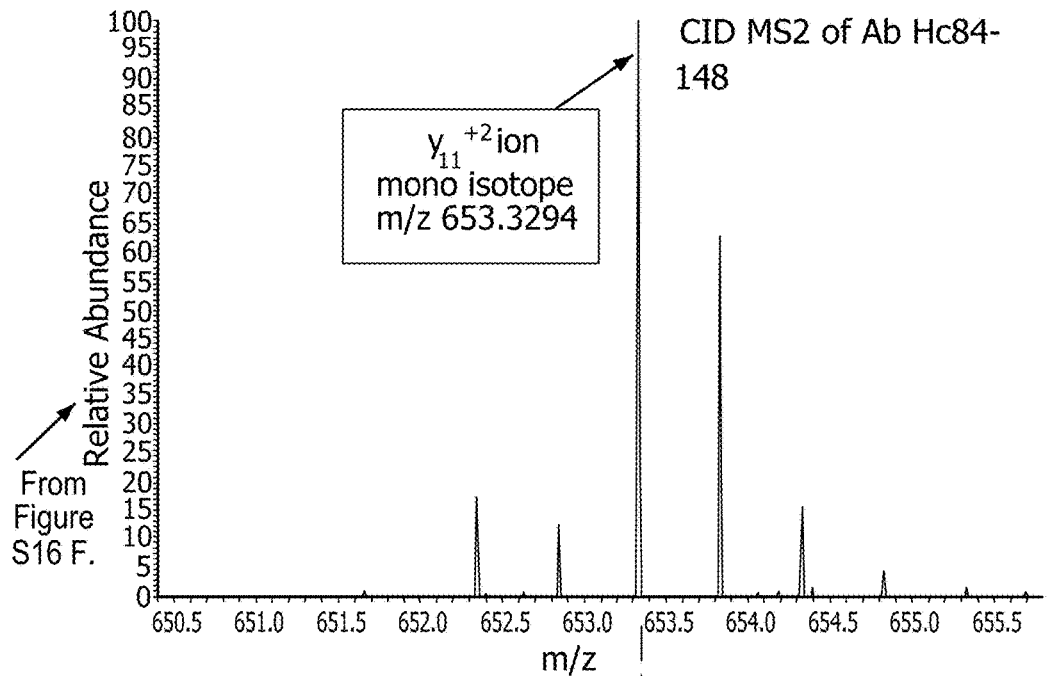
Figure 20E:
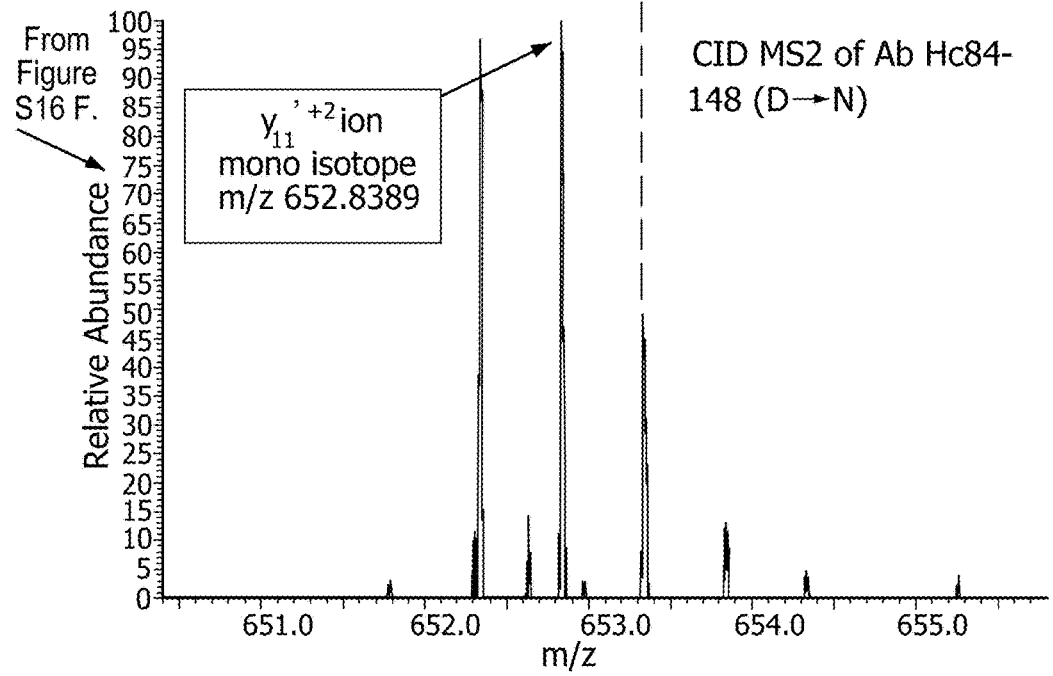
Figure 20F:
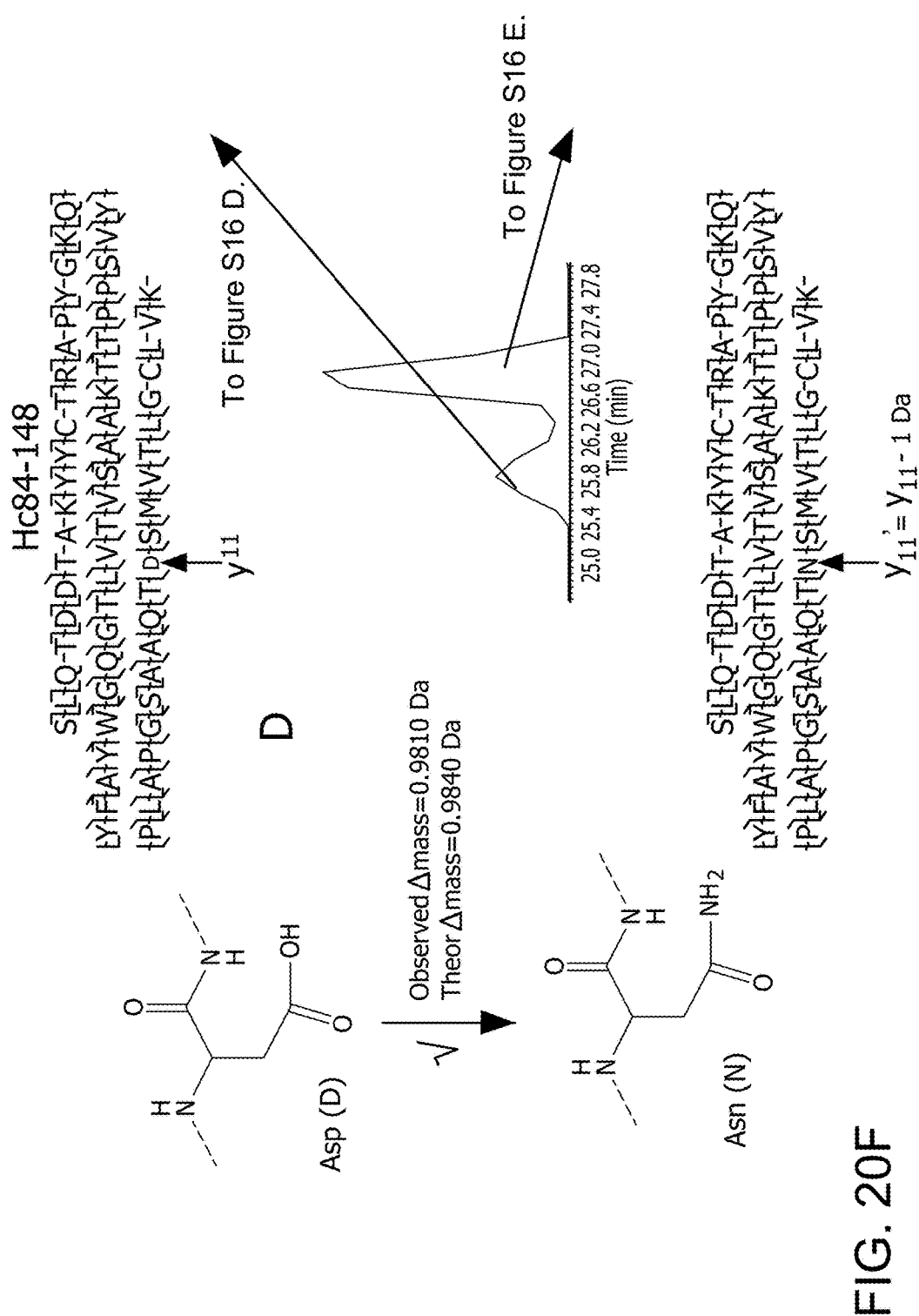
Figure 21A:
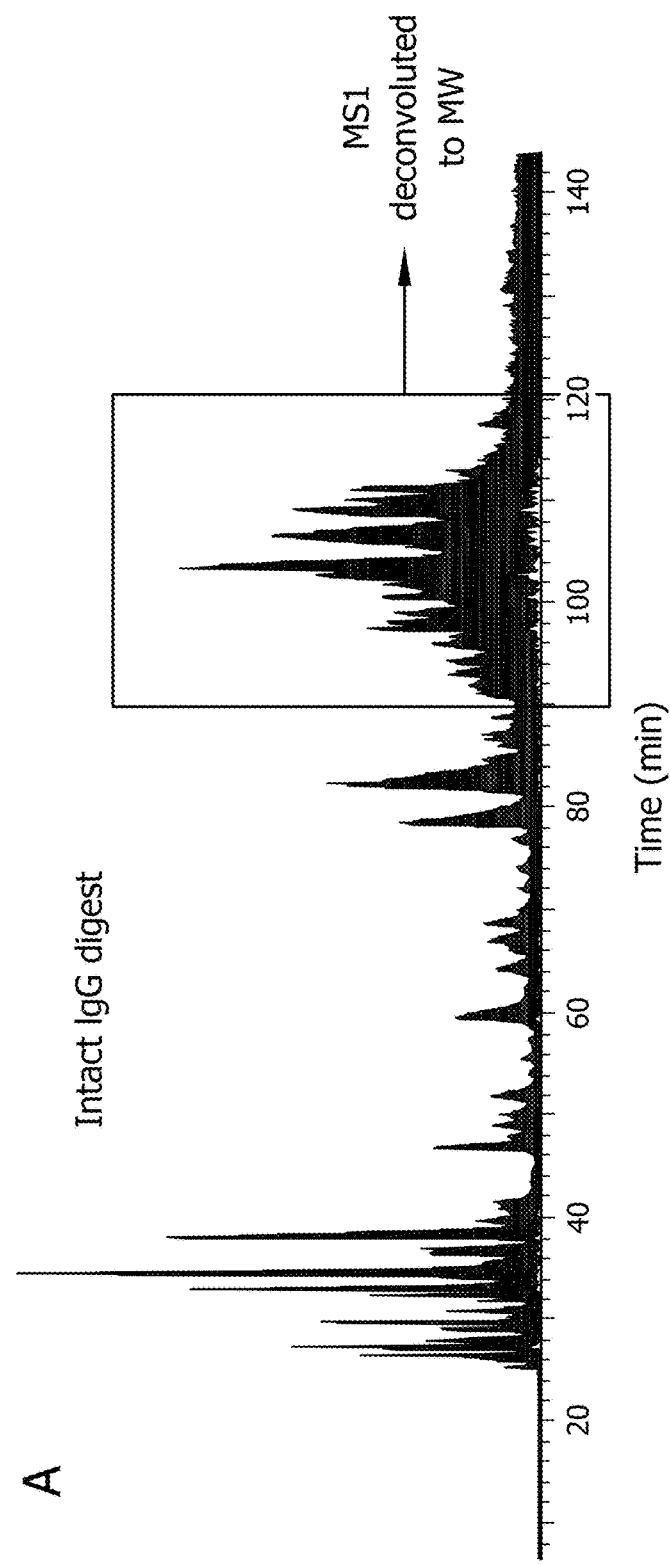
FIG. 21, comprising FIGS. 21A to 21E. Localization of mAb disulfides. Generation of VL and CH3 domains to localize their disulfides by 12 s on-column digestion of intact mAb dissolved in 8M urea. A and B present the total ion current of LC-MS of the resulting digest with (B) and without (A) disulfide reduction. C and D present the MW (m/z where z=1) of the major large peptides eluted in A and B, respectively. ETD was performed on the major disulfide peptides to identify their sequences as labeled in C. These disulfide peptides do not appear in D due to disulfide reduction. E presents the extracted ion current of the disulfide peptides in VL and CH3.
Figure 21B:
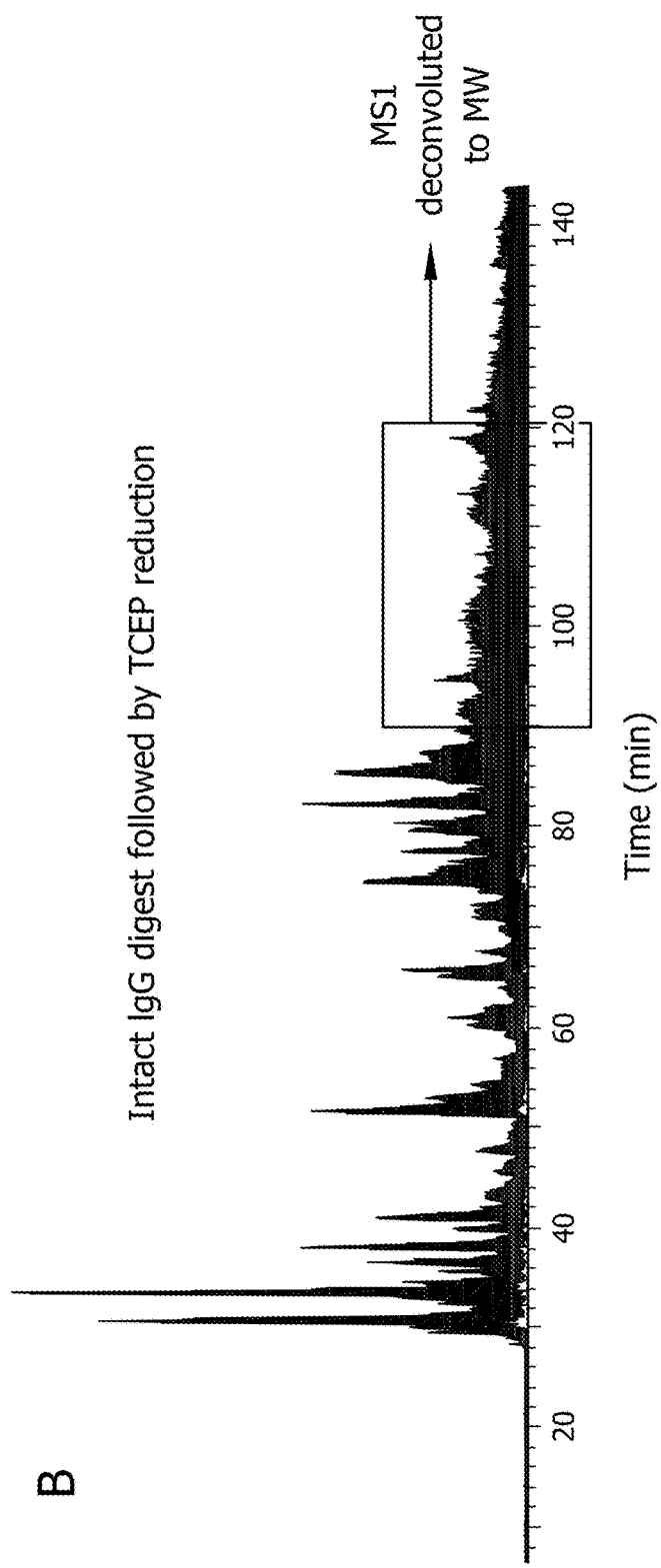
Figure 21C:
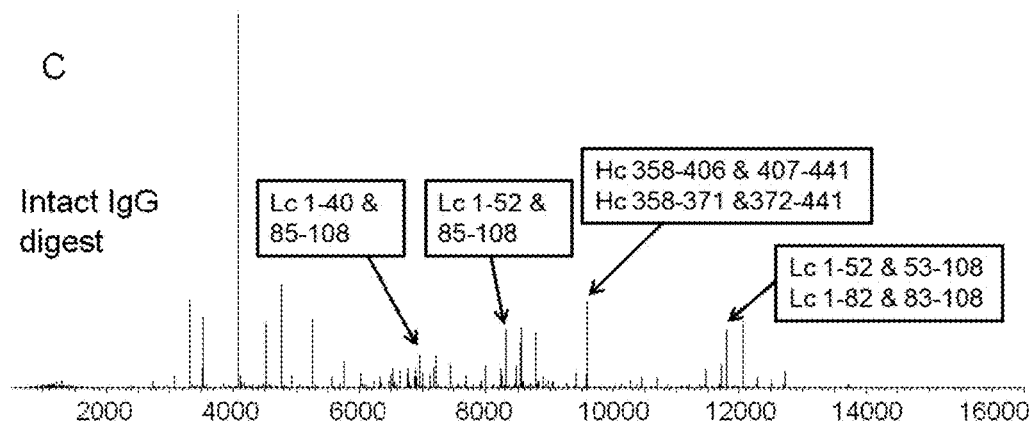
Figure 21D:
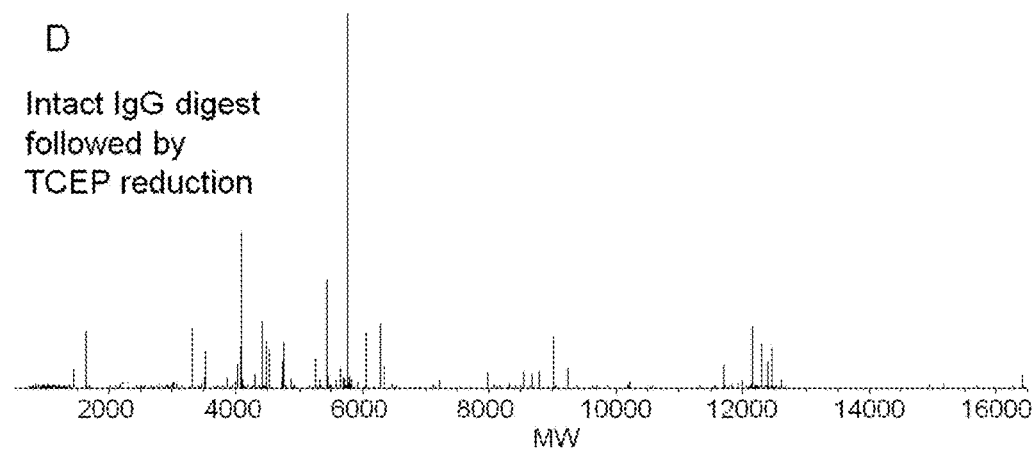
Figure 21E:
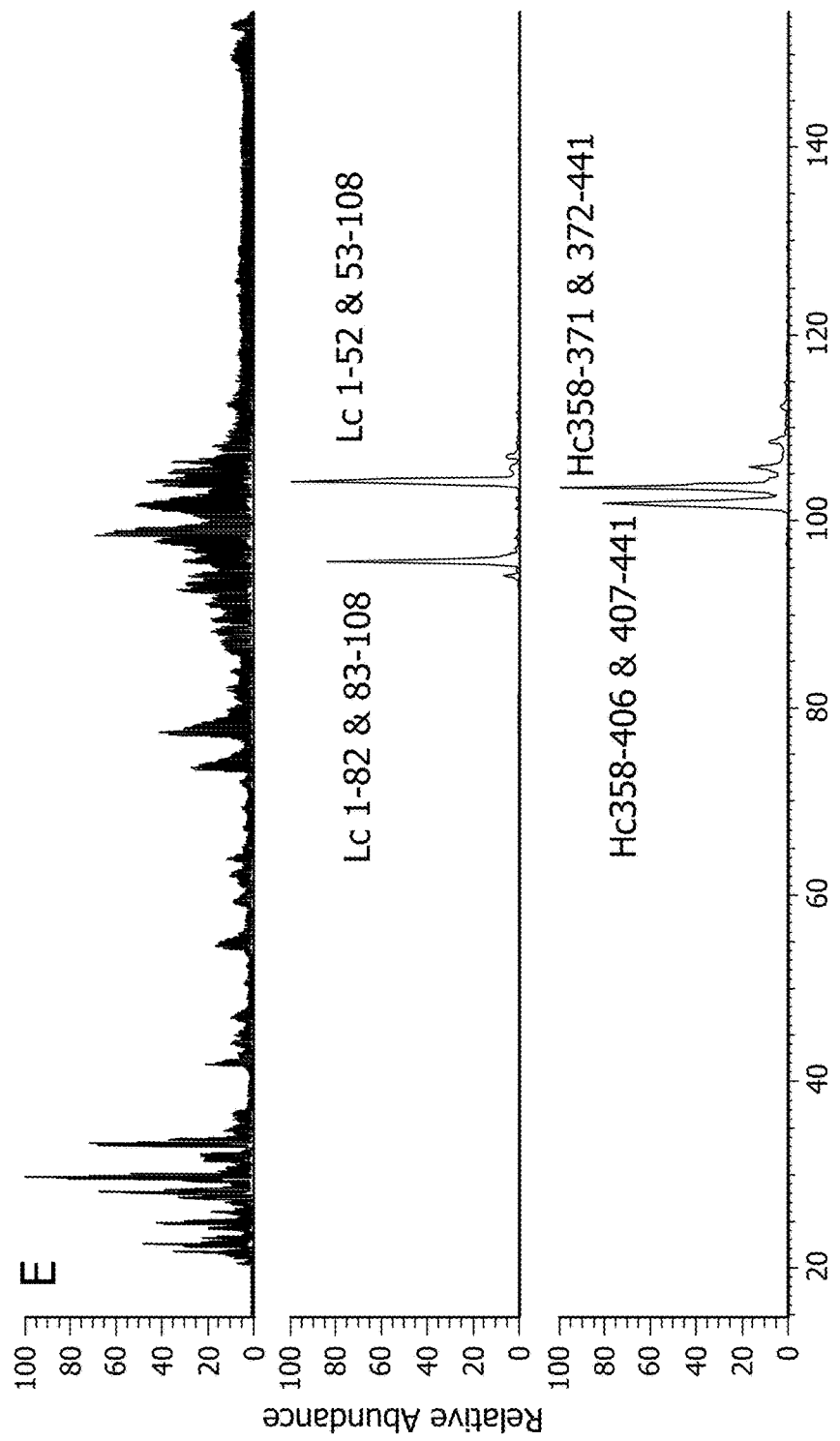
Figure 22A:
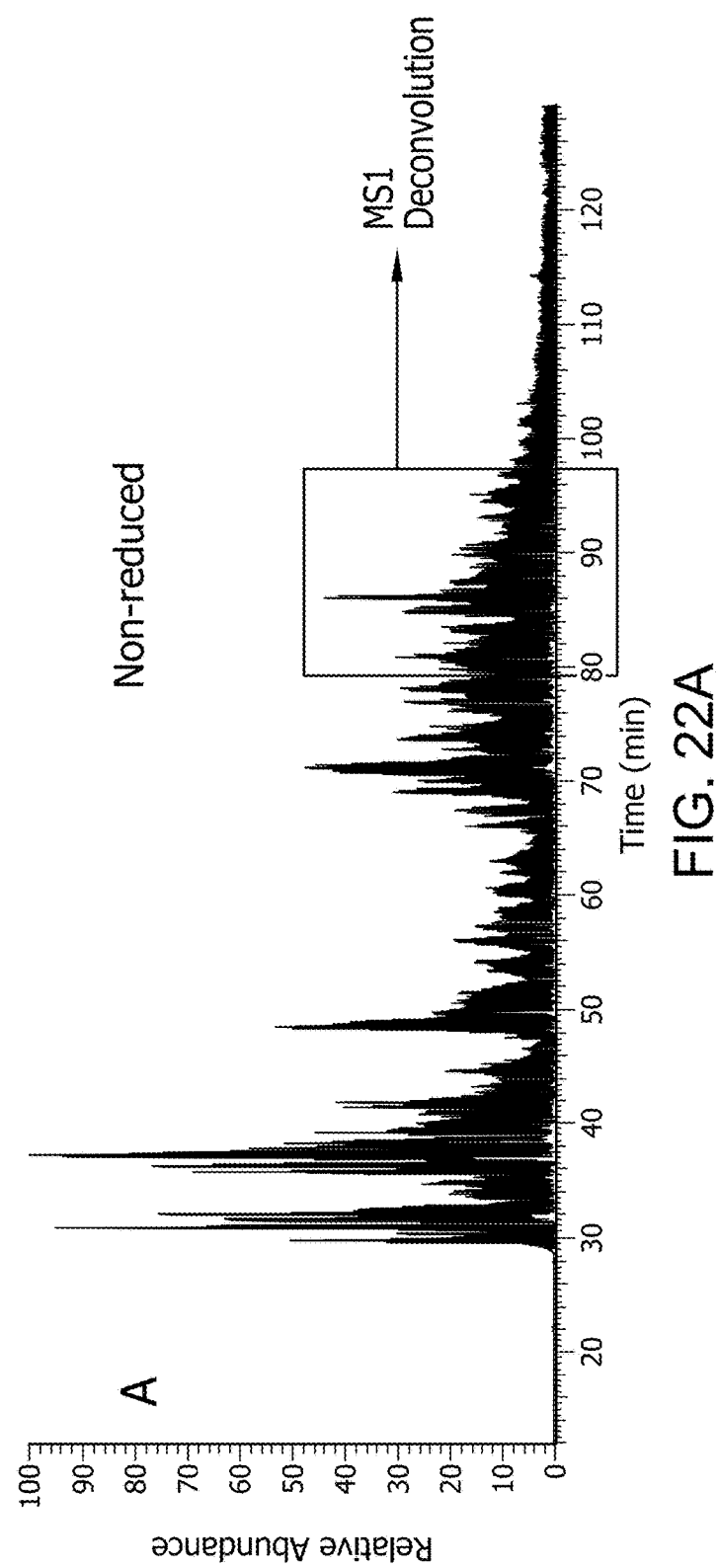
FIG. 22, comprising FIGS. 22A to 22D. Generation of disulfide peptides in $V_H$ by 93 s on-column digestion of intact mAb dissolved in 8M urea. A and B present the total ion current of LC-MS of the resulting digest with (B) and without (A) disulfide reduction. C and D present the MW (m/z where z=1) of the major large peptides eluted in A and B, respectively. ETD was performed on the major disulfide peptides to identify their sequences as labeled in C. These disulfide peptides do not appear in D due to disulfide reduction.
Figure 22B:
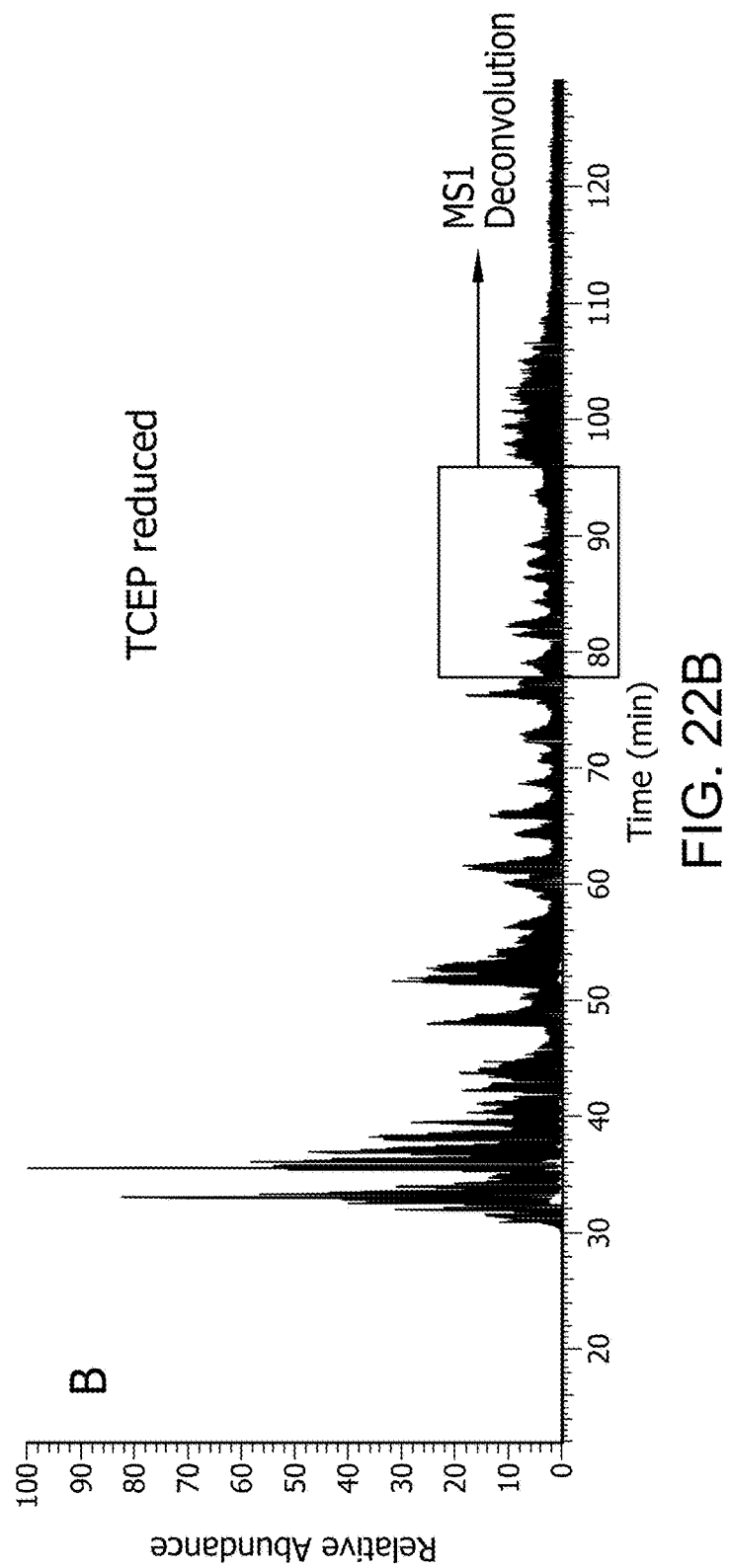
Figure 22C:
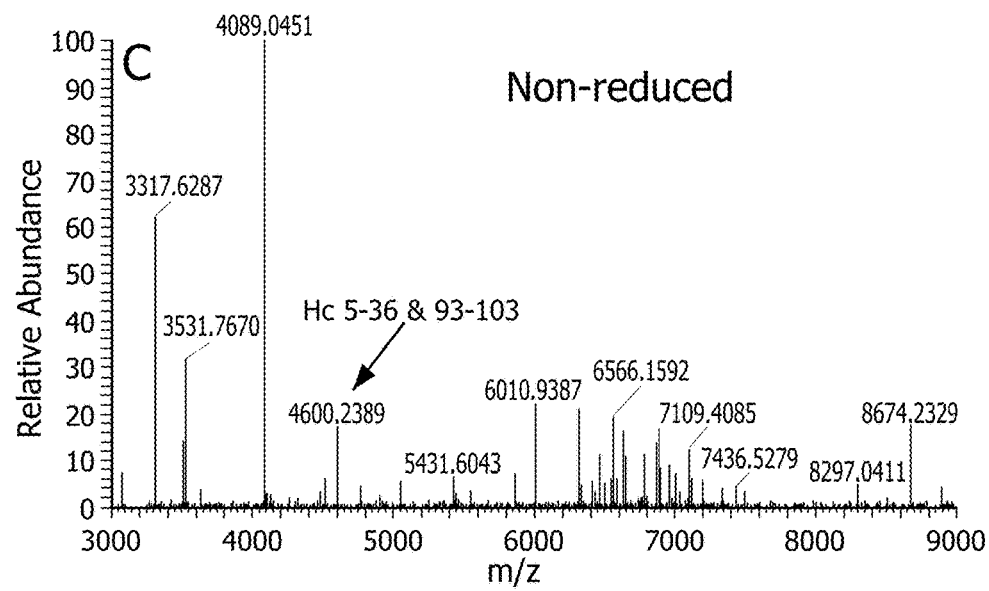
Figure 22D:
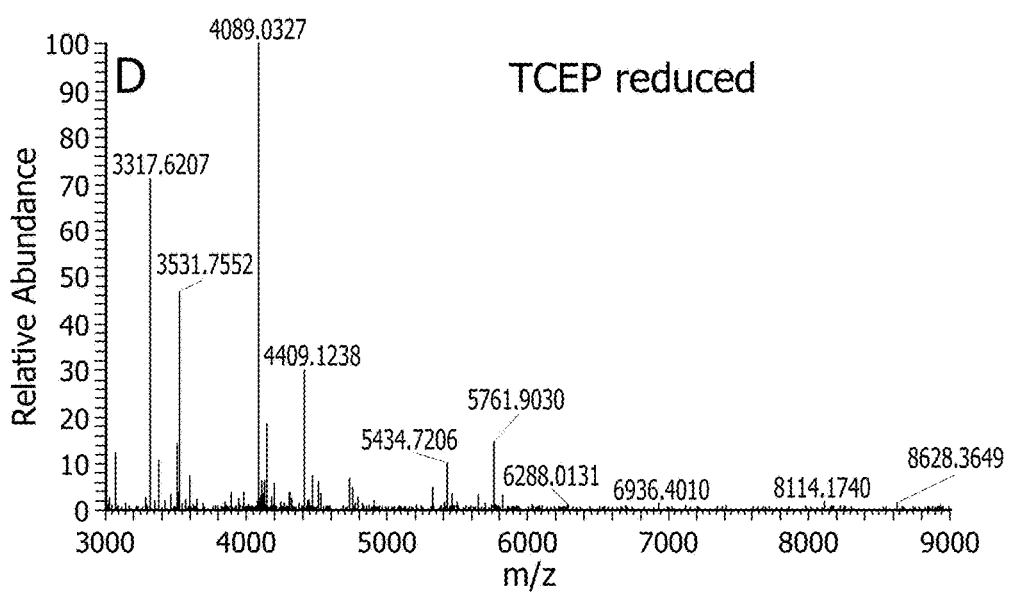
Figure 23A:
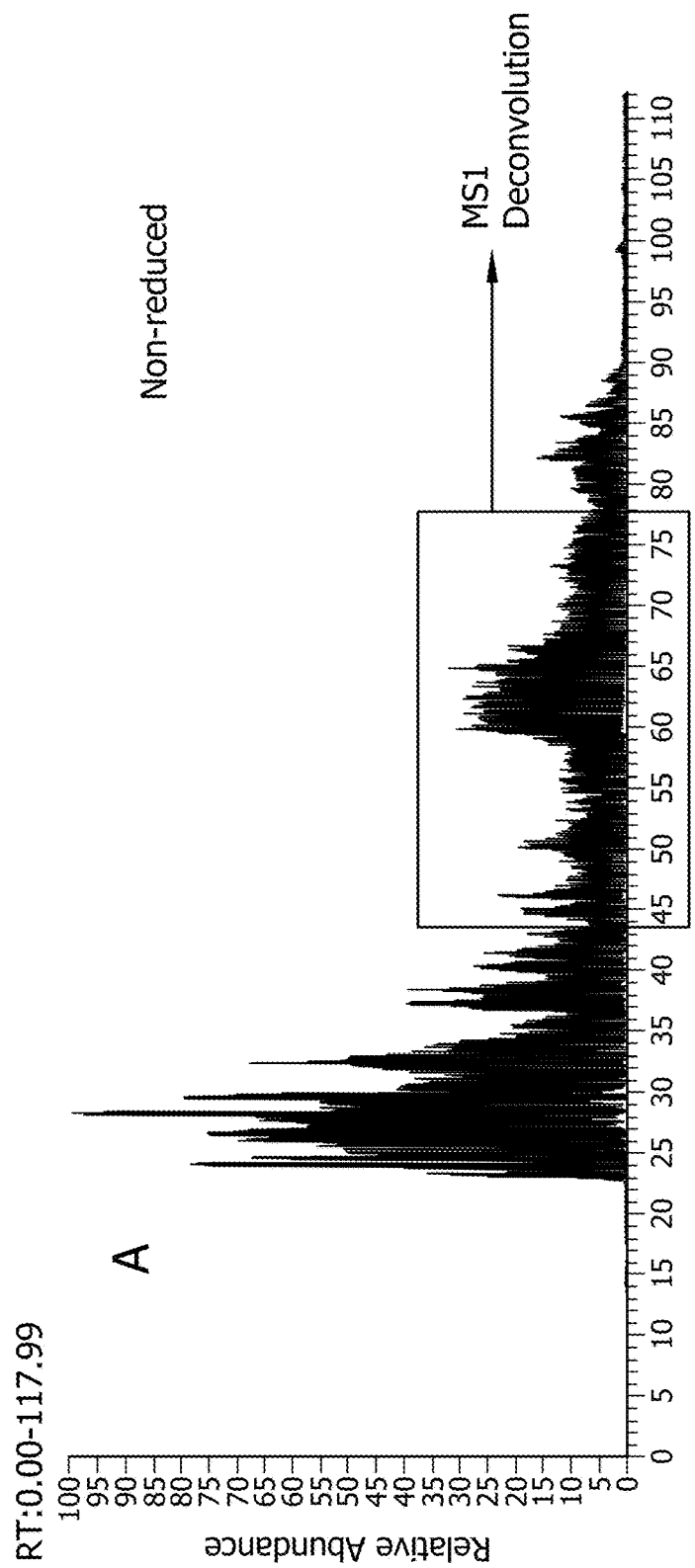
FIG. 23, comprising FIGS. 23A to 23E. Generation of disulfide peptides in $C_H1$ and $C_L$ by 260 s on-column digestion of intact mAb dissolved in 8M urea. A and B present the total ion current of LC-MS of the resulting digest with (B) and without (A) disulfide reduction. C and D present the MW (m/z where z=1) of the major large peptides eluted in A and B, respectively. ETD was performed on the major disulfide peptides to identify their sequences as labeled in C. These disulfide peptides do not appear in D due to disulfide reduction. E presents the extracted ion current of the disulfide peptides in $C_H1$ and $C_L$. F presents ETD/IIPT MS2 of disulfide peptide Lc119-148 & 191-212.
Figure 23B:
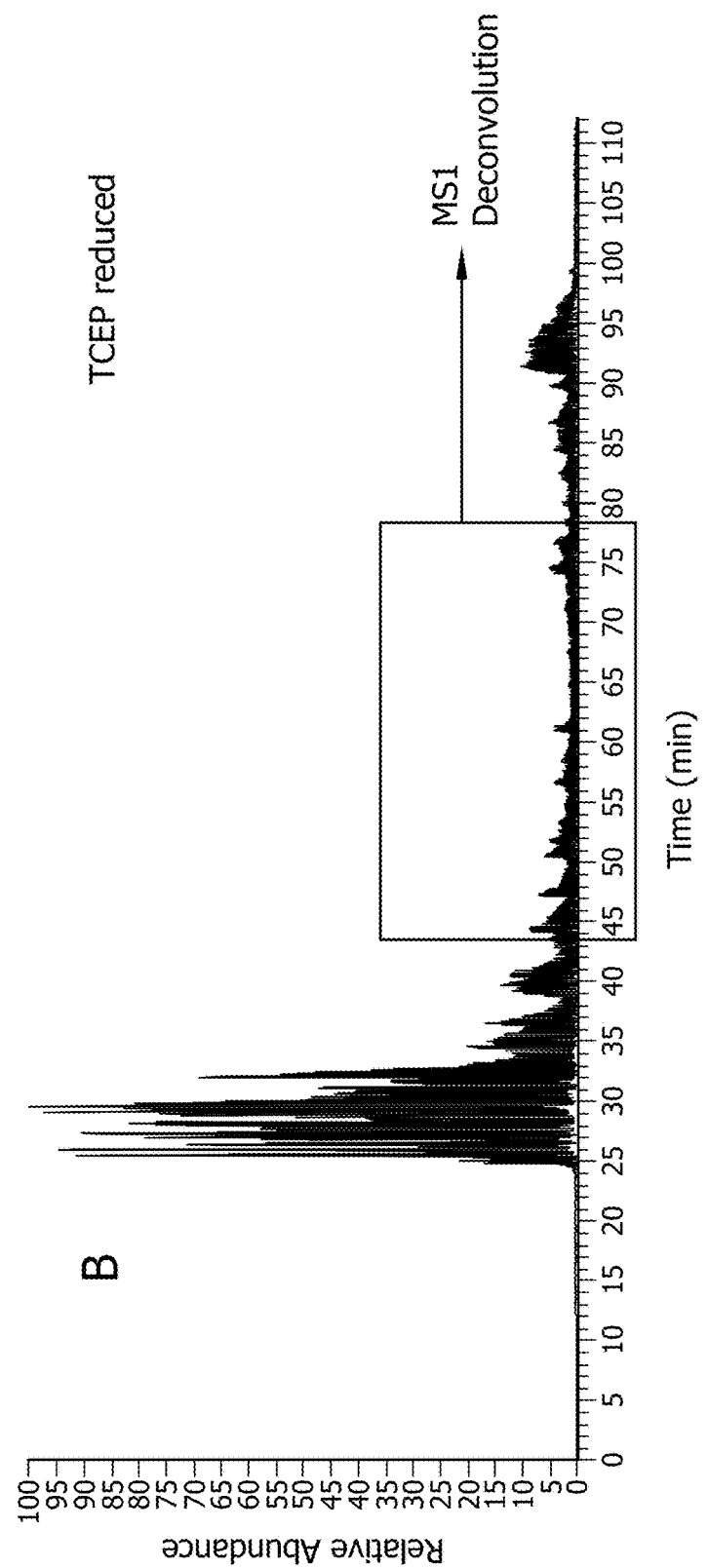
Figure 23C:
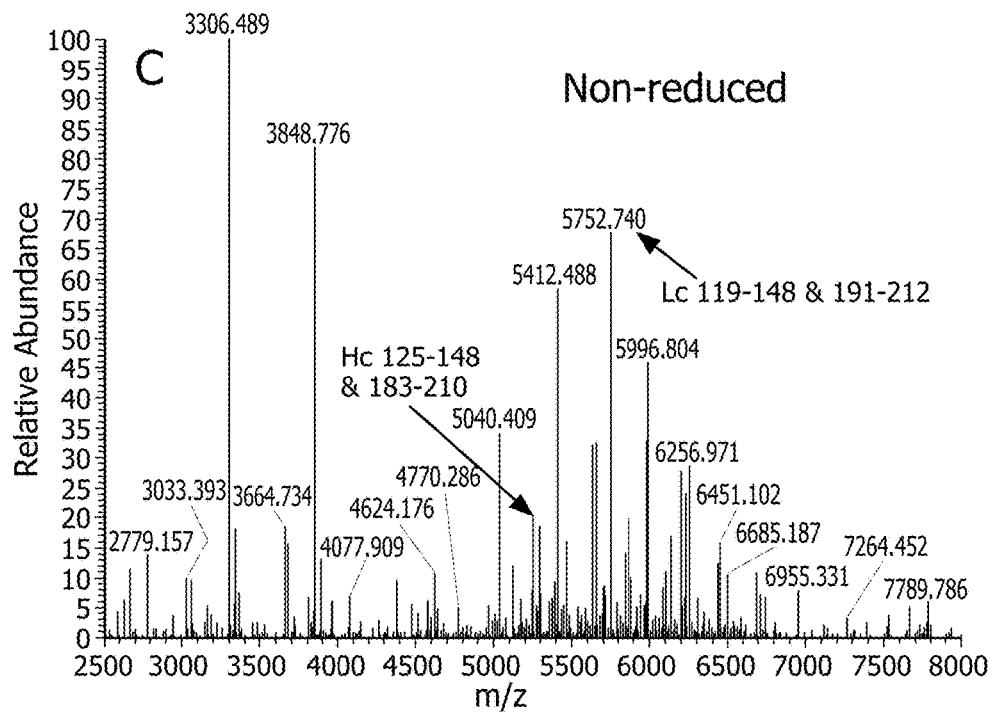
Figure 23D:
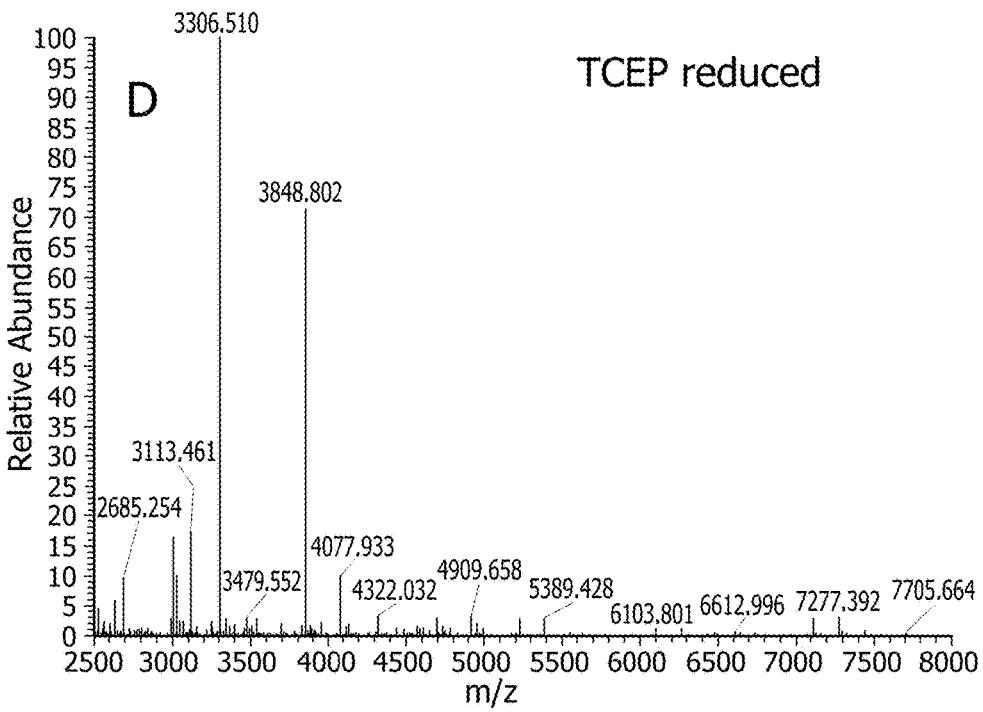
Figure 23E:
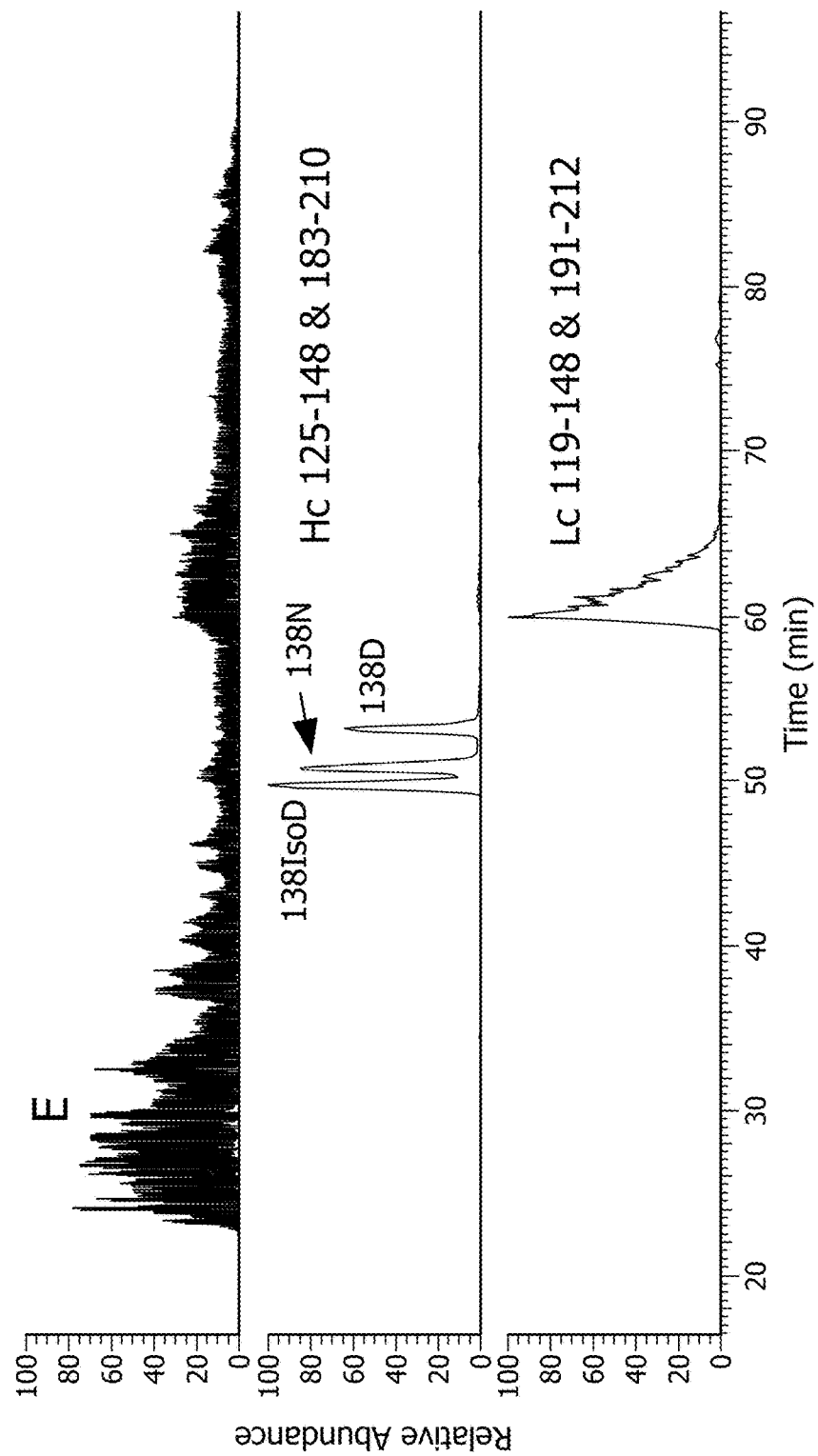
Figure 24B:
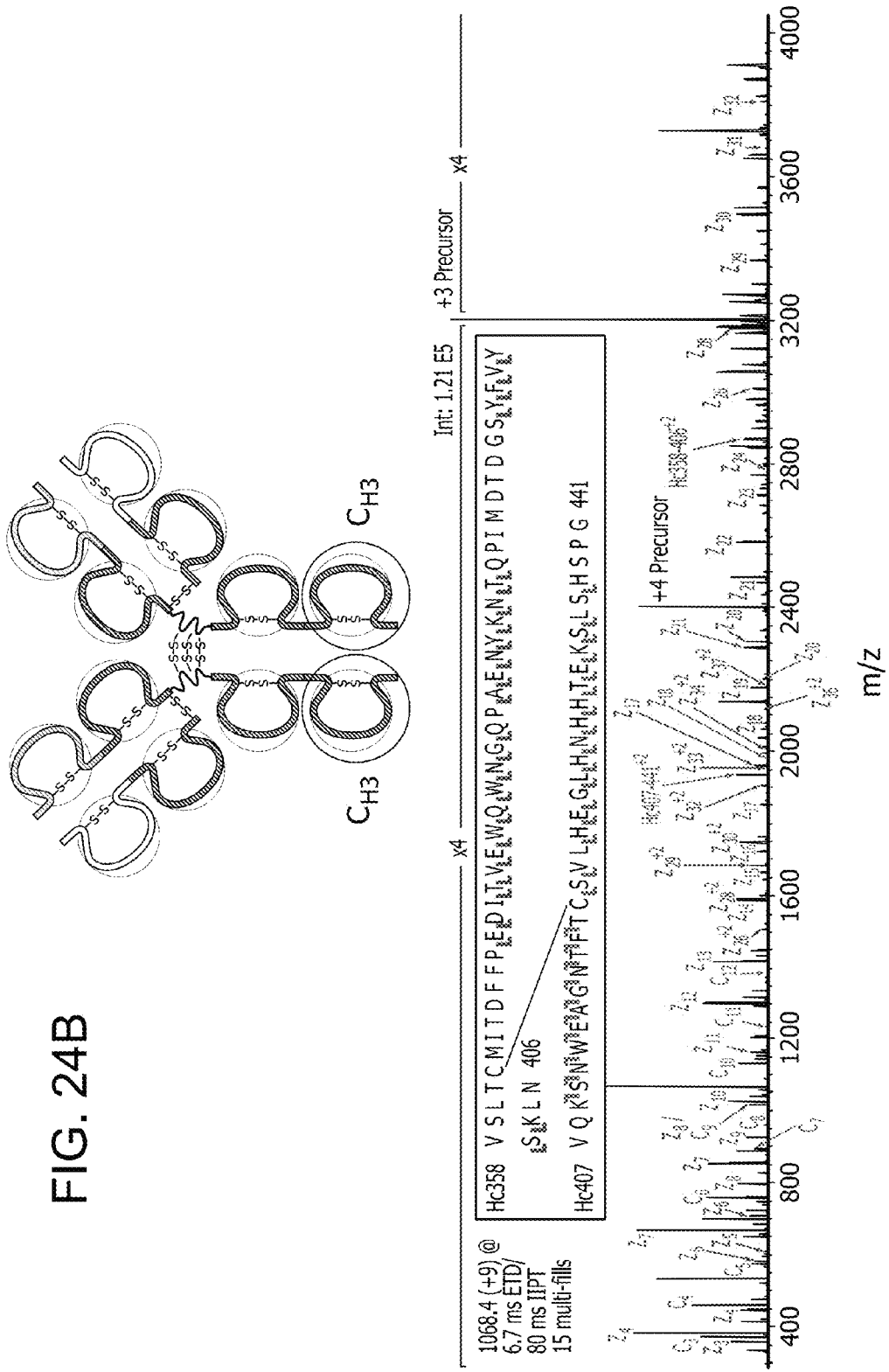
FIG. 24, comprising FIGS. 24A to 24G. ETD/IIPT of the disulfide-containing peptide in (A) $V_L$ produced by 12s on-column digestion of intact mAb (upper sequence-SEQ ID NO:2; lower sequence-SEQ ID NO:4), in (B) $C_{H3}$ produced by 12 s on-column digestion of intact mAb (upper sequence-SEQ ID NO:21; lower sequence-SEQ ID NO:22), in (C) $V_H$ produced by 93 s on-column digestion of intact mAb (upper sequence-SEQ ID NO:23; lower sequence-SEQ ID NO:24), in (D) $C_L$ produced by 260 s on-column digestion of intact mAb (upper sequence-SEQ ID NO:25; lower SEQ ID NO:26), in (E) $C_{H1}$ produced by 260 s on-column digestion of intact mAb (upper sequence-SEQ ID NO:27; lower sequence-SEQ ID NO:28), in (F) $C_{H2}$ produced by 740 s on-column digestion of intact mAb (upper sequence-SEQ ID NO:29; lower sequence-SEQ ID NO:30), and in (G) the hinge region produced by 740 s on-column digestion of intact mAb (SEQ ID NO:31). The identified c and z ions upon ETD/IIPT are labeled in each MS2 spectrum. The proposed structures of mAb in different digestion stages are drawn beside each spectrum, and the region of each identified peptide is highlighted in the corresponding portion of the mAb.
Figure 24C:
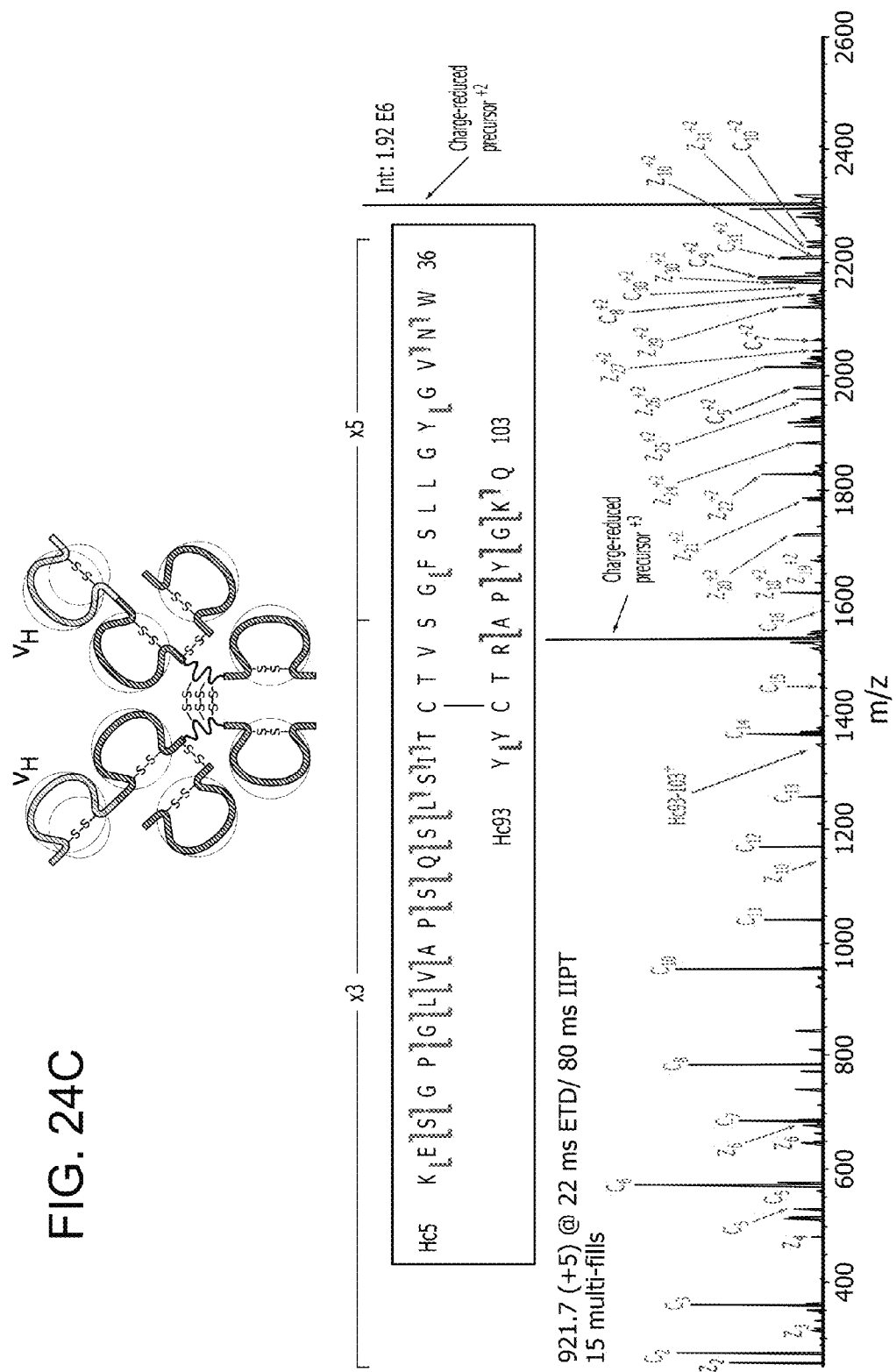
Figure 24D:
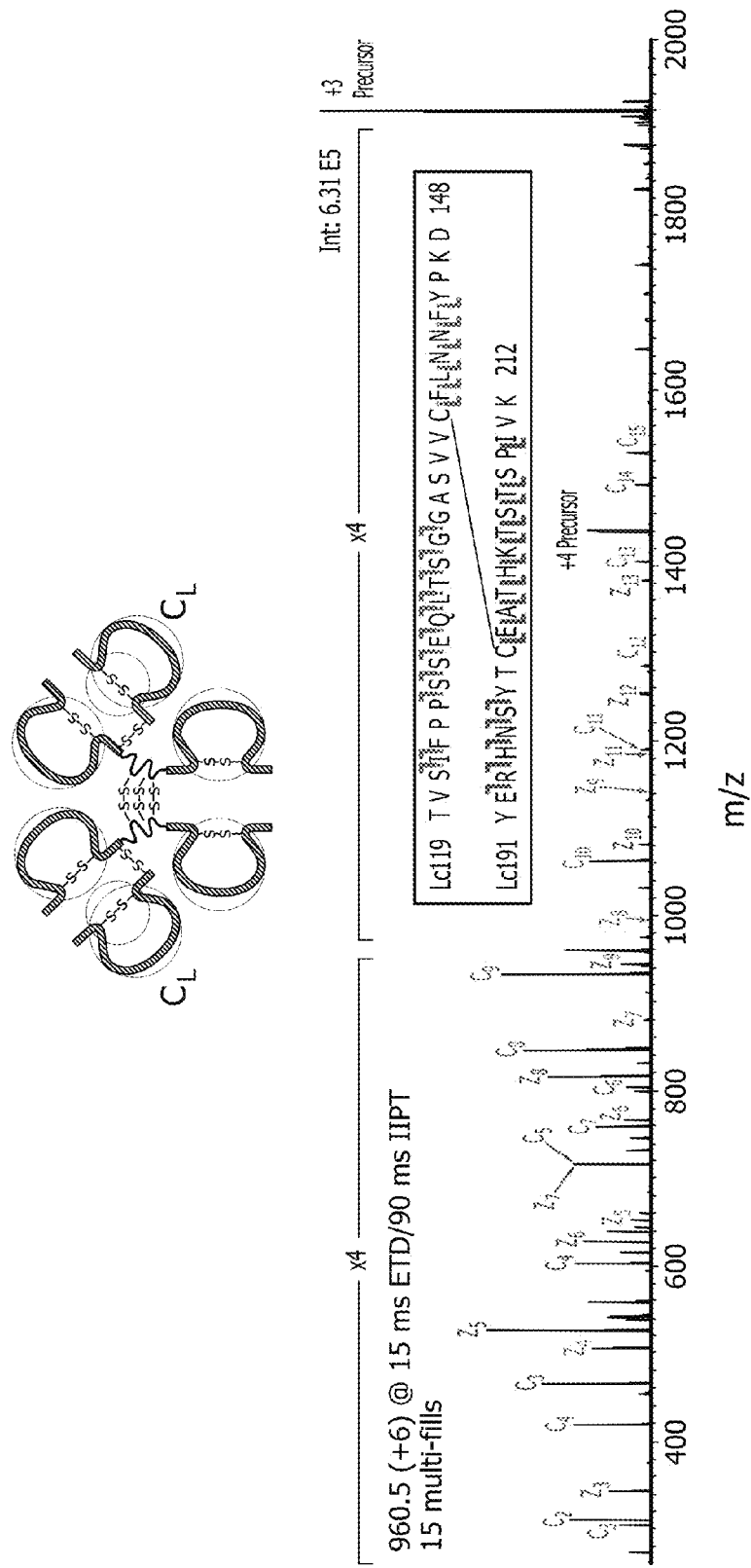
Figure 24F:
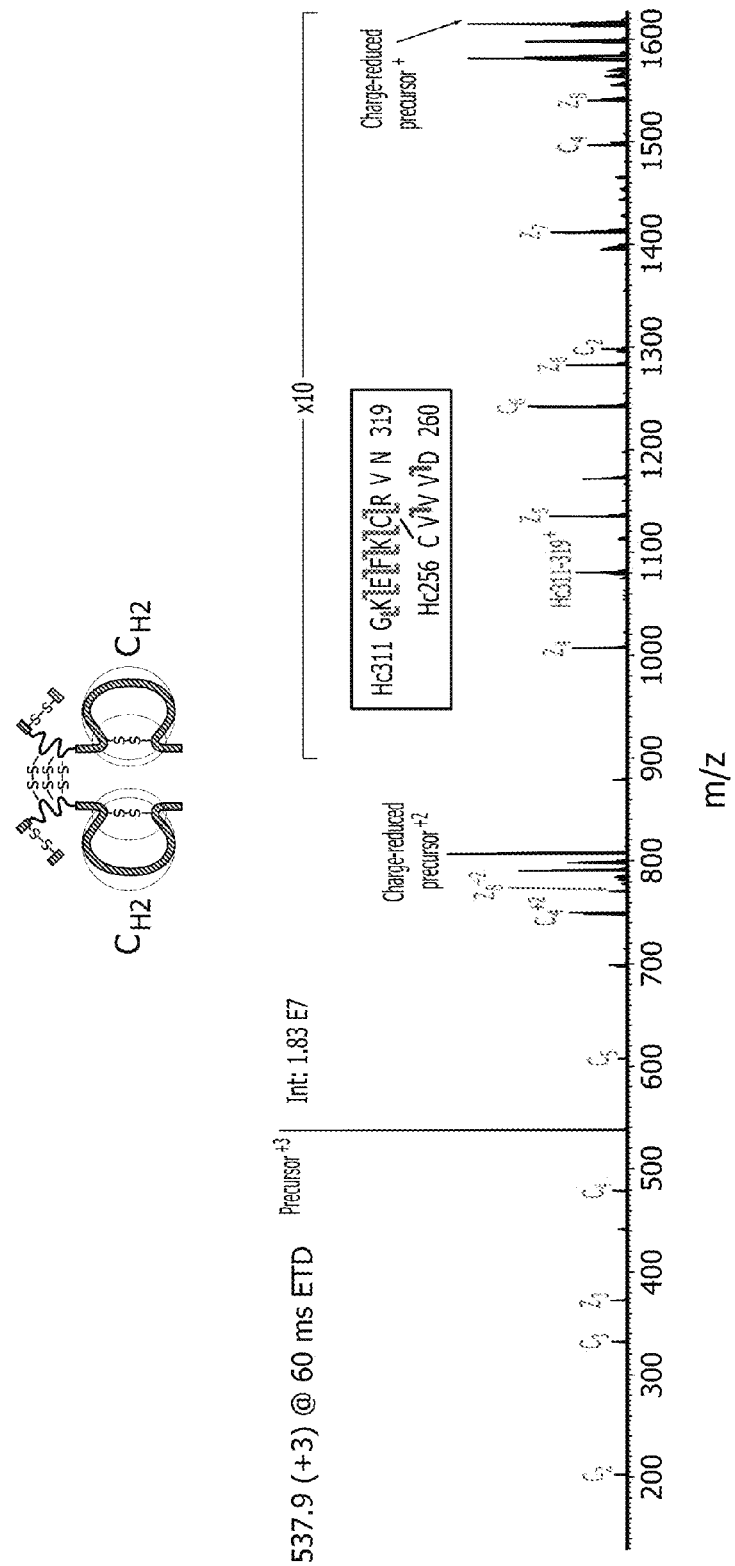
Figure 24G:
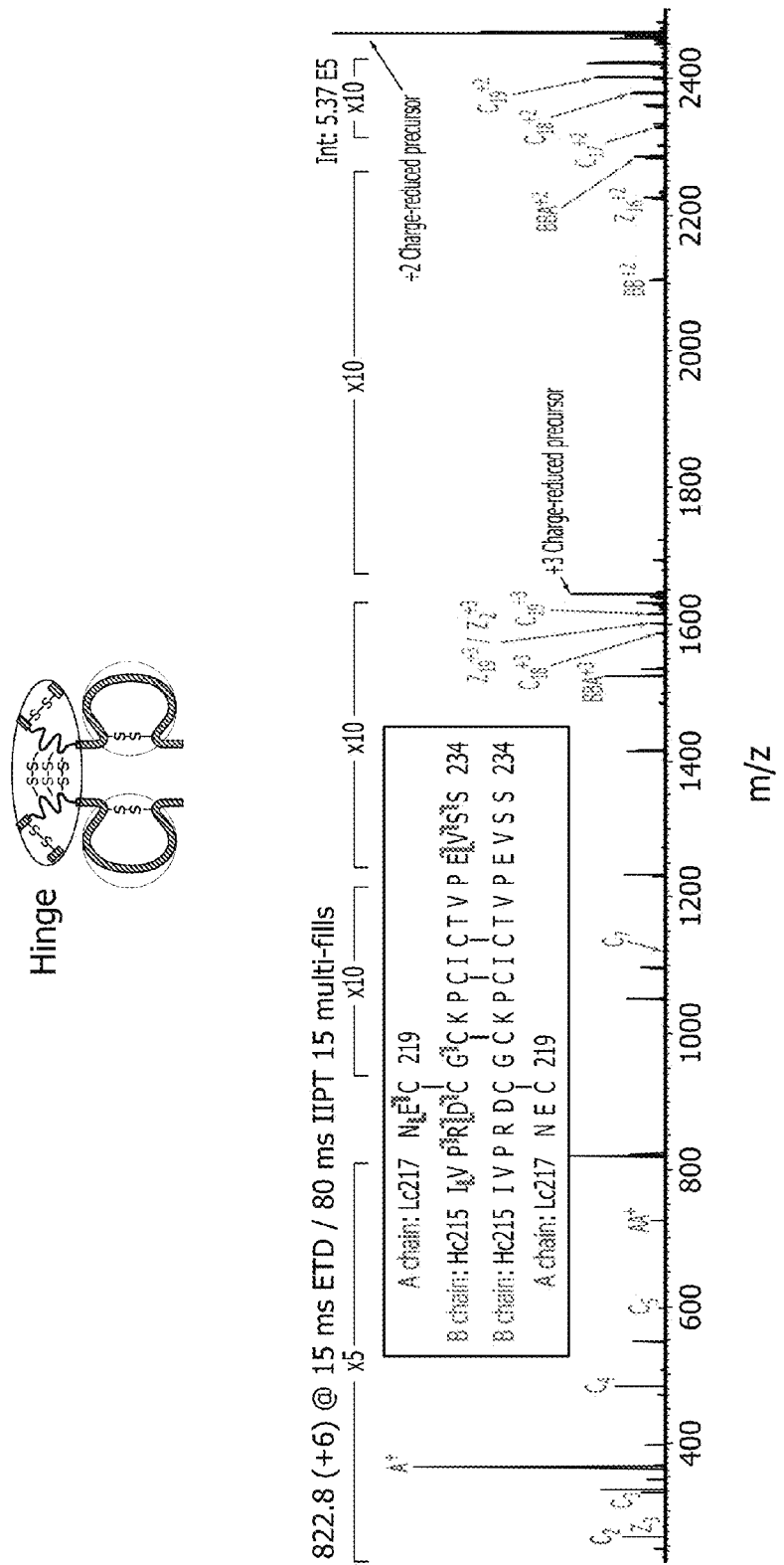

For example, 12 s on-column digestion of intact mAb produced a series of 6-12 kDa large peptides (FIG. 21A). The majority of these peptides disappeared upon reduction with TCEP (compare FIGS. 21A and B, and C and D), suggesting the existence of disulfide(s) within these large peptides. As some of these peptides are over 10 kDa with over +10 charge state, direct ETD of these peptides produced a collection of low level +1-+10 charge-state fragment ions (e.g., FIG. 4A-C). These ions however cannot quickly deduce the sequence of each peptide chain owing to their low intensity, limited c/z ions, and overlapping m/z values. Moreover, many of the highly charged fragment ions could contain sequences from two peptide chains connected by disulfide bond, further complicating the localization of disulfide. For example, the red ions in FIG. 4C correspond to the c or z ions produced from Lc53-108 peptide but with Lc 93C linked with the entire Lc1-52 chain; while the blue ions correspond to the c or z ions produced from Lc1-52 peptide but with Lc 23C linked with the entire Lc53-108 chain). As we have already sequenced this mAb, to quickly localize the disulfide bond(s), we performed ETD/IIPT on the disulfide-containing large peptides to generate mainly the N- and C-terminal fragments of the two disulfide-linked peptides. IIPT reduced the charge state of most fragments to mainly +1 and +2 such that they spread out the entire m/z range (up to 4000 for FT detection) and are readily identified instead of overlapping with each other. Upon IIPT, some ultra-high MW fragment ions (e.g. those carry the whole Lc1-52 or Lc53-108 chain as in FIG. 4C) are now beyond m/z 4000 and do not interfere with the detection of other low-charge state ions in the m/z 1000-4000 range. In addition, 15-cycle production of these low charge-state ions (ions produced in ion trap and stored in C-trap) prior to Orbitrap analysis greatly increased the fragment ion intensity (compare FIGS. 4D and B). In this way, we quickly identified the two peptide chains (i.e. Lc1-52 and Lc53-108) based on their partial or near complete N- and C-terminal sequences. As the two peptides both have only one Cys residue within the chain, the disulfide bond in $V_L$ can be assigned as Lc 93C-23C. Similarly, we identified the disulfide in $C_{H3}$ to be Hc362C-420C using a 9606 Da peptide (FIGS. 21C and E, and FIG. 24A). Further increasing the on-column digestion time to 93 s, 260 s, and 740 s generated disulfide-containing peptides in $V_H$ (FIG. 24B), $C_L$ and $C_{H1}$ (FIGS. 24C and D), and $C_{H2}$ and the hinge region (FIGS. 24E and F), respectively. See also FIG. 18. Table 1 lists all the identified disulfides in mAb.

DISCUSSION

Time-Controlled Digestion.

Time-controlled digestion using immobilized aspergillopepsin I narrows the size range of most major peptides to 3-8 kDa. Peptides in this mass range have higher sequence coverage and C18 retention than tryptic peptides, and are compatible with online high resolution ETD MS/MS analysis. Although aspergillopepsin I favors protein hydrolysis at hydrophobic and Lys residues, the actual hydrolysis chances on these sites are not completely equal. Otherwise the time-controlled digestion would generate a much higher number of 3-8 kDa peptides with highly overlapped sequences and equivalent abundances. Based on the major large peptides produced from apomyoglobin and mAb in this work, the most frequent hydrolysis occurs at N-terminus of V, L, and I, and C-terminus of K. The "partially controlled" protease specificity is also reflected by the following calculations. The average MW of the 39 targeted major large peptides is 5485 Da. Using this average size as a scale, covering the whole sequence of He and Lc (combined MW 76.5 kDa considering modifications) would need at least 14 peptides of this size. The actual number of major peptides we targeted for MS/MS however is no more than 3 times of this number, suggesting a controllable sample complexity for mAb sequencing. Moreover, these peptides provide overlapping sequences which are beneficial to characterizing mAbs with unknown sequences.

Considering the broad specificity nature of the protease and the random encounters between proteins and proteases, one direct concern would be the repeatability of protein digestion using this approach. Fortunately, precise control of digestion time t (realized by accurate control of sample flow rate F) should yield a repeatable statistical distribution of digestion pathways for a given protein sample, leading to batches of digest samples with similar distributions of large peptides.

Here, we controlled peptide sizes to mainly 3-9 kDa without exploring peptides over this size range. This is partly because further increasing peptides size (by shortening protein residence time in the protease column) results in a large quantity of undigested protein. Peptides over 10 kDa typically elute close to undigested protein as tailing peaks on the POROSHELL C18 column operated at room temperature, leading to complex full MS in the late gradient region. In addition, under a given AGC (1E6 in this work), the S/N of fragment ions in MS2 spectrum drops significantly as the peptide size increases over 10 kDa. Ongoing research using a combination of new chromatographic materials, separations conducted at temperatures above room temperature, and FETD (front end electron dissociation) xx that facilitates rapid accumulation ions in the C-trap prior to mass analysis in the Orbitrap and provides a S/N enhancement in excess of 50, should make it possible to use the present invention to characterize protein fragments in excess of 10 kDa on a routine basis (Front-End Electron Transfer Dissociation: A New Ionization Source, Earley L, Anderson L C, Bai D L, Mullen C, Syka J E P, English A M, Dunyach J-J, Stafford G C, Shabanowitz J, Hunt D F, Compton P D, Anal Chem, 2013; 85 (17):8385-8390. PMCID: PMC 3822909).

Another application of the technology involves the study of protein dynamics by hydrogen/deuterium exchange. Solvent exposed hydrogens on heteroatoms in the protein sequence undergo rapid exchange for deuterium at physiological pH in the presence of deuterium oxide. Those involved in intramolecular hydrogen bonds that define the secondary structure of the protein or those that are involved with protein binding partners either exchange at much slower rates or fail to exchange at all. Deuterium exchange is quenched in acidic solution so pepsin is routinely used to digest the deuterium labeled proteins to produce small peptides that can then me analyzed by mass spectrometry to define which amino acid residues in the protein are solvent exposed or occluded by protein folding or binding to protein partners. Scrambling of the deuterium label does not occur under ETD conditions. The present invention makes it possible to perform the protein digestion under acidic conditions, in a controlled manner, to generate large protein fragments and yet pinpoint specific residues that are, or are not, solvent exposed in the folded protein structure (Li, J., Rodnin, M. V., Ladokhin, A. S., and Gross, M. L. (2014) Hydrogen-Deuterium Exchange and Mass Spectrometry Reveal the pH-Dependent Conformational Changes of Diphtheria Toxin T Domain. Biochemistry 53, 6849-6856).

Multi-Segment MS/MS.

This work used a "customized" MS/MS method to sequence near 40 large mAb peptides. The MS/MS settings take into account the charge state of each target peptide for optimized ETD, and takes advantage of the highly reproducible peptide retention time on the POROSHELL C18 column (within 0.3 min for each peptide from a given digest on the same column). This is in great contrast to conventional data-dependent MS/MS, in which a fixed ETD time was applied to high abundant peptides without considering its charge state. To improve LC-ETD FT MS/MS efficiency, future analyses of similar or more complex samples could consider advanced instrument control code which has the following features: (1) Automatic selection of the precursor ion with the highest charge state (if above an intensity threshold) from a peptide with a desired size range (size calculated based on m/z and ion charge state) (2) The choice of using ETD or CAD or both is programmed according to the charge state and the m/z of the precursor ion. Based on our experience in this work, to obtain near complete sequence of a protein, we propose to perform only ETD for peptides with z≥6 and m/z<800, and perform only CAD for peptides with z≤2. For peptides with 3≤z≤5 and m/z≥800, or peptides with z≥6 and m/z>900, we recommend performing both ETD and CAD. (3) Automatically setting ETD reaction time according to the reciprocal relationship of t and peptide charge state to optimize ETD kinetics.

Summary

We developed a strategy which utilizes immobilized aspergillopepsin I, a protease with broad specificity and consistent activity in 8M urea, to digest denatured proteins into large peptides via a size-control mode. Selecting a proper flow rate as the protein sample passes through the protease column precisely controls digestion time. This method generates mainly 3-9 kDa peptides from apomyoglobin and mAb. Peptides in this size range are favorable for protein sequencing when coupled with online LC-ETD MS/MS. In addition, the employment of NAEM as a new Cys alkylating reagent improves ETD of peptides containing CDRs by enhancing the peptide charge state. Using a multi-segment online LC-MS/MS strategy, we successfully sequenced a 150 kDa mAb with 98% sequence coverage on Lc and 94% sequence coverage on Hc. We also identified multiple PTMs on this mAb, including pyroglutamic acid formation, oxidation, amidation, and glycosylation. The presently disclosed strategy breaks the limit of traditional protein digestion, which generates peptides in a pre-defined size range or has decreased enzyme activity in buffers containing high concentrations of chaotropic agent.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Bensimon, A., Heck, A. J. R., and Aebersold, R. (2012) Mass spectrometry-based proteomics and network biology. Annu. Rev. Biochem. 81, 379-405
2. Lanucara, F. and Eyers, C. E. (2013) Top-down mass spectrometry for the analysis of combinatorial post-translational modifications. Mass Spectrom. Rev. 32, 27-42
3. Garcia, B. A. (2010) What does the future hold for top down mass spectrometry? J. Am. Soc. Mass Spectrom. 21, 193-202
4. Kalli, A., Sweredoski, M. J., and Hess, S. (2013) Data-dependent middle-down nano-liquid chromatography-electron capture dissociation-tandem mass spectrometry: An application for the analysis of unfractionated histones. Anal. Chem. 85, 3501-3507
5. Wu, S., Kim, J., Hancock, W. S., and Karger, B. (2005) Extended range proteomic analysis (ERPA): A new and sensitive LC-MS platform for high sequence coverage of complex proteins with extensive post-translational Modifications Comprehensive analysis of beta-casein and epidermal growth factor receptor (EGFR). J. Proteome Res. 4, 1155-1170
6. Wu, C., Tran, J. C., Zamdborg, L., Durbin, K. R., Li, M., Ahlf, D. R., Early, B. P., Thomas, P. M., Sweedler, J. V., and Kelleher, N. L. (2012) A protease for 'middle-down' proteomics. Nat. Methods 9, 822-824
7. Cannon, J., Lohnes, K., Wynne, C., Wang, Y., Edwards, N., and Fenselau, C. (2010) High-throughput middle-down analysis using an orbitrap. J. Proteome Res. 9, 3886-3890
8. Garcia, B. A., Siuti, N., Thomas, C. E., Mizzen, C. A., and Kelleher, N. L. (2007) Characterization of neurohistone variants and post-translational modifications by electron capture dissociation mass spectrometry. Int. J. Mass Spectrom. 259, 184-196
9. Ge, Y., Rybakova, I. N., Xu, Q., and Moss, R. L. (2009) Top-down high-resolution mass spectrometry of cardiac myosin binding protein C revealed that truncation alters protein phosphorylation state. Proc. Natl. Acad. Sci. U.S.A 106, 12658-12663
10. Laskay, U. A., Lobas, A. A., Srzentic, K., Gorshkov, M. V., and Tsybin, Y. O. (2013) Proteome digestion specificity analysis for rational design of extended bottom-up and middle-down proteomics experiments. Journal of Proteome Research 12, 5558-5569
11. Wright, A. and Morrison, S. L. (1997) Effect of glycosylation on antibody function: Implications for genetic engineering. Trends Biotechnol. 15, 26-32
12. Fernandez, L., Kalume, D., Calvo, L., Mallo, M., Vallin, A., and Roepstorff, P. (2001) Characterization of a recombinant monoclonal antibody by mass spectrometry combined with liquid chromatography. J. Chromatogr. B 752, 247-261
13. Roberts, G. D., Johnson, W. P., Burman, S., Anumula, K. R., and Carr, S. A. (1995) An integrated strategy for structural characterization of the protein and carbohydrate components of monoclonal-antibodies—application to anti-respiratory syncytial virus mab. Anal. Chem. 67, 3613-3625
14. Zhang, Z., Pan, H., and Chen, X. (2009) Mass spectrometry for structural characterization of therapeutic antibodies. Mass Spectrom. Rev. 28, 147-176

15. Tan, Y., Wang, W., Zheng, Y., Dong, J., Stefano, G., Brandizzi, F., Garavito, R. M., Reid, G. E., and Bruening, M. L. (2012) Limited proteolysis via millisecond digestions in protease-modified membranes. Anal. Chem. 84, 8357-8363
16. Syka, J. E. P., Coon, J. J., Schroeder, M. J., Shabanowitz, J., and Hunt, D. F. (2004) Peptide and protein sequence analysis by electron transfer dissociation mass spectrometry. Proc. Natl. Acad. Sci. U.S.A 101, 9528-9533
17. McLuckey, S. and Stephenson, J. (1998) Ion ion chemistry of high-mass multiply charged ions. Mass Spectrom. Rev. 17, 369-407
18. Stanfield, R. L. and Wilson, I. A. (2009) Therapeutic Monoclonal Antibodies: From Bench to Clinic, John Wiley & Sons, Inc., Hoboken, N.J.
19. Martin, A. C. R. (2010) Chapter 3 Protein Sequence and Structure Analysis of Antibody Variable Domains from Antibody Engineering Volumn 2, 2nd Ed., Springer, New York, N.Y.
20. Varki, A., Cummings, R., Esko, J., Freeze, H., Hart, G., and Marth, J. (1999) Essentials of Glycobiology, 2nd Ed., Cold Spring Harbor Laboratory Press, New York, N.Y.
21. Choksawangkarn W, Kim S-K, Cannon J R, Edwards N J, Lee S B, Fenselau C, Enrichment of Plasma Membrane Proteins Using Nanoparticle Pellicles: Comparison Between Silica and Higher Density Nanoparticles, J Proteome Res 2013; 12:1134-1141.
22. Switzar L, Giera M, Niessen W M A, Protein Digestion: An Overview of the Available Techniques and Recent Developments, J Proteome Res 2013; 12:1067-1077.
23. Taoutas N, Heck A J, Mohammed S, Evaluation of Metalloenopeptidase Lys-N Protease Performance Under Different Sample Handling Conditions, J Proteome Res 2010; 9(8):4282-4288.
24. Wu C, Tran J C, Zamdborg L, Durbin K R, Li M, Ahlf D R, Early B P, Thomas P M, Sweedler J V, Kelleher N L, A Protease for 'Middle-down' Proteomics, Nat Methods 2012; 9(8):822-824.
25. Tan et al. "Limited Proteolysis via Millisecond Digestions in Protease-Modified Membranes" Anal. Chem. 2012, 84, 8357-8363.
26. Coon J J, Ueberheide B, Syka J E P, Dryhurst D D, Ausio J, Shabanowitz J, Hunt D F, "Protein Identification Using Sequential Ion/Ion Reactions and Tandem Mass Spectrometry". Proc Natl Acad Sci USA, 2005 Jul. 5; 102(27): 9463-8. PMCID: PMC1172258.
27. Chi A, Bai D L, Geer L Y, Shabanowitz J, Hunt D F, "Analysis of Intact Proteins on a Chromatographic Time Scale by Electron Transfer Dissociation Tandem Mass Spectrometry", Int. J. Mass Spectrom., 2007, 259, 197-203. PMCID: PMC 1826913.
28. Anderson L C, English A M, Wang W-H, Bai D L, Shabanowitz J, and Hunt D F, "Protein Derivatization and Sequential Ion-Ion Reactions to Enhance Sequence Coverage Produced by Electron Transfer Dissociation Mass Spectrometry", Int J Mass Spectrom 2014, DOI: 10.1016/j.ijms.2014.06.02.
29. Earley L, et al. "Front-End Electron Transfer Dissociation: A New Ionization Source", Anal Chem. 2013; 85(17):8385-8390. PMCID: PMC 3822909.
30. Li, J., et al., (2014), "Hydrogen-Deuterium Exchange and Mass Spectrometry Reveal the pH-Dependent Conformational Changes of Diphtheria Toxin T Domain", Biochemistry 53, 6849-6856.

TABLE 1

| Identified mAb PTMs and disulfides | |
|---|---|
| PTM | Site |
| Oxidation | Lc Met4, Hc Met304, Met49*, Met140*, Met353*, Met363*, Met393* |
| Pyruglutamate | Hc N-term Gln |
| Deamidation | Hc Asn138 |
| N-linked glycosylation (G0F, G1F, G2F) | Hc Asn292 |
| Disulfides | Lc 93C-23C, Hc362C-420C, Hc22C-95C, Lc139C-199C, Hc145C-200C, Hc256C-316C, Lc219C-Hc220C, Hc(222C, 225C, 227C)-Hc(222C, 225C, 227C) |

Low level Met oxidation sites identified by extra targeted MS/MS

TABLE S1

| | Comparison of ETD- and CAD-fragment ions of major large peptides containing Cys. | | | | | |
|---|---|---|---|---|---|---|
| Sequence | | Ave | Charge state[2] | | m/z[3] | |
| No. | Peptide sequence | MW[1] | IAM | NAEM | IAM | NAEM |
| L1-52 | DVLMTQTPLSLPVSLGDQASISCRSSQY IVHSNGNTYLEWYLQKPGQSPKLL | 5767 | 5 | 6 | 1166 | 985 |
| L53-110 | IYKVSNRFSGVPDRFSGSGSGTDFTLKIS RVEAEDLGVYYCFQGSHVPLTFGAGTK LE | 6294 | 8 | 8 | 795 | 805 |
| L111-148 | IKRADAAPTVSIFPPSSEQLTSGGASVV CFLNNFYPKD | 4030 | 4 | 5 | 1022 | 835 |
| L149-219 | INVKWKIDGSERQNGVLNSWTDQDSK DSTYSMSSTLTLTKDEYERHNSYTCEAT HKTSTSPIVKSFNRNEC | 8166 | 9 | 11 | 921 | 769 |
| H1-36 | α(pyro-Glu) VQLKESGPGLVAPSQSLSITCTVSG FSLLGYGVNW | 3708 | 3 | 3 | 1256 | 1283 |
| H84-148 | SLQTDDTAKYYCTRAPYGKQYFAYWG QGTLVTVSAAKTTPPSVYPLAPGSAAQ TD(amidation)SMVTLGCLVK | 6941 | 6 | 8 | 1177 | 904 |
| H149-210 | GYFPEPVTVTWNSGSLSSGVHTFPAVL QSDLYTLSSSVTVPSSTWPSETVTCNV AHPASSTK | 6502 | 5 | 5 | 1313 | 1329 |
| H211-260 | VDKKIVPRDCGCKPCICTVPEVSSVFIF PPKPKDVLTITLTPKVTCVVVD | 5431 | 6 | 9 | 953 | 682 |

TABLE S1-continued

Comparison of ETD- and CAD-fragment ions of major large peptides containing Cys.

| | | | | | | |
|---|---|---|---|---|---|---|
| H277-319 | VEVHTAHTQPREEQFN(G0F)STFRSVS ELPIMHQDWLNGKEFKCRVN | 5128 | 7 | 8 | 948 (742) | 840 (659) |
| H320-371 | SAAFPAPIEKTISKTKGRPKAPQVYTIPP PKEQMAKDKVSLTCMITDFFPED | 5752 | 7 | 8 | 831 | 737 |
| H372-441 | ITVEWQWNGQPAENYKNTQPIMDTD GSYFVYSKLNVQKSNWEAGNTFTCSVL HEGLHNHHTEKSLSHSPG | 7992 | 10 | 10 | 806 | 814 |

| Sequence No. | ETD sites | | CAD sites | | Total observed cleavage sites[4] | | Theor total cleavages[5] | Pro |
|---|---|---|---|---|---|---|---|---|
| | IAM | NAEM | IAM | NAEM | IAM | NAEM | | |
| L1-52 | 10 | 33 | 32 | 22 | 42 | 43 | 51 | 4 |
| L53-110 | 52 | 54 | 45 | 35 | 57 | 57 | 57 | 2 |
| L111-148 | 3 | 33 | 26 | 25 | 27 | 37 | 37 | 4 |
| L149-219 | 47 | 50 | 60 | 37 | 66 | 65 | 70 | 1 |
| H1-36 | 2 | 2 | 31 | 34 | 32 | 35 | 35 | 2 |
| H84-148 | 38 | 37 | 45 | 27 | 54 | 46 | 64 | 5 |
| H149-210 | 11 | 8 | 39 | 40 | 45 | 45 | 61 | 6 |
| H211-260 | 26 | 36 | 14 | 32 | 32 | 43 | 49 | 7 |
| H277-319 | 37 | 37 | na | na | 37 | 37 | 42 | 2 |
| H320-371 | 36 | 38 | 31 | 17 | 47 | 45 | 51 | 7 |
| H372-441 | 52 | 53 | 44 | 36 | 63 | 66 | 69 | 3 |

[1]MW of peptides corresponding to SEQ ID 2 and 9-18, respectively (considering PTMs), before alkylation of reduced Cys
[2]Charge state of the peptide to be compared
[3]The actual average m/z of isolated precursor ion considering PTM and Cys alkylation, except for the one in ( ) stands for the m/z if not considering G0F modification
[4]Observed cleavage sites due to at least one of the fragment ions: c, z, b and y
[5]Theoretical total number of cleavage sites, i.e. the number of amino acids minus one

What is claimed is:

1. A method for characterizing a protein, said method comprising:
optionally denaturing the protein;
dissolving said protein in a digestion buffer;
passing the digestion buffer comprising said protein through a reaction chamber comprising at least one hydrolyzing agent, wherein said protein contacts said hydrolyzing agent and is present in the chamber for a period of time (t) sufficient to produce protein fragments and digestion of said protein occurs in the chamber, wherein the passing of the digestion buffer comprising the protein through the chamber is done at a flow rate which determines the digestion of the protein in the reaction chamber; and
performing multi-segment liquid chromatography tandem mass spectrometry (LC MS/MS) to characterize the protein, wherein said characterization is selected from sequencing, identifying post-translational modifications (PTMs), and locating disulfide bonds,
wherein said digested protein is subjected to electron transfer dissociation (ETD)/ion-ion proton transfer (IIPT) to identify the disulfide-containing fragments and N- and C-terminal sequences and localize the disulfide(s) within/connecting different domains.

2. The method of claim 1, wherein the digestion times for a disulfide analysis are from about 10 seconds (s) to about 20 minutes (min).

3. The method of claim 2, wherein the digestion times for a disulfide analysis are selected from about 12 s to about 10 min.

4. The method of claim 1, wherein the digestion times for a disulfide analysis are selected from the group consisting of about 12 s, 93 s, 260 s, and 740 s.

5. The method of claim 1, wherein the protein is denatured before dissolving in the digestion buffer.

6. The method of claim 1, wherein the protein is exposed to the hydrolyzing agent under acidic and highly chaotropic conditions.

7. The method of claim 6, wherein said chaotropic conditions are urea at about 6 to about 9 Molar (M).

8. The method of claim 7, wherein said urea is at about 6, 7, or 8M.

9. The method of claim 8, wherein said urea is at 8M.

10. The method of claim 7, wherein said urea is used at a pH of about 3.0 to about 5.0.

11. The method of claim 7, wherein said urea is used at a pH of about 3.5 to about 4.5.

12. The method of claim 7, wherein said urea is used at a pH of about 3.9 or 4.0.

13. The method of claim 6, wherein the digested protein fragments range from about 3 kilodaltons (kDa) in mass to about 10 kDa in mass.

14. The method of claim 6, wherein the digested protein fragments range from about 10 kDa in mass to about 20 kDa in mass.

15. The method of claim 6, wherein the digested protein fragments range from about 20 kDa in mass to about 50 kDa in mass.

16. The method of claim 1, wherein the digestion times range from about 0.5 s to about 10 min.

17. The method of claim 5, wherein the digestion times are from about 0.5 s to about 10 minutes.

18. The method of claim 17, wherein the digestion times are about 0.7 s or about 5.7 s.

19. The method of claim 1, wherein said PTMs are selected from the group consisting of pyroglutamic acid formation, oxidation, amidation, deamidation, phosphorylation, methylation, acetylation, and glycosylation.

20. The method of claim 1, wherein the hydrolyzing agent is a protease or a biologically active fragment or homolog thereof, wherein said homolog is a substantially homologous amino acid sequence to said protease.

21. The method of claim 20, wherein the protease is selected from the group consisting of aspergillopepsin I, LysN protease (Lys-N), LysC endoproteinase (Lys-C), endoproteinase Asp-N (Asp-N), endoproteinase Glu-C (Glu-C) and outer membrane protein T (OmpT), or biologically active fragments or homologs thereof, wherein said homologs are a substantially homologous amino acid sequence to said protease.

22. The method of claim 20, wherein the protease is aspergillopepsin I (SEQ ID NO:32) or a biologically active fragment or homolog thereof, wherein said homolog is a substantially homologous amino acid sequence to SEQ ID NO:32.

23. The method of claim 1, wherein the flow rate is selected from a range of about 50 µl/min to about 4.0 µl/min.

24. The method of claim 1, wherein at least two proteins are characterized.

25. The method of claim 24, wherein said denatured protein is reduced and alkylated before dissolving in said digestion buffer.

26. The method of claim 1, wherein said protein is selected from the group consisting of an antibody, an antibody-like molecule, an antibody light chain, an antibody heavy chain, and biologically active fragments and homologs thereof.

27. The method of claim 26, wherein said antibody is a monoclonal antibody (mAb).

28. The method of claim 26, wherein said antibody is a therapeutic antibody.

29. The method of claim 1, wherein characterization data is obtained from said LC MS/MS performed on said protein fragments.

30. The method of claim 1, wherein the method is performed in a single LC MS/MS apparatus.

31. The method of claim 29, wherein the method is performed in a single run.

32. The method of claim 29, wherein the characterization data comprise at least 99% of the protein amino acid sequence.

33. The method of claim 29, wherein the characterization data comprise the identity of substantially all of the post-translational modifications of said protein.

34. The method of claim 29, wherein the characterization data comprise the location of substantially all of the post-translational modifications of said protein.

35. The method of claim 1, wherein said hydrolyzing agent is immobilized.

36. The method of claim 1, wherein a combination of electron transfer dissociation (ETD) and collision activated dissociation mass spectrometry (CAD) tandem mass spectrometry are used to characterize the resulting protein fragments.

37. The method of claim 1, wherein the protein is exposed to the hydrolyzing agent at a pH of about 3.0 to about 9.0.

38. The method of claim 37, wherein the protein is exposed to the hydrolyzing agent at a pH of about 7.0 to about 9.0.

39. The method of claim 1, wherein said reaction chamber comprises one hydrolyzing agent and said hydrolyzing agent is the protease aspergillopepsin I (SEQ ID NO:32) or a biologically active fragment or homolog thereof, wherein said homolog is a substantially homologous amino acid sequence to SEQ ID NO:32.

* * * * *

SEQUENCE LISTING

<160> NUMBER OF SEQ ID NOS: 32

<210> SEQ ID NO 1
<211> LENGTH: 40
<212> TYPE: PRT
<213> ORGANISM: Equus caballus

<400> SEQUENCE: 1

Val Leu His Ser Lys His Pro Gly Asp Phe Gly Ala Asp Ala Gln Gly
1               5                   10                  15

Ala Met Thr Lys Ala Leu Glu Leu Phe Arg Asn Asp Ile Ala Ala Lys
            20                  25                  30

Tyr Lys Glu Leu Gly Phe Gln Gly
        35                  40

<210> SEQ ID NO 2
<211> LENGTH: 52
<212> TYPE: PRT
<213> ORGANISM: mus musculus

<400> SEQUENCE: 2

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Tyr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu
    50

<210> SEQ ID NO 3
<211> LENGTH: 42

<212> TYPE: PRT
<213> ORGANISM: Mus musculus

<400> SEQUENCE: 3

Glu Val His Thr Ala His Thr Gln Pro Arg Glu Gln Phe Asn Ser
1               5                   10                  15

Thr Phe Arg Ser Val Ser Glu Leu Pro Ile Met His Gln Asp Trp Leu
            20                  25                  30

Asn Gly Lys Glu Phe Lys Cys Arg Val Asn
        35                  40

<210> SEQ ID NO 4
<211> LENGTH: 56
<212> TYPE: PRT
<213> ORGANISM: mus musculus

<400> SEQUENCE: 4

Ile Tyr Lys Val Ser Asn Arg Phe Ser Gly Val Pro Asp Arg Phe Ser
1               5                   10                  15

Gly Ser Gly Ser Gly Thr Asp Phe Thr Leu Lys Ile Ser Arg Val Glu
            20                  25                  30

Ala Glu Asp Leu Gly Val Tyr Tyr Cys Phe Gln Gly Ser His Val Pro
        35                  40                  45

Leu Thr Phe Gly Ala Gly Thr Lys
    50                  55

<210> SEQ ID NO 5
<211> LENGTH: 153
<212> TYPE: PRT
<213> ORGANISM: Equus caballus

<400> SEQUENCE: 5

Gly Leu Ser Asp Gly Glu Trp Gln Gln Val Leu Asn Val Trp Gly Lys
1               5                   10                  15

Val Glu Ala Asp Ile Ala Gly His Gly Gln Glu Val Leu Ile Arg Leu
            20                  25                  30

Phe Thr Gly His Pro Glu Thr Leu Glu Lys Phe Asp Lys Phe Lys His
        35                  40                  45

Leu Lys Thr Glu Ala Glu Met Lys Ala Ser Glu Asp Leu Lys Lys His
    50                  55                  60

Gly Thr Val Val Leu Thr Ala Leu Gly Gly Ile Leu Lys Lys Lys Gly
65                  70                  75                  80

His His Glu Ala Glu Leu Lys Pro Leu Ala Gln Ser His Ala Thr Lys
                85                  90                  95

His Lys Ile Pro Ile Lys Tyr Leu Glu Phe Ile Ser Asp Ala Ile Ile
            100                 105                 110

His Val Leu His Ser Lys His Pro Gly Asp Phe Gly Ala Asp Ala Gln
        115                 120                 125

Gly Ala Met Thr Lys Ala Leu Glu Leu Phe Arg Asn Asp Ile Ala Ala
    130                 135                 140

Lys Tyr Lys Glu Leu Gly Phe Gln Gly
145                 150

<210> SEQ ID NO 6
<211> LENGTH: 219
<212> TYPE: PRT
<213> ORGANISM: Mus musculus

<400> SEQUENCE: 6

-continued

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Tyr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Ile Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
    210                 215

<210> SEQ ID NO 7
<211> LENGTH: 441
<212> TYPE: PRT
<213> ORGANISM: mus musculus

<400> SEQUENCE: 7

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Leu Gly Tyr
            20                  25                  30

Gly Val Asn Trp Val Arg Gln Pro Pro Gly Gln Gly Leu Glu Trp Leu
        35                  40                  45

Met Gly Ile Trp Gly Asp Gly Ser Thr Asp Tyr Asn Ser Ala Leu Lys
    50                  55                  60

Ser Arg Ile Ser Ile Thr Lys Asp Asn Ser Lys Ser Gln Val Phe Leu
65                  70                  75                  80

Lys Met Asn Ser Leu Gln Thr Asp Asp Thr Ala Lys Tyr Tyr Cys Thr
                85                  90                  95

Arg Ala Pro Tyr Gly Lys Gln Tyr Phe Ala Tyr Trp Gly Gln Gly Thr
                100                 105                 110

Leu Val Thr Val Ser Ala Ala Lys Thr Thr Pro Pro Ser Val Tyr Pro
            115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn

```
                145                 150                 155                 160
Ser Gly Ser Leu Ser Ser Gly Val His Thr Phe Pro Ala Val Leu Gln
                165                 170                 175

Ser Asp Leu Tyr Thr Leu Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
                260                 265                 270

Phe Val Asp Asp Val Glu Val His Thr Ala His Thr Gln Pro Arg Glu
            275                 280                 285

Glu Gln Phe Asn Ser Thr Phe Arg Ser Val Ser Glu Leu Pro Ile Met
        290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
                340                 345                 350

Met Ala Lys Asp Lys Val Ser Leu Thr Cys Met Ile Thr Asp Phe Phe
                355                 360                 365

Pro Glu Asp Ile Thr Val Glu Trp Gln Trp Asn Gly Gln Pro Ala Glu
            370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly
                435                 440

<210> SEQ ID NO 8
<211> LENGTH: 41
<212> TYPE: PRT
<213> ORGANISM: Mus musculus

<400> SEQUENCE: 8

Val Arg Gln Pro Pro Gly Gln Gly Leu Glu Trp Leu Met Gly Ile Trp
1               5                   10                  15

Gly Asp Gly Ser Thr Asp Tyr Asn Ser Ala Leu Lys Ser Arg Ile Ser
            20                  25                  30

Ile Thr Lys Asp Asn Ser Lys Ser Gln
        35                  40

<210> SEQ ID NO 9
<211> LENGTH: 58
<212> TYPE: PRT
<213> ORGANISM: Mus musculus
```

<400> SEQUENCE: 9

Ile Tyr Lys Val Ser Asn Arg Phe Ser Gly Val Pro Asp Arg Phe Ser
1               5                   10                  15

Gly Ser Gly Ser Gly Thr Asp Phe Thr Leu Lys Ile Ser Arg Val Glu
                20                  25                  30

Ala Glu Asp Leu Gly Val Tyr Tyr Cys Phe Gln Gly Ser His Val Pro
            35                  40                  45

Leu Thr Phe Gly Ala Gly Thr Lys Leu Glu
        50                  55

<210> SEQ ID NO 10
<211> LENGTH: 38
<212> TYPE: PRT
<213> ORGANISM: Mus musculus

<400> SEQUENCE: 10

Ile Lys Arg Ala Asp Ala Ala Pro Thr Val Ser Ile Phe Pro Pro Ser
1               5                   10                  15

Ser Glu Gln Leu Thr Ser Gly Gly Ala Ser Val Val Cys Phe Leu Asn
                20                  25                  30

Asn Phe Tyr Pro Lys Asp
            35

<210> SEQ ID NO 11
<211> LENGTH: 71
<212> TYPE: PRT
<213> ORGANISM: mus musculus

<400> SEQUENCE: 11

Ile Asn Val Lys Trp Lys Ile Asp Gly Ser Glu Arg Gln Asn Gly Val
1               5                   10                  15

Leu Asn Ser Trp Thr Asp Gln Asp Ser Lys Asp Ser Thr Tyr Ser Met
                20                  25                  30

Ser Ser Thr Leu Thr Leu Thr Lys Asp Glu Tyr Glu Arg His Asn Ser
            35                  40                  45

Tyr Thr Cys Glu Ala Thr His Lys Thr Ser Thr Ser Pro Ile Val Lys
        50                  55                  60

Ser Phe Asn Arg Asn Glu Cys
65                  70

<210> SEQ ID NO 12
<211> LENGTH: 36
<212> TYPE: PRT
<213> ORGANISM: Mus musculus

<400> SEQUENCE: 12

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Leu Gly Tyr
                20                  25                  30

Gly Val Asn Trp
            35

<210> SEQ ID NO 13
<211> LENGTH: 65
<212> TYPE: PRT
<213> ORGANISM: Mus musculus

<400> SEQUENCE: 13

```
Ser Leu Gln Thr Asp Asp Thr Ala Lys Tyr Tyr Cys Thr Arg Ala Pro
1               5                   10                  15

Tyr Gly Lys Gln Tyr Phe Ala Tyr Trp Gly Gln Gly Thr Leu Val Thr
            20                  25                  30

Val Ser Ala Ala Lys Thr Thr Pro Pro Ser Val Tyr Pro Leu Ala Pro
            35                  40                  45

Gly Ser Ala Ala Gln Thr Asn Ser Met Val Thr Leu Gly Cys Leu Val
    50                  55                  60

Lys
65

<210> SEQ ID NO 14
<211> LENGTH: 62
<212> TYPE: PRT
<213> ORGANISM: mus musculus

<400> SEQUENCE: 14

Gly Tyr Phe Pro Glu Pro Val Thr Val Thr Trp Asn Ser Gly Ser Leu
1               5                   10                  15

Ser Ser Gly Val His Thr Phe Pro Ala Val Leu Gln Ser Asp Leu Tyr
            20                  25                  30

Thr Leu Ser Ser Ser Val Thr Val Pro Ser Ser Thr Trp Pro Ser Glu
            35                  40                  45

Thr Val Thr Cys Asn Val Ala His Pro Ala Ser Ser Thr Lys
    50                  55                  60

<210> SEQ ID NO 15
<211> LENGTH: 50
<212> TYPE: PRT
<213> ORGANISM: Mus musculus

<400> SEQUENCE: 15

Val Asp Lys Lys Ile Val Pro Arg Asp Cys Gly Cys Lys Pro Cys Ile
1               5                   10                  15

Cys Thr Val Pro Glu Val Ser Ser Val Phe Ile Phe Pro Pro Lys Pro
            20                  25                  30

Lys Asp Val Leu Thr Ile Thr Leu Thr Pro Lys Val Thr Cys Val Val
            35                  40                  45

Val Asp
    50

<210> SEQ ID NO 16
<211> LENGTH: 43
<212> TYPE: PRT
<213> ORGANISM: Mus musculus

<400> SEQUENCE: 16

Val Glu Val His Thr Ala His Thr Gln Pro Arg Glu Glu Gln Phe Asn
1               5                   10                  15

Ser Thr Phe Arg Ser Val Ser Glu Leu Pro Ile Met His Gln Asp Trp
            20                  25                  30

Leu Asn Gly Lys Glu Phe Lys Cys Arg Val Asn
            35                  40

<210> SEQ ID NO 17
<211> LENGTH: 52
<212> TYPE: PRT
<213> ORGANISM: Mus musculus

<400> SEQUENCE: 17
```

Ser Ala Ala Phe Pro Ala Pro Ile Glu Lys Thr Ile Ser Lys Thr Lys
1               5                   10                  15

Gly Arg Pro Lys Ala Pro Gln Val Tyr Thr Ile Pro Pro Lys Glu
            20                  25                  30

Gln Met Ala Lys Asp Lys Val Ser Leu Thr Cys Met Ile Thr Asp Phe
        35                  40                  45

Phe Pro Glu Asp
    50

<210> SEQ ID NO 18
<211> LENGTH: 70
<212> TYPE: PRT
<213> ORGANISM: Mus musculus

<400> SEQUENCE: 18

Ile Thr Val Glu Trp Gln Trp Asn Gly Gln Pro Ala Glu Asn Tyr Lys
1               5                   10                  15

Asn Thr Gln Pro Ile Met Asp Thr Asp Gly Ser Tyr Phe Val Tyr Ser
            20                  25                  30

Lys Leu Asn Val Gln Lys Ser Asn Trp Glu Ala Gly Asn Thr Phe Thr
        35                  40                  45

Cys Ser Val Leu His Glu Gly Leu His Asn His His Thr Glu Lys Ser
50                  55                  60

Leu Ser His Ser Pro Gly
65                  70

<210> SEQ ID NO 19
<211> LENGTH: 65
<212> TYPE: PRT
<213> ORGANISM: Mus musculus

<400> SEQUENCE: 19

Ser Leu Gln Thr Asp Asp Thr Ala Lys Tyr Tyr Cys Thr Arg Ala Pro
1               5                   10                  15

Tyr Gly Lys Gln Tyr Phe Ala Tyr Trp Gly Gln Gly Thr Leu Val Thr
            20                  25                  30

Val Ser Ala Ala Lys Thr Thr Pro Pro Ser Val Tyr Pro Leu Ala Pro
        35                  40                  45

Gly Ser Ala Ala Gln Thr Asp Ser Met Val Thr Leu Gly Cys Leu Val
    50                  55                  60

Lys
65

<210> SEQ ID NO 20
<211> LENGTH: 65
<212> TYPE: PRT
<213> ORGANISM: Mus musculus

<400> SEQUENCE: 20

Ser Leu Gln Thr Asp Asp Thr Ala Lys Tyr Tyr Cys Thr Arg Ala Pro
1               5                   10                  15

Tyr Gly Lys Gln Tyr Phe Ala Tyr Trp Gly Gln Gly Thr Leu Val Thr
            20                  25                  30

Val Ser Ala Ala Lys Thr Thr Pro Pro Ser Val Tyr Pro Leu Ala Pro
        35                  40                  45

Gly Ser Ala Ala Gln Thr Asn Ser Met Val Thr Leu Gly Cys Leu Val
    50                  55                  60

Lys
65

<210> SEQ ID NO 21
<211> LENGTH: 49
<212> TYPE: PRT
<213> ORGANISM: Mus musculus

<400> SEQUENCE: 21

Val Ser Leu Thr Cys Met Ile Thr Asp Phe Phe Pro Glu Asp Ile Thr
1               5                   10                  15

Val Glu Trp Gln Trp Asn Gly Gln Pro Ala Glu Asn Tyr Lys Asn Thr
            20                  25                  30

Gln Pro Ile Met Asp Thr Asp Gly Ser Tyr Phe Val Tyr Ser Lys Leu
        35                  40                  45

Asn

<210> SEQ ID NO 22
<211> LENGTH: 35
<212> TYPE: PRT
<213> ORGANISM: Mus musculus

<400> SEQUENCE: 22

Val Gln Lys Ser Asn Trp Glu Ala Gly Asn Thr Phe Thr Cys Ser Val
1               5                   10                  15

Leu His Glu Gly Leu His Asn His His Thr Glu Lys Ser Leu Ser His
            20                  25                  30

Ser Pro Gly
        35

<210> SEQ ID NO 23
<211> LENGTH: 32
<212> TYPE: PRT
<213> ORGANISM: Mus musculus

<400> SEQUENCE: 23

Lys Glu Ser Gly Pro Gly Leu Val Ala Pro Ser Gln Ser Leu Ser Ile
1               5                   10                  15

Thr Cys Thr Val Ser Gly Phe Ser Leu Leu Gly Tyr Gly Val Asn Trp
            20                  25                  30

<210> SEQ ID NO 24
<211> LENGTH: 11
<212> TYPE: PRT
<213> ORGANISM: Mus musculus

<400> SEQUENCE: 24

Tyr Tyr Cys Thr Arg Ala Pro Tyr Gly Lys Gln
1               5                   10

<210> SEQ ID NO 25
<211> LENGTH: 30
<212> TYPE: PRT
<213> ORGANISM: Mus musculus

<400> SEQUENCE: 25

Thr Val Ser Ile Phe Pro Pro Ser Ser Glu Gln Leu Thr Ser Gly Gly
1               5                   10                  15

Ala Ser Val Val Cys Phe Leu Asn Asn Phe Tyr Pro Lys Asp
            20                  25                  30

```
<210> SEQ ID NO 26
<211> LENGTH: 22
<212> TYPE: PRT
<213> ORGANISM: Mus musculus

<400> SEQUENCE: 26

Tyr Glu Arg His Asn Ser Tyr Thr Cys Glu Ala Thr His Lys Thr Ser
1               5                   10                  15

Thr Ser Pro Ile Val Lys
            20

<210> SEQ ID NO 27
<211> LENGTH: 24
<212> TYPE: PRT
<213> ORGANISM: Mus musculus

<400> SEQUENCE: 27

Ser Val Tyr Pro Leu Ala Pro Gly Ser Ala Ala Gln Thr Asn Ser Met
1               5                   10                  15

Val Thr Leu Gly Cys Leu Val Lys
            20

<210> SEQ ID NO 28
<211> LENGTH: 28
<212> TYPE: PRT
<213> ORGANISM: Mus musculus

<400> SEQUENCE: 28

Ser Ser Ser Val Thr Val Pro Ser Ser Thr Trp Pro Ser Glu Thr Val
1               5                   10                  15

Thr Cys Asn Val Ala His Pro Ala Ser Ser Thr Lys
            20                  25

<210> SEQ ID NO 29
<211> LENGTH: 9
<212> TYPE: PRT
<213> ORGANISM: Mus musculus

<400> SEQUENCE: 29

Gly Lys Glu Phe Lys Cys Arg Val Asn
1               5

<210> SEQ ID NO 30
<211> LENGTH: 5
<212> TYPE: PRT
<213> ORGANISM: Mus musculus

<400> SEQUENCE: 30

Cys Val Val Val Asp
1               5

<210> SEQ ID NO 31
<211> LENGTH: 20
<212> TYPE: PRT
<213> ORGANISM: Mus musculus

<400> SEQUENCE: 31

Ile Val Pro Arg Asp Cys Gly Cys Lys Pro Cys Ile Cys Thr Val Pro
1               5                   10                  15

Glu Val Ser Ser
            20

<210> SEQ ID NO 32
```

<211> LENGTH: 394
<212> TYPE: PRT
<213> ORGANISM: Aspergillus saitoi

<400> SEQUENCE: 32

Met Val Val Phe Ser Lys Thr Ala Ala Leu Val Leu Gly Leu Ser Thr
1               5                   10                  15

Ala Val Ser Ala Ala Pro Ala Pro Thr Arg Lys Gly Phe Thr Ile Asn
            20                  25                  30

Gln Ile Ala Arg Pro Ala Asn Lys Thr Arg Thr Val Asn Leu Pro Gly
        35                  40                  45

Leu Tyr Ala Arg Ser Leu Ala Lys Phe Gly Thr Val Pro Gln Ser
    50                  55                  60

Val Lys Glu Ala Ala Ser Lys Gly Ser Ala Val Thr Thr Pro Gln Asn
65                  70                  75                  80

Asn Asp Glu Glu Tyr Leu Thr Pro Val Thr Val Gly Lys Ser Thr Leu
                85                  90                  95

His Leu Asp Phe Asp Thr Gly Ser Ala Asp Leu Trp Val Phe Ser Asp
            100                 105                 110

Glu Leu Pro Ser Ser Glu Gln Thr Gly His Asp Leu Tyr Thr Pro Ser
        115                 120                 125

Ser Ser Ala Thr Lys Leu Ser Gly Tyr Ser Trp Asp Ile Ser Tyr Gly
    130                 135                 140

Asp Gly Ser Ser Ala Ser Gly Asp Val Tyr Arg Asp Thr Val Thr Val
145                 150                 155                 160

Gly Gly Val Thr Thr Asn Lys Gln Ala Val Glu Ala Ala Ser Lys Ile
                165                 170                 175

Ser Ser Glu Phe Val Gln Asp Thr Ala Asn Asp Gly Leu Leu Gly Leu
            180                 185                 190

Ala Phe Ser Ser Ile Asn Thr Val Gln Pro Lys Ala Gln Thr Thr Phe
        195                 200                 205

Phe Asp Thr Val Lys Ser Gln Leu Asp Ser Pro Leu Phe Ala Val Gln
    210                 215                 220

Leu Lys His Asp Ala Pro Gly Val Tyr Asp Phe Gly Tyr Ile Asp Asp
225                 230                 235                 240

Ser Lys Tyr Thr Gly Ser Ile Thr Tyr Thr Asp Ala Asp Ser Ser Gln
                245                 250                 255

Gly Tyr Trp Gly Phe Ser Thr Asp Gly Tyr Ser Ile Gly Asp Gly Ser
            260                 265                 270

Ser Ser Ser Ser Gly Phe Ser Ala Ile Ala Asp Thr Gly Thr Thr Leu
        275                 280                 285

Ile Leu Leu Asp Asp Glu Ile Val Ser Ala Tyr Tyr Glu Gln Val Ser
    290                 295                 300

Gly Ala Gln Glu Ser Tyr Glu Ala Gly Gly Tyr Val Phe Ser Cys Ser
305                 310                 315                 320

Thr Asp Leu Pro Asp Phe Thr Val Val Ile Gly Asp Tyr Lys Ala Val
                325                 330                 335

Val Pro Gly Lys Tyr Ile Asn Tyr Ala Pro Val Ser Thr Gly Ser Ser
            340                 345                 350

Thr Cys Tyr Gly Gly Ile Gln Ser Asn Ser Gly Leu Gly Leu Ser Ile
        355                 360                 365

Leu Gly Asp Val Phe Leu Lys Ser Gln Tyr Val Val Phe Asn Ser Glu
    370                 375                 380

```
Gly Pro Lys Leu Gly Phe Ala Ala Gln Ala
385                 390
```